United States Patent
Bandiera et al.

(10) Patent No.: US 11,999,734 B2
(45) Date of Patent: Jun. 4, 2024

(54) COMPOUNDS AND COMPOSITIONS FOR THE TREATMENT OF CYSTIC FIBROSIS

(71) Applicants: Fondazione Istituto Italiano Di Tecnologia, Genoa (IT); Istituto Giannina Gaslini, Genoa (IT); Fondazione Per La Ricerca Sulla Fibrosi Cistica-Onlus, Verona (IT)

(72) Inventors: Tiziano Bandiera, Genoa (IT); Fabio Bertozzi, Genoa (IT); Francesca Giacomina, Genoa (IT); Simone Giovani, Genoa (IT); Federico Sorana, Verona (IT); Emanuela Caci, Verona (IT); Loretta Ferrera, Verona (IT); Nicoletta Pedemonte, Genoa (IT); Luis Juan Vicente Galietta, Genoa (IT)

(73) Assignees: Fondazione Istituto Italiano Di Tecnologia, Genoa (IT); Istituto Giannina Gaslini, Genoa (IT); Fondazione Per La Ricerca Sulla Fibrosi Cistica—Onlus, Verona (IT)

( * ) Notice: Subject to any disclaimer, the term of this patent is extended or adjusted under 35 U.S.C. 154(b) by 662 days.

(21) Appl. No.: 17/259,221

(22) PCT Filed: Jul. 12, 2019

(86) PCT No.: PCT/IB2019/055955
§ 371 (c)(1),
(2) Date: Jan. 11, 2021

(87) PCT Pub. No.: WO2020/012427
PCT Pub. Date: Jan. 16, 2020

(65) Prior Publication Data
US 2021/0292324 A1    Sep. 23, 2021

(30) Foreign Application Priority Data

Jul. 13, 2018 (IT) .......................... 102018000007183

(51) Int. Cl.
*C07D 471/18* (2006.01)
*C07D 471/04* (2006.01)

(52) U.S. Cl.
CPC .......... *C07D 471/18* (2013.01); *C07D 471/04* (2013.01)

(58) Field of Classification Search
CPC ............................ C07D 471/18; C07D 471/04
USPC ....................................................... 514/286
See application file for complete search history.

(56) References Cited

FOREIGN PATENT DOCUMENTS

| WO | 2006099256 A2 | 9/2006 |
| WO | 2010014758 A1 | 2/2010 |

OTHER PUBLICATIONS

PCT International Search Report and Written Opinion for PCT Patent Application No. PCT/IB2019/055955 dated Dec. 11, 2019. 16 Pages.
Mattia Mori, et al., "A Combination Strategy to Inhibit Pim-1: Synergism Between Noncompetitive and ATP-Competitive Inhibitors", ChemMedChem, vol. 8, No. 3, Feb. 22, 2013, pp. 494-496. XP055281400.
Mattia Mori, et al., "A Combination Strategy to Inhibit Pim-1: Synergism Between Noncompetitive and ATP-Competitive Inhibitors", ChemMedChem, Mar. 1, 2013, pp. 484-496. XP055549401.
Peter M. Haggie et al., "Correctors and Potentiators Rescue Function of the Truncated W1282X—Cystic Fibrosis Transmembrane Regulators (CFTR) Translation Product", Journal of Biological Chemistry, vol. 292, No. 3, Jan. 20, 2017, pp. 771-785, XP055549223.
Bradford H. Hirth et al., "Discovery of 1,2,3,4-Tetrahydroisoquinoline-3-Carboxylic Acid Diamides that increase CFTR Mediated Chloride Transport", Boorganic & Medical Chemistry Letters, vol. 515, No. 8, Apr. 1, 2005, pp. 2087-2091, XP055549215.
European Patent Office, Office Action for Application No. 19 769567.9-1110, dated Dec. 16, 2021, 5 pages.
Brindani, N., et al., Identification, Structure-Activity Relationship, and Biological Characterization of 2,3,4,5-Tetrahydro-1H-pyrido[4,3-b]indoles as a Novel Class of CFTR Potentiators, J.Med.Chem 2020, 63, 26 pages.

*Primary Examiner* — Kristin A Vajda
(74) *Attorney, Agent, or Firm* — McAndrews, Held & Malloy, Ltd.

(57) ABSTRACT

The present invention relates to compounds of Formula (Ia) or pharmaceutically acceptable salts, hydrates, solvates, clathrates, polymorphs, stereoisomers thereof. It further discloses a pharmaceutical composition comprising the compounds of Formula (Ia) and the use of compounds of Formula (Ib), in particular to modulate CFTR protein or ABC protein activities.

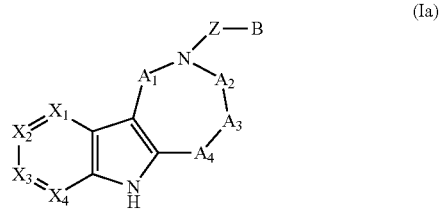

(Ia)

11 Claims, No Drawings

COMPOUNDS AND COMPOSITIONS FOR THE TREATMENT OF CYSTIC FIBROSIS

CROSS-REFERENCE TO RELATED APPLICATIONS

The present application is filed pursuant to 35 U.S.C. 371 as a U.S. National Phase application of International Patent Application No. PCT/IB2019/055955, which was filed Jul. 12, 2019, claiming the benefit of Italian patent application no. 102018000007183 filed on Jul. 13, 2018. The entire text of the aforementioned applications is incorporated herein by reference in its entirety.

TECHNICAL FIELD

The present invention relates to novel compounds to modulate CFTR protein or ABC protein activities, in particular for the treatment of cystic fibrosis.

BACKGROUND ART

Cystic fibrosis is an autosomal recessive genetic disorder caused by mutations of the gene encoding for the cystic fibrosis transmembrane conductance regulator (CFTR). The incidence of the disease among the Caucasian population is 1/2000-3000 newborns, whereas it is much lower among native Africans and Asians. Despite progress in the treatment of cystic fibrosis, there is no cure.

The cystic fibrosis transmembrane conductance regulator (CFTR) gene encodes an epithelial ion channel responsible for aiding in the regulation of salt and water absorption and secretion in various tissues.

Specifically, CFTR is a 1480 amino acid plasma membrane protein that belongs to the superfamily of ATP-binding cassette (ABC) transporters. CFTR structure consists of a cytosolic N-terminus followed by six transmembrane helices, a nucleotide-binding domain (NBD1), a regulatory (R) domain, six additional transmembrane helices, a second nucleotide-binding domain (NBD2), and a cytosolic C-terminus (Riordan, *Annu Rev Biochem* 77:701-726, 2008). The transmembrane helices form a pore permeable to chloride, bicarbonate, iodide, and other anions. Opening of the pore requires the phosphorylation of the R domain by the cAMP-dependent protein kinase A as well as binding of two ATP molecules in two pockets formed by the assembly of NBD1 and NBD2.

CFTR is a cAMP/ATP-modulated anion channel that is expressed in a variety of cells types, and particularly in epithelial cells of various organs including lungs, pancreas, liver, and intestine (Mall and Hartl, *Eur Respir J* 44:1042-1054, 2014). Physiological signals that increase intracellular cAMP levels elicit CFTR activation. In most tissues, opening of CFTR pore leads to chloride and bicarbonate secretion. A notable exception is represented by the sweat gland duct in which CFTR mediates chloride absorption and not secretion.

In epithelial cells, normal functioning of CFTR is critical for the maintenance of electrolyte transport throughout the body, including respiratory and digestive tissues.

The important role of CFTR is demonstrated by the severe pathological manifestations occurring in cystic fibrosis (CF), an inherited disease caused by mutations that lead to CFTR loss of function. In the lungs, lack of CFTR-dependent anion secretion impairs mucociliary clearance and innate antimicrobial mechanisms (Collawn and Matalon, *Am J Physiol* 307: L917-L923, 2014). Consequently, the airways become colonized by antibiotic-resistant bacteria that trigger a severe inflammatory response and a progressive loss of respiratory function. Partial loss of CFTR expression/function may also be the basis of non-genetic lung pathologies such as chronic obstructive pulmonary disease (Mall, *Ann Am Thorac Soc* 13: S177-S185, 2016).

Sequence analysis of the CFTR gene of cystic fibrosis patients has revealed a variety of disease causing mutations (Cutting, G. R. et al. (1990) Nature 346:366-369; Dean, M. et al. (1990) Cell 61:863:870; Kerem, B-S. et al. (1989) Science 245: 1073-1080; Kerem, B-S et al. (1990) Proc. Natl. Acad. Sci. USA 87:8447-8451). To date, more than 2000 CF-causing mutations in the cystic fibrosis gene have been identified, involving 6 classes of molecular defects of the protein (Class I: premature stop of CFTR protein synthesis; Class II: defective maturation and intracellular localization of the CFTR protein; Class III: impaired opening of CFTR pore; Class IV: reduced ability of CFTR pore to translocate anions; Class V: reduced CFTR protein synthesis due to altered RNA splicing; Class VI: reduced stability of CFTR at the plasma membrane leading to accelerated internalization and degradation).

A large majority of mutations have low or very low frequency (Bobadilla et al., Hum Mutat 19:575-606, 2002). However, a single mutation, F508del, is present in 50-90% of CF patients.

F508del, i.e. loss of phenylalanine at position 508 within NBD1, causes multiple defects to CFTR protein (Okiyoneda et al., Nat Chem Biol 9: 444-454, 2013). First of all, F508del-CFTR folding and stability are severely impaired. Such problems, which arise from the intrinsic instability of NBD1 and the altered interaction between NBD1 and the cytosolic loop 4, strongly reduce the trafficking of F508del-CFTR to the plasma membrane (trafficking defect). Indeed, mutant CFTR remains trapped in the endoplasmic reticulum where it is rapidly degraded by the ubiquitin-proteasome system (Lukacs and Verkman, Trends Mol Med 18: 81-91, 2012). A second defect caused by F508del is the reduction of the open channel probability, i.e. the fraction of time spent by the channel in the open state (gating defect).

The trafficking and gating defects can also be caused, often separately, by other CF mutations. For example, G85E, L1077P, A455E, and N1303K, defined as class 2 mutations, impair CFTR trafficking (Van Goor et al., J Cyst Fibros 13:29-36, 2014). Instead, G551D, G1349D, G178R, and G970R, defined as class 3 mutations, do not affect trafficking but strongly reduce CFTR open time (Yu et al., J Cyst Fibros 11:237-245, 2012).

Trafficking and gating defects caused by CF mutations are amenable to pharmacological treatment (Veit et al., Mol Biol Cell 27: 424-433, 2016). Mistrafficking can be targeted with small molecules called correctors. Gating defects can be improved with so-called potentiators. There have been several attempts to identify potentiators and correctors (Galietta, Paediatr Drugs 15:393-402, 2013). The most advanced molecule is VX-770, a potentiator also known as ivacaftor, developed by Vertex Pharmaceuticals (Van Goor et al., Proc Natl Acad Sci USA 106: 18825-18830, 2009). Given its high efficacy in clinical trials (Ramsey et al., N Engl J Med 365: 1663-1672, 2011), VX-770 has been approved (trade name Kalideco®) for the treatment of patients with G551D and other mutations belonging to class III. Vertex Pharmaceuticals has also developed the corrector VX-809, also known as lumacaftor (Van Goor et al., Proc Natl Acad Sci USA 108: 18843-18848, 2011). In clinical trials on CF patients with F508del mutation, VX-809 did not show a clear therapeutic benefit (Clancy et al., Thorax 67: 12-18, 2012). In contrast, the combination of VX-809 and VX-770, trade name Orkambi®, elicited a significant although modest improvement in respiratory function (Wainwright et al., N Engl J Med 373: 220-231, 2015). However, two separate studies reported that chronic treatment of cells with VX-770 decreases the corrector activity of VX-809 (Cholon et al., Sci Transl Med 6: 246ra96, 2014; Veit et al., Sci Transl Med 6: 246ra97, 2014). Therefore, novel types of potentiators are needed to be combined with correctors for the rescue of F508del-CFTR.

Recently, Vertex Pharmaceuticals developed the combination of the corrector VX-661, also known as tezacaftor, in combination with VX-770 (trade name Symdeco®, for the treatment of cystic fibrosis patients homozygous for the F508del-CFTR mutation (Taylor-Cousar et al., New Engl J Med 377:2013-2023, 2017), or for the treatment of cystic fibrosis patients heterozygous for the F508 deletion and a CFTR residual function mutation (Rowe et al., New Engl J Med 377:2024-2035, 2017).

Importantly, CFTR potentiators may also be beneficial for other mutations besides those belonging to class II and class III. For example, the function of mutants included in class IV (reduced CFTR channel conductance) and class V (reduced CFTR synthesis due to altered RNA splicing) can be enhanced by potentiators (Moss et al., Lancet Respir Med 3: 524-533, 2015; Yu et al., J Cyst Fibros 11: 237-245, 2012). Furthermore, the mutant W1282X, which lacks the last 199 amino acids of CFTR sequence, is partially sensitive to a combination of correctors and potentiators (Haggie et al., J Biol Chem 292: 771-785, 2017). Interestingly, CFTR potentiators are also useful for a variety of non-CF diseases. In the lungs, such molecules may be beneficial to improve the condition of patients with chronic obstructive pulmonary disease (Sloane et al., PLoS ONE 7:e39809, 2012; Solomon et al., Ann Am Thorac Soc 13:S169-S176, 2016). In the intestine, induction of CFTR-mediated fluid secretion could be beneficial for patients with chronic constipation (Cil et al., Cell Mol Gastroenterol Hepatol 2: 317-327, 2016; Cil et al., Transl Res 182: 14-26, 2017). Finally, pharmacological stimulation of CFTR is a promising strategy to treat dry eye, a common problem in aging population that leads to ocular surface inflammation (Flores et al., FASEB J 30: 1789-1797, 2016).

Accordingly, there is a need for novel compounds to be used for the treatment of CFTR mediated diseases, which involves CFTR modulator compounds.

DISCLOSURE OF INVENTION

The aim of the present invention is to provide novel compounds acting as CFTR modulators.

The aforementioned objective has been met according to compounds of claim 1, to a pharmaceutical composition of claim 6, to the uses of claims 7, 8 and 9. Preferred embodiments are set out within the dependent claims.

The following paragraphs provide definitions of the various chemical moieties of the compounds according to the invention and are intended to apply uniformly throughout the specification and claims unless an otherwise expressly set out definition provides a broader definition.

The term "alkyl", as used herein, refers to saturated aliphatic hydrocarbon groups. Such term includes straight (unbranched) chains or branched chains.

Non-limiting examples of alkyl groups according to the invention are, for example, methyl, ethyl, propyl, isopropyl, n-butyl, iso-butyl, tert-butyl, n-pentyl, iso-pentyl, n-hexyl and the like.

Alkyl groups according to the present invention may be unsubstituted or substituted by one or more substituents as defined below.

The term "cycloalkyl", as used herein, refers to a saturated or partially unsaturated carbocyclic group having a single ring. It includes cycloalkenyl groups.

Non-limiting examples of cycloalkyl groups according to the invention are, for example, cyclopropane, cyclobutane, cyclopentane, cyclohexane, cycloheptane, cyclopentene, cyclohexene, cyclohexadiene and the like.

Cycloalkyl groups according to the present invention may be unsubstituted or substituted by one or more substituents as defined below.

The term "heterocycloalkyl" group, ("non-aromatic heterocycle" group), refers to a cycloalkyl group (non aromatic group) wherein at least one of the carbon atoms has been replaced by a heteroatom selected from nitrogen, oxygen and sulfur. Heterocycloalkyl groups can be unsubstituted or substituted by one or more substituents as defined below.

Examples of heterocycloalkyls include, but are not limited to, lactams, lactones, cyclic imides, cyclic thioimides, cyclic carbamates, 1-(1,2,5,6-tetrahydropyridyl), tetrahydrothiopyran, 4H-pyran, tetrahydropyran, piperidine (1-piperidinyl, 2-piperidinyl, 3-piperidinyl), 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, morpholine (4-morpholinyl, 3-morpholinyl, 2-morpholinyl) trioxane, hexahydro-1,3,5-triazine, tetrahydrothiophene, tetrahydrofuran (tetrahydrofuran-2-yl, tetrahydrofuran-3-yl), pyrroline, pyrrolidine, pyrrolidone, pyrrolidindione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane.

The term "halogen", as used herein, refers to fluorine, chlorine, bromine and iodine.

The term "aryl", as used herein, refers to a hydrocarbon consisting of an unsubstituted or substituted mono-, bi- or tricarbocyclic ring system, wherein the rings are fused together and at least one of the carbocyclic ring is aromatic. The term "aryl" means for example a cyclic aromatic such as a 6-membered hydrocarbon ring, a two six-membered fused hydrocarbon rings. Non-limiting examples of aryl groups are, for example, phenyl, alpha- or beta-naphthyl, 9,10-dihydroanthracenyl, indanyl, fluorenyl and the like. Aryl groups according to the present invention may be unsubstituted or substituted by one or more substituents as defined below.

The term "heteroaryl", as used herein, refers to an aryl as defined above wherein one to four carbon atoms are independently replaced by heteroatoms chosen from the group consisting of nitrogen, oxygen and sulphur. Non-limiting examples of heteroaryl groups are, for example, pyrrolyl, furyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, tetrazolyl, pyridyl, pyrazinyl, pyrimidinyl, pyridazinyl, quinolinyl, isoquinolinyl, quinazolinyl, quinoxalinyl. Heteroaryl groups according to the present invention may be unsubstituted or substituted by one or more substituents as defined below.

Unless otherwise indicated, the term "substituted", as used herein, means that one or more hydrogen atoms of the above mentioned groups are replaced with another non-hydrogen atom or functional group referred to as substituent, provided that normal valencies are maintained and that the substitution results in a stable compound. Non-limiting example of substituents are, for example, OH, $C_{1-6}$alkyl, aryl, $C_{1-6}$alkylaryl, $C_{3-6}$cycloalkyl, O—$C_{1-6}$alkyl, O—$C_{3-6}$cycloalkyl, O-aryl, O—$C_{1-6}$alkylaryl, heteroaryl, O-heteroaryl, O-heterocycloalkyl, trifluoromethyl, difluoromethyl, trifluoromethoxy, difluoromethoxy, acyl, aroyl, heteroaroyl, halogen, nitro, cyano, COOR$^z$, alkylthio, arylthio, alkylsulfinyl, arylsulfinyl, alkylsulfonyl, arylsulfonyl, —O—C(=O)—NR$^h$R$^k$, —C(=O)—NR$^h$R$^k$, and —NR$^p$R$^q$, wherein each of R$^z$, R$^h$, and R$^k$, independently represents hydrogen, $C_{1-6}$alkyl, $C_{3-6}$cycloalkyl, aryl, $C_{1-6}$alkylaryl, heteroaryl, heterocycloalkyl, and R$^p$ and R$^q$ independently represents hydrogen, $C_{1-6}$alkyl, $C_{3-6}$cycloalkyl, aryl, $C_{1-6}$alkylaryl, heteroaryl, heterocycloalkyl, COR$^z$, COOR$^z$, —C(=O)—NR$^h$R$^k$, —S(=O)$_2$—R$^z$, and —S(=O)$_2$—NR$^h$R$^k$, and when R$^h$ and R$^k$, or R$^p$ and R$^q$ are taken together with the nitrogen atom to which they are bound, the group —NR$^h$R$^k$ or the group NR$^p$R$^q$ represent a heterocycloalkyl residue, and wherein the terms alkyl, cycloalkyl, aryl, heteroaryl, heterocyclyl are as above defined.

Preferred substituents are OH, $C_{1-6}$alkyl, O—$C_{1-6}$alkyl, trifluoromethyl, difluoromethyl, halogen, $C_{3-6}$cycloalkyl, O—$C_{3-6}$cycloalkyl, trifluoromethoxy, difluoromethoxy, cyano, —NR$^p$R$^q$ and COOR$^z$ wherein R$^z$ is selected from the group consisting of H, methyl, ethyl, propyl, butyl, i-propyl, t-butyl, and R$^p$ and R$^q$ are independently selected from H, methyl, ethyl, butyl, i-propyl, phenyl, COR$^z$, COOR$^z$, —C(=O)—NR$^h$R$^k$, and —S(=O)$_2$—R$^z$. More preferred substituents are selected from OH, methyl, methoxy, chlorine, fluorine, trifluoromethyl, trifluoromethoxy, cyano, —NR$^p$R$^q$ and COOR$^z$ wherein R$^z$ is selected from the group consisting of H, methyl, ethyl and t-butyl, and R$^p$ and R$^q$ are independently selected from H, methyl, ethyl, butyl, i-propyl, phenyl, and acyl.

The term "pharmaceutically acceptable salts" refers to salts of the below identified compounds of Formula (Ia) and (Ib) that retain the desired biological activity and are accepted by regulatory authorities.

As used herein, the term "salt" refers to any salt of a compound according to the present invention prepared from an inorganic or organic acid or base and internally formed salts. Typically, such salts have a physiologically acceptable anion or cation.

Furthermore, the compounds of Formula (Ia) and (Ib) may form an acid addition salt or a salt with a base, depending on the kind of the substituents, and these salts are included in the present invention, as long as they are pharmaceutically acceptable salts.

Examples of such salts include, but are not restricted to acid addition salts formed with inorganic acids (e. g. hydrochloric acid, hydrobromic acid, sulfuric acid, phosphoric acid, nitric acid, and the like), and salts formed with organic acids such as acetic acid, trifluoroacetic acid, oxalic acid, tartaric acid, succinic acid, malic acid, fumaric acid, maleic acid, ascorbic acid, benzoic acid, alginic acid, polyglutamic acid, methanesulfonic acid, p-toluene sulfonic acid, and naphthalene sulfonic acid.

The compounds of Formula (Ia) and (Ib) containing acidic protons may be converted into their therapeutically active, non-toxic base addition salt forms, e.g. metal or amine salts, by treatment with appropriate organic and inorganic bases. Appropriate base salt forms include, for example, ammonium salts, alkali and earth alkaline metal salts, e.g. lithium, sodium, potassium, magnesium, calcium salts and the like, salts with organic bases, e.g. N-methyl-D-glucamine, hydrabamine salts, and salts with amino acids such as, for example, arginine, lysine and the like.

Physiologically or pharmaceutically acceptable salts are particularly suitable for medical applications because of their greater aqueous solubility relative to the parent compound.

Pharmaceutically acceptable salts may also be prepared from other salts including other pharmaceutically acceptable salts of the compounds of Formula (Ia) and (Ib) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention. The compounds of Formula (Ia) and (Ib) may readily be isolated in association with solvent molecules by crystallization or evaporation of an appropriate solvent to give the corresponding solvates.

The compounds of Formula (Ia) and (Ib) may be in crystalline form. In certain embodiments, the crystalline forms of the compounds of Formula (Ia) and (Ib) are polymorphs.

The subject invention also includes isotopically-labelled compounds, which are identical to those recited in Formula (Ia) and (Ib) and following, but differ for the fact that one or more atoms are replaced by an atom having an atomic mass or mass number different from the atomic mass or mass number usually found in nature. Examples of isotopes that can be incorporated into the compounds of the invention and pharmaceutically acceptable salts thereof include isotopes of hydrogen, carbon, nitrogen, oxygen, sulfur, fluorine, and chlorine, such as $^2$H, $^3$H, $^{11}$C, $^{13}$C, $^{14}$C, $^{15}$N, $^{17}$O, $^{18}$O, $^{35}$S, $^{18}$F, $^{36}$Cl.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e. $^3$H, and carbon-14, i.e. $^{14}$C, isotopes are particularly preferred for their ease of preparation and detectability. $^{11}$C and $^{18}$F isotopes are particularly useful in PET (Positron Emission Tomography). Furthermore, substitution with heavier isotopes such as deuterium, i.e. $^2$H, can afford certain therapeutic advantages resulting from greater metabolic stability, for example increased in vivo half-life or reduced dosage requirements and, hence, may be preferred in some circumstances. Isotopically-labelled compounds of Formula (Ia) and (Ib) and following of this invention can generally be prepared by carrying out the procedures disclosed in the Schemes and/or in the Examples below, by replacing a non-isotopically-labelled reagent with a readily available isotopically-labelled reagent.

Certain groups/substituents included in the present invention may be present as isomers or in one or more tautomeric forms. Accordingly, in certain embodiments, the compounds of Formula (Ia) and (Ib) may exist in the form of other tautomers or geometrical isomers in some cases, depending on the kinds of the substituents. In the present specification, the compounds may be described in only one form of such isomers, but the present invention includes all such isomers, isolated forms of the isomers, or a mixture thereof. Furthermore, the compounds of Formula (Ia) and (Ib) may have asymmetric carbon atoms or axial asymmetries in some cases and, correspondingly, they may exist in the form of optical isomers such as an (R)-form, an (S)-form, and the like. The present invention includes within the scope all such isomers, including racemates, enantiomers and mixtures thereof.

In particular, within the scope of the present invention are included all stereoisomeric forms, including enantiomers, diastereoisomers, and mixtures thereof, including racemates and the general reference to the compounds of Formula (Ia) and (Ib) includes all the stereoisomeric forms, unless otherwise indicated.

In general, the compounds or salts of the invention should be interpreted as excluding those compounds (if any) which are so chemically unstable, either per se or in water, that they are clearly unsuitable for pharmaceutical use through all administration routes, whether oral, parenteral, or otherwise. Such compounds are known to the skilled chemist.

According to a first aspect of the invention, compounds of Formula (Ia):

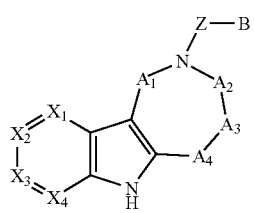

(Ia)

or pharmaceutically acceptable salts, hydrates, solvates, clathrates, polymorphs, stereoisomers thereof are provided.

In the compounds of Formula (Ia):

Z is selected from the group consisting of C=O, SO$_2$ or CONR$^i$;

R$^i$ is selected from the group consisting of hydrogen, C$_{1-6}$alkyl, C$_{3-6}$cycloalkyl, and heterocycloalkyl;

X$_1$, X$_2$, X$_3$ and X$_4$ are independently selected from the group consisting of CR$^{ii}$ and N, with the proviso that the number of nitrogen atoms in the ring is comprised from 0 to 2;

each R$^{ii}$ is independently selected from the group consisting of hydrogen, C$_{1-6}$alkyl, haloC$_{1-6}$alkyl, C$_{3-6}$cycloalkyl, heterocycloalkyl, aryl, heteroaryl, O-aryl, O-heteroaryl, COR$^{viii}$, COOR$^{viii}$, CONHR$^c$, CONR$^d$R$^e$, OH, O—C$_{1-6}$alkyl, O—C$_{3-6}$cycloalkyl, O-heterocycloalkyl, O-haloC$_{1-6}$alkyl, C$_{1-6}$alkyl-O—C$_{1-6}$alkyl, C$_{1-6}$alkyl-O—C$_{3-6}$cycloalkyl, C$_{1-6}$alkyl-O-heterocycloalkyl, CN, NO$_2$, NHR$^c$, NR$^d$R$^e$, N(R$^e$)COR$^c$, N(R$^e$)COOR$^c$, N(R$^x$)CONR$^{ix}$R$^x$, N(R$^x$)SO$_2$R$^{xi}$, SO$_2$R$^{xi}$, SO$_2$NHR$^c$, SO$_2$NR$^d$R$^e$, halogen, and hydroxy-C$_{1-6}$alkyl;

A$_1$ and A$_4$ are CR$^{iii}$R$^{iv}$,

A$_2$ and A$_3$ are selected from a bond and CR$^{iii}$R$^{iv}$;

R$^{iii}$ and R$^{iv}$ are independently selected from the group consisting of hydrogen, C$_{1-6}$alkyl, C$_{3-6}$cycloalkyl, heterocycloalkyl, haloC$_{1-6}$alkyl, COR$^{viii}$, COOR$^{viii}$, CONHR$^{viii}$, CONR$^{ix}$R$^x$, OH, O—C$_{1-6}$alkyl, C$_{1-6}$alkyl-O—C$_{1-6}$alkyl, CN, halogen, NR$^{ix}$R$^x$, N(R$^{ix}$)COR$^{viii}$ or R$^{iii}$ and R$^{iv}$ form a C$_3$-C$_6$ cycloalkyl with the C to which they are linked;

or, when A$_3$ is a bond, two groups R$^{iv}$ on A$_1$ and A$_2$, or on A$_1$ and A$_4$ are linked together to form a ring and thus the moiety

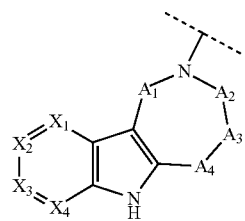

represents one of the structures selected from the group consisting of:

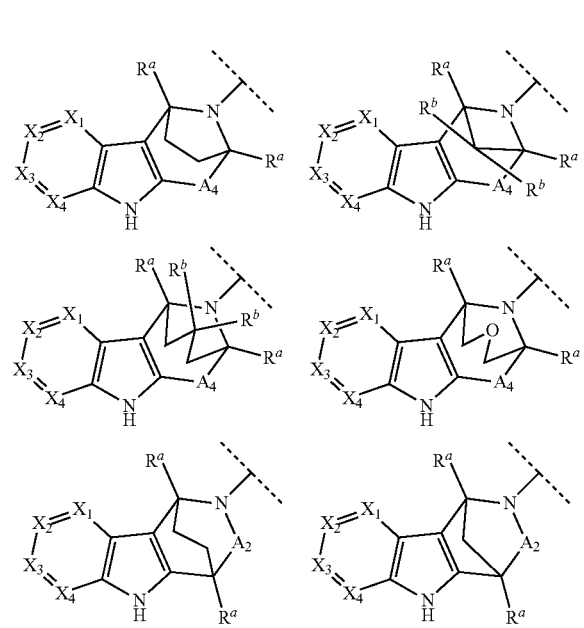

wherein R$^a$ and R$^b$ are independently selected from the group consisting of hydrogen, C$_{1-6}$alkyl, halogen, OH, O—C$_{1-6}$alkyl, C$_{1-6}$alkyl-O—C$_{1-6}$alkyl, B is selected from the group consisting of:

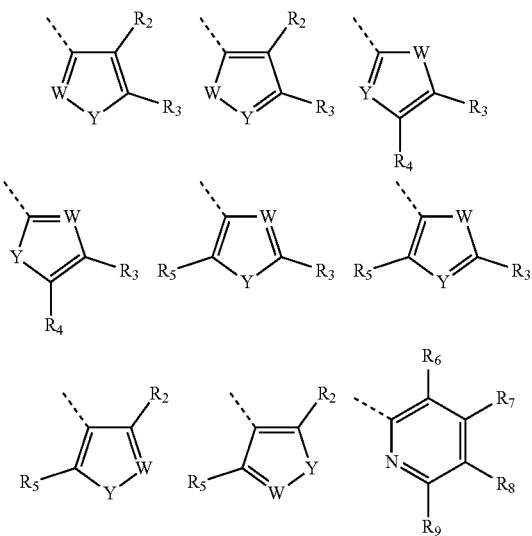

-continued

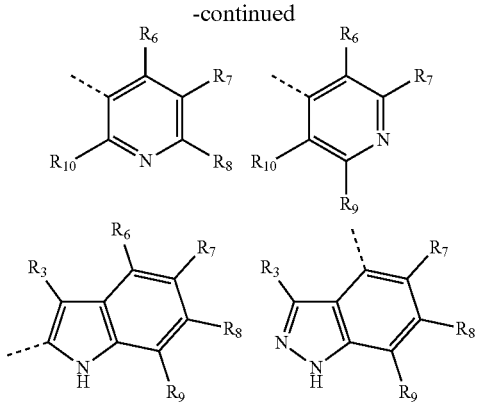

wherein

Y and W are independently selected from the group consisting of O, S, $CR^v$, $CR^vR^{vi}$, N, and $NR^{vii}$, wherein $R^v$ and $R^{vi}$ are selected form the group consisting of hydrogen, $C_{1-6}$alkyl, halo$C_{1-6}$alkyl, $C_{3-6}$cycloalkyl, heterocycloalkyl, aryl, heteroaryl, O—$C_{1-6}$alkyl, O—$C_{1-6}$alkylaryl, O—$C_{3-6}$cycloalkyl, O-heterocycloalkyl, O-halo$C_{1-6}$alkyl, $C_{1-6}$alkyl-O—$C_{1-6}$alkyl, $C_{1-6}$alkyl-O—$C_{3-6}$cycloalkyl, $C_{1-6}$alkyl-O-heterocycloalkyl, $C_{1-6}$alkyl-O-aryl, $C_{1-6}$alkyl-O-heteroaryl, hydroxy-$C_{1-6}$alkyl, $COR^{viii}$, $COOR^{viii}$, $CONHR^{viii}$, and $CONR^{ix}R^x$;

$R^{vii}$ is selected form the group consisting of hydrogen, $C_{1-6}$alkyl, halo$C_{1-6}$alkyl, $C_{3-6}$cycloalkyl, heterocycloalkyl, aryl, heteroaryl, $C_{2-6}$alkyl-O—$C_{1-6}$alkyl, $C_{2-6}$alkyl-O—$C_{3-6}$cycloalkyl, $C_{2-6}$alkyl-O-heterocycloalkyl, $C_{2-6}$alkyl-O-aryl, and $C_{2-6}$alkyl-O-heteroaryl;

$R_2$, $R_3$, $R_4$, $R_5$, $R_6$, $R_7$, $R_8$, $R_9$ and $R_{10}$ are independently selected from the group consisting of hydrogen, $C_{1-6}$alkyl, halo$C_{1-6}$alkyl, $C_{3-6}$cycloalkyl, heterocycloalkyl, aryl, heteroaryl, $COR^{viii}$, $COOR^{viii}$, $CONHR^{viii}$, $CONR^{ix}R^x$, OH, O—$C_{1-6}$alkyl, O—$C_{1-6}$alkylaryl, O—$C_{3-6}$cycloalkyl, O-heterocycloalkyl, O-heteroaryl, O-aryl, O-halo$C_{1-6}$alkyl, $C_{1-6}$alkyl-O—$C_{1-6}$alkyl, $C_{1-6}$alkyl-O—$C_{3-8}$cycloalkyl, $C_{1-6}$alkyl-O-heterocycloalkyl, $C_{1-6}$alkyl-O-aryl, $C_{1-6}$alkyl-O-heteroaryl, hydroxy-$C_{1-6}$alkyl, CN, $NO_2$, $NR^{ix}R^x$, $N(R^x)COR^{viii}$, $N(R^x)COOR^{viii}$, $N(R^x)CONR^{ix}R^x$, $N(R^x)$ $SO_2R^{xi}$, $SO_2R^{xi}$, $SO_2NR^{ix}R^x$, and halogen;

$R^{viii}$ is selected from the group consisting of hydrogen, $C_{1-6}$alkyl, halo$C_{1-6}$alkyl, $C_{3-6}$cycloalkyl, heterocycloalkyl, aryl, heteroaryl, $C_{1-6}$alkyl-O—$C_{1-6}$alkyl, and $C_{1-6}$alkyl-O-heterocycloalkyl;

$R^{ix}$ is selected from the group consisting of hydrogen, $C_{1-6}$alkyl, halo$C_{1-6}$alkyl, $C_{3-6}$cycloalkyl, heterocycloalkyl, aryl, and heteroaryl;

$R^x$ is selected from the group consisting of hydrogen, $C_{1-6}$alkyl, halo$C_{1-6}$alkyl, $C_{3-6}$cycloalkyl, heterocycloalkyl, aryl, heteroaryl, $C_{1-6}$alkyl-O—$C_{2-6}$alkyl, and hydroxy-$C_{2-6}$alkyl;

$R^{xi}$ is selected from the group consisting of $C_{1-6}$alkyl, halo$C_{1-6}$alkyl, $C_{3-6}$cycloalkyl, heterocycloalkyl, aryl, and heteroaryl;

$R^c$ is selected from the group consisting of hydrogen, $C_{1-6}$alkyl, halo$C_{1-6}$alkyl, $C_{2-6}$alkyl-O—$C_{1-6}$alkyl, and $C_{2-6}$alkyl-O-heterocycloalkyl;

$R^d$ is selected from the group consisting of $C_{1-6}$alkyl, halo$C_{1-6}$alkyl, aryl, and heteroaryl;

$R^e$ is selected from the group consisting of $C_{1-6}$alkyl, halo$C_{1-6}$alkyl, aryl, heteroaryl, $C_{1-6}$alkyl-O—$C_{2-6}$alkyl, and hydroxy-$C_{2-6}$alkyl;

provided that at least one of $R^{iii}$ or $R^{iv}$ of at least one of $A_1$, $A_2$, $A_3$ or $A_4$ is not H and that, when Z is C=O, $A_1$ is not $CH(C_{1-6}$alkyl) when $A_4$ is $CH_2$ or $A_1$ is not $CH_2$ when $A_4$ is $CH(C_{1-6}$alkyl).

According to a first embodiment, Z is C=O.

According to a second embodiment, $X_1$, $X_2$, $X_3$ and $X_4$ are $CR^{ii}$.

According to a third embodiment, each $R^{ii}$ is independently selected from the group consisting of hydrogen, $C_{1-6}$alkyl, halo$C_{1-6}$alkyl, $C_{3-6}$cycloalkyl, heterocycloalkyl, $COR^{viii}$, $COOR^{viii}$, $CONHR^c$, $CONR^dR^e$, OH, O—$C_{1-6}$alkyl, O—$C_{3-6}$cycloalkyl, O-heterocycloalkyl, O-halo$C_{1-6}$alkyl, $C_{1-6}$alkyl-O—$C_{1-6}$alkyl, $C_{1-6}$alkyl-O—$C_{3-6}$cycloalkyl, $C_{1-6}$alkyl-O-heterocycloalkyl, CN, $NO_2$, $NHR^c$, $NR^dR^e$, $SO_2R^{xi}$, $SO_2NHR^c$, $SO_2NR^dR^e$, halogen, and hydroxy-$C_{1-6}$alkyl.

According to a fourth embodiment, $R^{iii}$ and $R^{iv}$ are independently selected from the group consisting of hydrogen, $C_{1-6}$alkyl, $C_{3-6}$cycloalkyl, heterocycloalkyl, halo$C_{1-6}$alkyl, $COR^{viii}$, $COOR^{viii}$, $CONHR^{viii}$, $CONR^{ix}R^x$, OH, O—$C_{1-6}$alkyl, $C_{1-6}$alkyl-O—$C_{1-6}$alkyl, CN, halogen.

Alternatively, $R^{iii}$ and $R^{iv}$ are independently selected from the group consisting of hydrogen and $C_{1-6}$alkyl, halo$C_{1-6}$ alkyl, OH, O—$C_{1-6}$alkyl, halogen or, when $A_3$ is a bond, two groups $R^{iv}$ on $A_1$ and $A_2$, are linked together to form a ring and thus the moiety

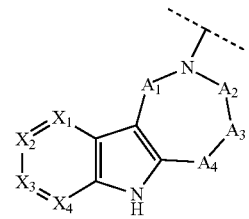

represents:

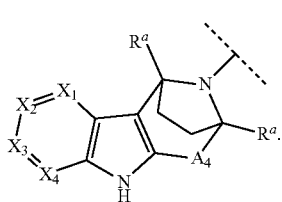

In a further embodiment, $R^{iii}$ and $R^{iv}$ are independently selected from the group consisting of hydrogen and methyl.

According to a further embodiment of the invention, the compounds of Formula (ta) can be selected from the group consisting of:

| | |
|---|---|
| 040 | (2-methyl-5,6,7,8,9,10-hexahydro-7,10-epiminocyclohepta[b]indol-11-yl) (5-(trifluoromethyl)-1H-pyrazol-3-yl)methanone |
| 041 | (1H-indol-2-yl) (2-methyl-5,6,7,8,9,10-hexahydro-7,10-epiminocyclohepta[b]indol-11-yl)methanone |
| 042 | (5-bromofuran-2-yl) (2-methyl-5,6,7,8,9,10-hexahydro-7,10-epiminocyclohepta[b]indol-11-yl) methanone |

| | |
|---|---|
| 047 | [5-(trifluoromethyl)1H-pyrazol-3-yl]-(4,4,8-trimethyl-3,5-dihydro-1H-pyrido[4,3-b]indol-2-yl)methanone |
| 053 | (4-fluoro-2-methyl-5,6,7,8,9,10-hexahydro-7,10-epiminocyclohepta[b]indol-11-yl) (5-(trifluoromethyl)-1H-pyrazol-3-yl) methanone |
| 055 | (4-fluoro-1-methyl-5,6,7,8,9,10-hexahydro-7,10-epiminocyclohepta[b]indol-11-yl) (5-(trifluoromethyl)-1H-pyrazol-3-yl)methanone |
| 077 | (6-fluoro-4,4,9-trimethyl-3,5-dihydro-1H-pyrido [4,3-b]indol-2-yl)-[5-(trifluoromethyl)-1H-pyrazol-3-yl]methanone |
| 079 | (7R,10S)- or (7S,10R)-(4-fluoro-1-methyl-5,6,7,8,9,10-hexahydro-7,10-epiminocyclohepta[b]indol-11-yl) (5-(trifluoromethyl)-1H-pyrazol-3-yl)methanone |
| 080 | (7S,10R)- or (7R,10S)-4-fluoro-1-methyl-5,6,7,8,9,10-hexahydro-7,10-epiminocyclohepta[b]indol-11-yl) (5-(trifluoromethyl)-1H-pyrazol-3-yl)methanone |
| 105 | rac-(6-fluoro-3,9-dimethyl-1,3,4,5-tetrahydropyrido[4,3-b]indol-2-yl)-[5-(trifluoromethyl)-1H-pyrazol-3-yl]methanone |
| 108 | (R)-(6-fluoro-3,9-dimethyl-1,3,4,5-tetrahydropyrido[4,3-b]indol-2-yl)-[5-(trifluoromethyl)-1H-pyrazol-3-yl]methanone |
| 109 | (S)-(6-fluoro-3,9-dimethyl-1,3,4,5-tetrahydropyrido[4,3-b]indol-2-yl)-[5-(trifluoromethyl)-1H-pyrazol-3-yl]methanone |
| 112 | (6-fluoro-3,3,9-trimethyl-4,5-dihydro-1H-pyrido[4,3-b]indol-2-yl)-[5-(trifluoromethyl)-1H-pyrazol-3-yl]methanone |
| 113 | [(S)-6,9-difluoro-3-methyl-1,3,4,5-tetrahydropyrido[4,3-b]indol-2-yl]-[5-(trifluoromethyl)-1H-pyrazol-3-yl]methanone |
| 114 | [(R)-6-fluoro-3,9-dimethyl-1,3,4,5-tetrahydropyrido[4,3-b]indol-2-yl]-(1H-indol-2-yl)methanone |
| 115 | [(S)-8-methoxy-6-fluoro-3-methyl-1,3,4,5-tetrahydropyrido[4,3-b]indol-2-yl]-[5-(trifluoromethyl)-1H-pyrazol-3-yl]methanone |
| 117 | [(R)-8-methoxy-6-fluoro-3-methyl-1,3,4,5-tetrahydropyrido[4,3-b]indol-2-yl]-[5-(trifluoromethyl)-1H-pyrazol-3-yl]methanone |
| 121 | (6-fluoro-3-isopropyl-8-methoxy-1,3,4,5-tetrahydropyrido[4,3-b]indol-2-yl)-(5-methyl-1H-pyrazol-3-yl)methanone |
| 122 | (6,9-difluoro-8-methoxy-spiro[4,5-dihydro-3H-pyrido[4,3-b]indole-1,1'-cyclopropane]-2-yl)-(5-methyl-1H-pyrazol-3-yl)methanone |
| 123 | (6,9-difluoro-1,3-dimethyl-1,3,4,5-tetrahydropyrido[4,3-b]indol-2-yl)-(5-methyl-1H-pyrazol-3-yl)methanone |
| 124 | (6,9-difluoro-8-methoxy-spiro[4,5-dihydro-1H-pyrido[4,3-b]indole-3,1'-cyclopropane]-2-yl)-(5-methyl-1H-pyrazol-3-yl)methanone |
| 125 | [6-(dimethylamino)-1H-indol-2-yl]-(8-methylspiro[3,5-dihydro-1H-pyrido[4,3-b]indole-4,1'-cyclopropane]-2-yl)methanone |
| 126 | (4-ethyl-6-fluoro-9-methyl-1,3,4,5-tetrahydropyrido[4,3-b]indol-2-yl)-(5-methyl-1H-pyrazol-3-yl)methanone |
| 127 | 6-fluoro-9-methyl-2-(5-methyl-1H-pyrazole-3-carbonyl)-1,3,4,5-tetrahydropyrido[4,3-b]indole-3-carboxylic acid |
| 128 | [6-(dimethylamino)-1H-indol-2-yl]-[8-methyl-1-(trifluoromethyl)-1,3,4,5-tetrahydropyrido[4,3-b]indol-2-yl]methanone |
| 129 | (6-fluoro-8-methoxy-1,4-dimethyl-1,3,4,5-tetrahydropyrido[4,3-b]indol-2-yl)-(5-methyl-1H-pyrazol-3-yl)methanone |
| 130 | (6-fluoro-4-methoxy-9-methyl-1,3,4,5-tetrahydropyrido[4,3-b]indol-2-yl)-(5-methyl-1H-pyrazol-3-yl)methanone |
| 131 | 6-fluoro-4,9-dimethyl-2-(5-methyl-1H-pyrazole-3-carbonyl)-3,5-dihydro-1H-pyrido[4,3-b]indole-4-carboxylic acid |
| 132 | (4,4-difluoro-8-methoxy-3,5-dihydro-1H-pyrido[4,3-b]indol-2-yl)-(5-methyl-1H-pyrazol-3-yl)methanone |
| 133 | (3,6-dimethyl-4,8,10-triazatricyclo[7.4.0.02,7]trideca-1(9),2(7),10,12-tetraen-4-yl)-(5-methyl-1H-pyrazol-3-yl)methanone |
| 134 | (6,6-dimethyl-4,8,12-triazatricyclo[7.4.0.02,7]trideca-1(9),2(7),10,12-tetraen-4-yl)-(5-methyl-1H-pyrazol-3-yl)methanone |
| 135 | 2-(5-bromofuran-2-carbonyl)-8-methoxy-1,3,4,5-tetrahydropyrido[4,3-b]indole-4-carboxylic acid |

A second aspect of the present invention relates to a pharmaceutical composition comprising a compound of Formula (Ia) as disclosed above and a pharmaceutically acceptable carrier, stabilizer, diluent or excipient thereof.

A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral administration (including subcutaneous and intravenous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

Pharmaceutical compositions containing a compound of this invention can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of the present invention can be administered by a variety of routes including oral, rectal, subcutaneous, intravenous, intramuscular, intranasal and pulmonary routes. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include pre-filled, pre-measured ampoules or syringes of the liquid compositions or pills, tablets, capsules or the like in the case of solid compositions.

Liquid forms suitable for oral administration may include a suitable aqueous or non-aqueous vehicle with buffers, suspending and dispensing agents, colorants, flavours and the like. Solid forms may include, for example, any of the following ingredients, or compounds of a similar nature: a binder such as microcrystalline cellulose, gum tragacanth, acacia, corn starch or gelatine; an excipient such as starch, dicalcium phosphate or lactose, a disintegrating agent such as alginic acid, Primogel or corn starch; a lubricant such as magnesium stearate; a glidant such as colloidal silicon dioxide; a sweetening agent such as sucrose, lactose or saccharin; or a flavouring agent such as peppermint, methyl salicylate, or orange flavouring.

Injectable compositions are typically based upon injectable sterile saline or phosphate-buffered saline or other injectable carriers known in the art.

The pharmaceutical compositions may be in the form of tablets, pills, capsules, solutions, suspensions, emulsion, powders, suppository and as sustained release formulations.

If desired, tablets may be coated by standard aqueous or non-aqueous techniques. In certain embodiments, such compositions and preparations can contain at least 0.1 percent of active compound. The percentage of active compound in these compositions may, of course, be varied and may conveniently be between about 1 percent to about 60 percent of the weight of the unit. The amount of active compound in such therapeutically useful compositions is such that therapeutically active dosage will be obtained.

When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring agent such as cherry or orange flavor. To prevent breakdown during transit through the upper portion of the gastrointestinal tract, the composition be an enteric coated formulation.

The active compounds can also be administered intranasally as, for example, liquid drops or spray.

Compositions for pulmonary administration include, but are not limited to, dry powder compositions consisting of the powder of a compound of Formula (Ia) or a salt thereof, and the powder of a suitable carrier and/or lubricant. The compositions for pulmonary administration can be inhaled from any suitable dry powder inhaler device known to a person skilled in the art.

Administration of the compositions is performed under a protocol and at a dosage sufficient to reduce the inflammation and pain in the subject. In some embodiments, in the pharmaceutical compositions of the present invention the active principle or active principles are generally formulated in dosage units. The dosage unit may contain from 0.1 to 1000 mg of a compound of Formula (Ia) per dosage unit for daily administration.

In some embodiments, the amounts effective for a specific formulation will depend on the severity of the disease, disorder or condition, previous therapy, the individual's health status and response to the drug. In some embodiments, the dose is in the range from 0.001% by weight to about 60% by weight of the formulation.

When used in combination with one or more other active ingredients, the compound of the present invention and the other active ingredient may be used in lower doses than when each is used singly.

Concerning formulations with respect to any variety of routes of administration, methods and formulations for the administration of drugs are disclosed in Remington's Pharmaceutical Sciences, 17th Edition, Gennaro et al. Eds., Mack Publishing Co., 1985, and Remington's Pharmaceutical Sciences, Gennaro A R ed. 20th Edition, 2000, Williams & Wilkins PA, USA, and Remington: The Science and Practice of Pharmacy, 21st Edition, Lippincott Williams & Wilkins Eds., 2005; and in Loyd V. Allen and Howard C. Ansel, Ansel's Pharmaceutical Dosage Forms and Drug Delivery Systems, 10th Edition, Lippincott Williams & Wilkins Eds., 2014.

The above described components for orally administered or injectable compositions are merely representative.

The compounds of this invention can also be administered in sustained release forms or from sustained release drug delivery systems.

A third aspect of the present invention relates to compounds of Formula (Ia) as disclosed above or the pharmaceutical composition thereof, for the use as a medicament.

A fourth aspect of the present invention relates to compounds of Formula (Ib)

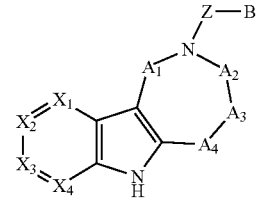

(Ib)

or pharmaceutically acceptable salts, hydrates, solvates, clathrates, polymorphs, stereoisomers thereof, for the use to potentiate CFTR protein or ABC protein activities.

In the compounds of Formula (Ib):

Z is selected from the group consisting of C=O, $SO_2$ or $CONR^i$;

$R^i$ is selected from the group consisting of hydrogen, $C_{1-6}$alkyl, $C_{3-6}$cycloalkyl, and heterocycloalkyl;

$X_1$, $X_2$, $X_3$ and $X_4$ are independently selected from the group consisting of $CR^{ii}$ and N, with the proviso that the number of nitrogen atoms in the ring is comprised from 0 to 2;

each $R^{ii}$ is independently selected from the group consisting of hydrogen, $C_{1-6}$alkyl, halo$C_{1-6}$alkyl, $C_{3-6}$cycloalkyl, heterocycloalkyl, aryl, heteroaryl, O-aryl, O-heteroaryl, $COR^{viii}$, $COOR^{viii}$, $CONHR^{viii}$, $CONR^{ix}R^x$, OH, O—$C_1$-6alkyl, O—$C_{3-6}$cycloalkyl, O-heterocycloalkyl, O-halo$C_{1-6}$alkyl, $C_{1-6}$alkyl-O—$C_{3-6}$alkyl, $C_{1-6}$alkyl-O—$C_{3-6}$cycloalkyl, $C_{1-6}$alkyl-O-heterocycloalkyl, CN, $NO_2$, $NR^{ix}R^x$, $N(R^x)COR^{viii}$, $N(R^x)COOR^{viii}$, $N(R^x)CONR^{ix}R^x$, $N(R^x)$ $SO_2R^{xi}$, $SO_2R^{xi}$, $SO_2NR^{ix}R^x$, halogen, and hydroxy-$C_{1-6}$alkyl;

$A_1$ and $A_4$ are $CR^{iii}R^{iv}$, $A_2$ and $A_3$ are selected from a bond and $CR^{iii}R^{iv}$;

$R^{iii}$ and $R^{iv}$ are independently selected from the group consisting of hydrogen, $C_{1-6}$alkyl, $C_{3-6}$cycloalkyl, heterocycloalkyl, halo$C_{1-6}$alkyl, $COR^{viii}$, $COOR^{viii}$, $CONHR^{viii}$, $CONR^{ix}R^x$, OH, O—$C_{1-6}$alkyl, $C_{1-6}$alkyl-O—$C_{1-6}$alkyl, CN, halogen, $NR^{ix}R^x$, $N(R^{ix})COR^{viii}$, or $R^{iii}$ and $R^{iv}$ form a $C_3$-$C_6$ cycloalkyl with the C to which they are linked;

or when $A_3$ is a bond, two groups $R^{iv}$ on $A_1$ and $A_2$, or on $A_1$ and $A_4$ are linked together to form a ring and thus the moiety

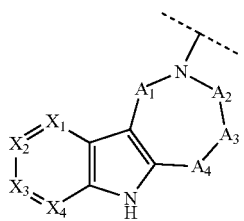

represents one of the structures selected from the group consisting of:

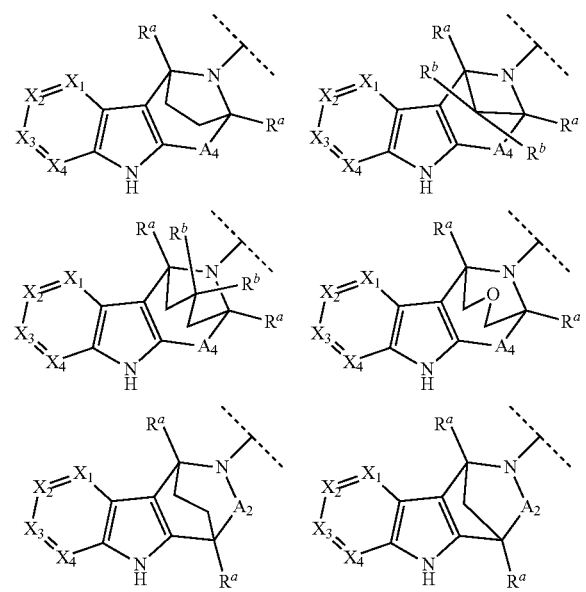

wherein $R^a$ and $R^b$ are independently selected from the group consisting of hydrogen, $C_{1-6}$alkyl, halogen, OH, O—$C_{1-6}$alkyl, $C_{1-6}$alkyl-O—$C_{1-6}$alkyl;

B is selected from the group consisting of:

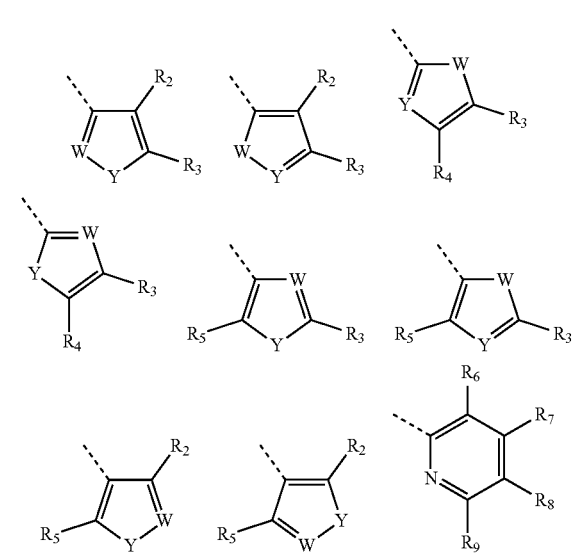

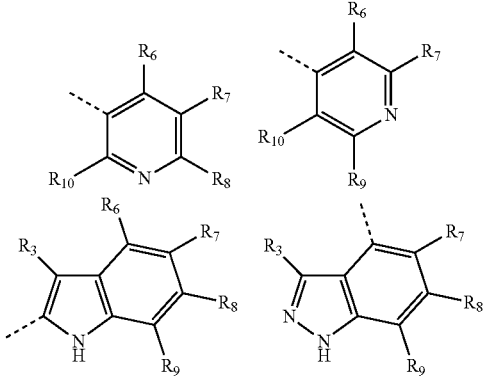

wherein
Y and W are independently selected from the group consisting of O, S, $CR^v$, $CR^vR^{vi}$, N, and $NR^{vii}$, wherein $R^v$ and $R^{vi}$ are selected form the group consisting of hydrogen, $C_{1-6}$alkyl, halo$C_{1-6}$alkyl, $C_{3-6}$cycloalkyl, heterocycloalkyl, aryl, heteroaryl, O—$C_{1-6}$alkyl, O—$C_{1-6}$alkylaryl, O—$C_{3-6}$cycloalkyl, O-heterocycloalkyl, O-halo$C_{1-6}$alkyl, $C_{1-6}$alkyl-O—$C_{1-6}$alkyl, $C_{1-6}$alkyl-O—$C_{3-6}$cycloalkyl, $C_{1-6}$ alkyl-O-heterocycloalkyl, $C_{1-6}$alkyl-O-aryl, $C_{1-6}$alkyl-O-heteroaryl, hydroxy-$C_{1-6}$alkyl, $COR^{viii}$, $COOR^{viii}$, $CONHR^{viii}$, and $CONR^{ix}R^x$;

$R^{vii}$ is selected form the group consisting of hydrogen, $C_{1-6}$alkyl, halo$C_{1-6}$alkyl, $C_{3-6}$cycloalkyl, heterocycloalkyl, aryl, heteroaryl, $C_{2-6}$alkyl-O—$C_{1-6}$alkyl, $C_{2-6}$alkyl-O—$C_{3-6}$cycloalkyl, $C_{2-6}$alkyl-O-heterocycloalkyl, $C_{2-6}$alkyl-O-aryl, and $C_{2-6}$alkyl-O-heteroaryl;

$R_2$, $R_3$, $R_4$, $R_5$, $R_6$, $R_7$, $R_8$, $R_9$ and $R_{10}$ are independently selected from the group consisting of hydrogen, $C_{1-6}$alkyl, halo$C_{1-6}$alkyl, $C_{3-6}$cycloalkyl, heterocycloalkyl, aryl, heteroaryl, $COR^{viii}$, $COOR^{viii}$, $CONHR^{vii}$, $CONR^{ix}R^x$, OH, O—$C_{1-6}$alkyl, O—$C_{1-6}$alkylaryl, O—$C_{3-6}$cycloalkyl, O-heterocycloalkyl, O-heteroaryl, O-aryl, O-halo$C_{1-6}$alkyl, $C_{1-6}$alkyl-O—$C_{1-6}$alkyl, $C_{1-6}$alkyl-O—$C_{3-6}$cycloalkyl, $C_{1-6}$alkyl-O-heterocycloalkyl, $C_{1-6}$alkyl-O-aryl, $C_{1-6}$alkyl-O-heteroaryl, hydroxy-$C_{1-6}$alkyl, CN, $NO_2$, $NR^{ix}R^x$, $N(R^x)COR^{viii}$, $N(R^x)COOR^{viii}$, $N(R^x)CONR^{ix}R^x$, $N(R^x)SO_2R^{xi}$, $SO_2R^{xi}$, $SO_2NR^{ix}R^x$, and halogen;

$R^{viii}$ is selected from the group consisting of hydrogen, $C_{1-6}$alkyl, halo$C_{1-6}$alkyl, $C_{3-6}$cycloalkyl, heterocycloalkyl, aryl, heteroaryl, $C_{1-6}$alkyl-O—$C_{1-6}$alkyl, and $C_{1-6}$alkyl-O-heterocycloalkyl;

$R^{ix}$ is selected from the group consisting of hydrogen, $C_{1-6}$alkyl, halo$C_{1-6}$alkyl, $C_{3-6}$cycloalkyl, heterocycloalkyl, aryl, and heteroaryl;

$R^x$ is selected from the group consisting of hydrogen, $C_{1-6}$alkyl, halo$C_{1-6}$alkyl, $C_{3-6}$cycloalkyl, heterocycloalkyl, aryl, heteroaryl, $C_{1-6}$alkyl-O—$C_{2-6}$alkyl, and hydroxy-$C_{2-6}$alkyl;

$R^{xi}$ is selected from the group consisting of $C_{1-6}$alkyl, halo$C_{1-6}$alkyl, $C_{3-6}$cycloalkyl, heterocycloalkyl, aryl, and heteroaryl.

In one embodiment of the invention, Z is C=O.
According to a further embodiment, $X_1$, $X_2$, $X_3$ and $X_4$ are $CR^{ii}$.
According to a further embodiment, each $R^{ii}$ is independently selected from the group consisting of hydrogen, $C_{1-6}$alkyl, halo$C_{1-6}$alkyl, $C_{3-6}$cycloalkyl, heterocycloalkyl, $COR^{viii}$, $COOR^{viii}$, $CONHR^{viii}$, $CONR^{ix}R^x$, OH, O—

$C_{1-6}$alkyl, O—$C_{3-6}$cycloalkyl, O-heterocycloalkyl, O-halo$C_{1-6}$alkyl, $C_{1-6}$alkyl-O—$C_{1-6}$alkyl, $C_{1-6}$alkyl-O—$C_{3-6}$cycloalkyl, $C_{1-6}$ alkyl-O-heterocycloalkyl, CN, $NO_2$, $NR^{ix}R^x$, $SO_2R^{xi}$, $SO_2NR^{ix}R^x$, halogen, and hydroxy-$C_{1-6}$alkyl.

According to a further embodiment, $R^{iii}$ and $R^{iv}$ are independently selected from the group consisting of hydrogen, $C_{1-6}$alkyl, $C_{3-6}$cycloalkyl, heterocycloalkyl, halo$C_{1-6}$alkyl, $COR^{viii}$, $COOR^{viii}$, $CONHR^{viii}$, $CONR^{ix}R^x$, OH, O—$C_{1-6}$alkyl, $C_{1-6}$alkyl-O—$C_{1-6}$alkyl, CN, halogen.

Alternatively, $R^{iii}$ and $R^{iv}$ are independently selected from the group consisting of hydrogen and $C_{1-6}$alkyl or, when $A_3$ is a bond, two groups $R^{iv}$ on $A_1$ and $A_2$, or on $A_1$ and $A_4$ are linked together to form a ring and thus the moiety

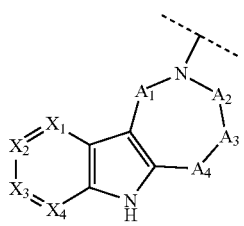

represents:

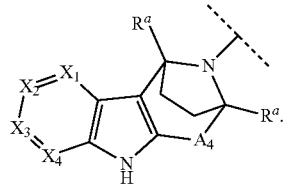

In a further embodiment, $R^{iii}$ and $R^{iv}$ are independently selected from the group consisting of hydrogen and methyl.

Compounds of Formula (Ib) as disclosed above may also be effective for the treatment of patients with other protein misfolding diseases. In this respect, other, structurally different CFTR correctors were found to rescue proteins (AVPR2, HCNH2, and ABCC8) with mutations causing trafficking defects (Sampson et al., *Orphanet J Rare Dis* 8:11, 2013). The compounds of Formula (Ib) may be indicated in particular for ABC proteins that share with CFTR a similar structure, particularly at the level of nucleotide-binding domains (Rudashevskaya et al., *Drug Discov Today Technol* 12:e87-94, 2014). A list of ABC proteins with trafficking defects and associated diseases that could benefit from CFTR modulators includes: ABCA1 (Tangier disease), ABCA3 (fatal surfactant deficiency), ABCA4 (Stargardt disease), ABCB4 (progressive familial intrahepatic cholestasis type 3), ABCB11 (progressive familial intrahepatic cholestasis type 2), ABCC2 (Dubin-Johnson syndrome), ABCC8 (hyperinsulinemic hypoglycemia of infancy) and ABCG2 (gout).

According to an aspect of the present invention, compounds of Formula (Ib) as disclosed above or the pharmaceutical composition thereof can be used in the treatment of a disease selected from the group consisting of cystic fibrosis, chronic obstructive pulmonary disease, chronic constipation, and dry eye syndrome, preferably cystic fibrosis.

In particular, the following compounds can be used:

| | |
|---|---|
| 001 | (6-Dimethylamino-1H-indol-2-yl)-(1,3,4,5-tetrahydropyrido[4,3-b]indol-2-yl)-methanone |
| 002 | (1-Phenyl-1H-pyrazol-4-yl)-(1,3,4,5-tetrahydropyrido[4,3-b]indol-2-yl)-methanone |
| 003 | (8-Methoxy-1,3,4,5-tetrahydro-pyrido[4,3-b]indol-2-yl)-(5-trifluoromethyl-1H-pyrazol-3-yl)-methanone |
| 004 | 1,3,4,5-tetrahydropyrido[4,3-b]indol-2-yl-[5-(trifluoromethyl)-1H-pyrazol-3-yl]methanone |
| 005 | (8-methyl-1,3,4,5-tetrahydropyrido[4,3-b]indol-2-yl)-[5-(trifluoromethyl)-1H-pyrazol-3-yl]methanone |
| 006 | (5-methyl-1H-pyrazol-3-yl)-(8-methyl-1,3,4,5-tetrahydropyrido[4,3-b]indol-2-yl)methanone |
| 007 | (5-isopropyl-1H-pyrazol-3-yl)-(8-methyl-1,3,4,5-tetrahydropyrido[4,3-b]indol-2-yl)methanone |
| 008 | (8-methyl-1,3,4,5-tetrahydropyrido[4,3-b]indol-2-yl)-(1H-pyrazol-3-yl)methone |
| 009 | [6-(dimethylamino)-1H-indol-2-yl]-(8-methyl-1,3,4,5-tetrahydropyrido[4,3-b]indol-2-yl)methanone |
| 010 | 1H-indol-2-yl-(8-methyl-1,3,4,5-tetrahydropyrido[4,3-b]indol-2-yl)methanone |
| 011 | (8-methyl-1,3,4,5-tetrahydropyrido[4,3-b]indol-2-yl)-[2-(trifluoromethyl)-1H-imidazol-4-yl]methanone |
| 012 | (3,5-dimethyl-1H-pyrazol-4-yl)-(8-methyl-1,3,4,5-tetrahydropyrido[4,3-b]indol-2-yl)methanone |
| 013 | (8-methyl-1,3,4,5-tetrahydropyrido[4,3-b]indol-2-yl)-(5-phenyl-1H-pyrazol-3-yl)methanone |
| 014 | (8-methyl-1,3,4,5-tetrahydropyrido[4,3-b]indol-2-yl)-(1-phenylpyrazol-4-yl)methanone |
| 015 | (5-isopropyl-1H-pyrazol-3-yl)-(8-methoxy-1,3,4,5-tetrahydropyrido[4,3-b]indol-2-yl)methanone |
| 016 | (8-methoxy-1,3,4,5-tetrahydropyrido[4,3-b]indol-2-yl)-(5-methyl-1H-pyrazol-3-yl)methanone |
| 017 | (8-methoxy-1,3,4,5-tetrahydropyrido[4,3-b]indol-2-yl)-(1-phenylpyrazol-4-yl)methanone |
| 018 | (8-methyl-1,3,4,5-tetrahydropyrido[4,3-b]indol-2-yl)-[1-methyl-5-(trifluoromethyl)pyrazol-3-yl]methanone |
| 019 | (5-isopropyl-1H-pyrazol-3-yl)-(1,3,4,5-tetrahydropyrido[4,3-b]indol-2-yl)methanone |
| 021 | [6-(dimethylamino)-1H-indol-2-yl]-(8-methoxy-1,3,4,5-tetrahydropyrido[4,3-b]indol-2-yl)methanone |
| 022 | 2-(5-bromo-2-furoyl)-8-methoxy-2,3,4,5-tetrahydro-1H-pyrido[4,3-b]indole |
| 023 | (5-bromo-2-furyl)-(8-methyl-1,3,4,5-tetrahydropyrido[4,3-b]indol-2-yl)methanone |
| 024 | (8-methyl-1,3,4,5-tetrahydropyrido[4,3-b]indol-2-yl)-[5-(trifluoromethyl)-2-furyl]methanone |
| 025 | (4-bromo-2-furyl)-(8-methyl-1,3,4,5-tetrahydropyrido[4,3-b]indol-2-yl)methanone |
| 026 | (8-methoxy-1,3,4,5-tetrahydropyrido[4,3-b]indol-2-yl)-(1H-pyrazol-3-yl)methanone |
| 027 | (8-methoxy-1,3,4,5-tetrahydropyrido[4,3-b]indol-2-yl)-(5-phenyl-1H-pyrazol-3-yl)methanone |
| 028 | (8-methoxy-1,3,4,5-tetrahydropyrido[4,3-b]indol-2-yl)-[2-(trifluoromethyl)-1H-imidazol-4-yl]methanone |
| 029 | (5-bromo-2-furyl)-(1,3,4,5-tetrahydropyrido[4,3-b]indol-2-yl)methanone |
| 030 | 2-furyl-(8-methyl-1,3,4,5-tetrahydropyrido[4,3-b]indol-2-yl)methanone |
| 031 | (5-tert-butyl-1H-pyrazol-3-yl)-(8-methyl-1,3,4,5-tetrahydropyrido[4,3-b]indol-2-yl)methanone |
| 032 | 1H-indol-2-yl(1,3,4,5-tetrahydropyrido[4,3-b]indol-2-yl)methanone |
| 033 | (5-cyclopropyl-1H-pyrazol-3-yl)-(8-methyl-1,3,4,5-tetrahydropyrido[4,3-b]indol-2-yl)methanone |
| 034 | (8-methyl-1,3,4,5-tetrahydropyrido[4,3-b]indol-2-yl)-[3-(trifluoromethyl)-1H-pyrazol-4-yl]methanone |
| 035 | (8-methyl-1,3,4,5-tetrahydropyrido[4,3-b]indol-2-yl)-[5-(trifluoromethyl)-2-pyridyl]methanone |
| 036 | (8-methyl-1,3,4,5-tetrahydropyrido[4,3-b]indol-2-yl)-[6-(trifluoromethyl)-1H-indol-2-yl]methanone |
| 037 | (8-isopropyl-1,3,4,5-tetrahydropyrido[4,3-b]indol-2-yl)-[5-(trifluoromethyl)-1H-pyrazol-3-yl]methanone |
| 038 | (6-methyl-1,3,4,5-tetrahydropyrido[4,3-b]indol-2-yl)-[5-(trifluoromethyl)-1H-pyrazol-3-yl]methanone |

-continued

| | |
|---|---|
| 039 | (8-fluoro-1,3,4,5-tetrahydropyrido[4,3-b]indol-2-yl)-[5-(trifluoromethyl)-1H-pyrazol-3-yl]methanone |
| 040 | (2-methyl-5,6,7,8,9,10-hexahydro-7,10-epiminocyclohepta[b]indol-11-yl) (5-(trifluoromethyl)-1H-pyrazol-3-yl)methanone |
| 041 | (1H-indol-2-yl) (2-methyl-5,6,7,8,9,10-hexahydro-7,10-epiminocyclohepta[b]indol-11-yl)methanone |
| 042 | (5-bromofuran-2-yl) (2-methyl-5,6,7,8,9,10-hexahydro-7,10-epiminocyclohepta[b]indol-11-yl)methanone |
| 043 | (8-methyl-1,3,4,5-tetrahydropyrido[4,3-b]indol-2-yl)-[6-(trifluoromethyl)-2-pyridyl]methanone |
| 044 | (6-fluoro-9-methyl-1,3,4,5-tetrahydropyrido[4,3-b]indol-2-yl)-[5-(trifluoromethyl)-1H-pyrazol-3-yl]methanone |
| 045 | [8-(trifluoromethoxy)-1,3,4,5-tetrahydropyrido[4,3-b]indol-2-yl]-[5-(trifluoromethyl)-1H-pyrazol-3-yl]methanone |
| 046 | (8-bromo-1,3,4,5-tetrahydropyrido[4,3-b]indol-2-yl)-[5-(trifluoromethyl)-1H-pyrazol-3-yl]methanone |
| 047 | [5-(trifluoromethyl)-1H-pyrazol-3-yl]-(4,4,8-trimethyl-3,5-dihydro-1H-pyrido[4,3-b]indol-2-yl)methanone |
| 048 | [5-(trifluoromethyl)-1H-pyrazol-3-yl]-[8-(trifluoromethyl)-1,3,4,5-tetrahydropyrido[4,3-b]indol-2-yl]methanone |
| 049 | (6,8-dimethyl-1,3,4,5-tetrahydropyrido[4,3-b]indol-2-yl)-[5-(trifluoromethyl)-1H-pyrazol-3-yl]methanone |
| 050 | (6-fluoro-1,3,4,5-tetrahydropyrido[4,3-b]indol-2-yl)-[5-(trifluoromethyl)-1H-pyrazol-3-yl]methanone |
| 051 | (6-fluoro-8-methyl-1,3,4,5-tetrahydropyrido[4,3-b]-indol-2-yl)-[5-(trifluoromethyl)-1H-pyrazol-3-yl]methone |
| 052 | (8-methylsulfonyl-1,3,4,5-tetrahydropyrido[4,3-b]indol-2-yl)-[5-(trifluoromethyl)-1H-pyrazol-3-yl]methanone |
| 053 | (4-fluoro-2-methyl-5,6,7,8,9,10-hexahydro-7,10-epiminocyclohepta[b]indol-11-yl) (5-(trifluoromethyl)-1H-pyrazol-3-yl)methanone |
| 054 | (9-fluoro-6-methyl-1,3,4,5-tetrahydropyrido[4,3-b]indol-2-yl)-[5-(trifluoromethyl)-1H-pyrazol-3-yl]methanone |
| 055 | (4-fluoro-1-methyl-5,6,7,8,9,10-hexahydro-7,10-epiminocyclohepta[b]indol-11-yl) (5-(trifluoromethyl)-1H-pyrazol-3-yl)methanone |
| 056 | (6,9-dimethyl-1,3,4,5-tetrahydropyrido[4,3-b]indol-2-yl)-[5-(trifluoromethyl)-1H-pyrazol-3-yl]methanone |
| 057 | 2-[5-(trifluoromethyl)-1H-pyrazole-3-carbonyl]-1,3,4,5-tetrahydropyrido[4,3-b]indole-8-carbonitrile |
| 058 | (9-methyl-1,3,4,5-tetrahydropyrido[4,3-b]indol-2-yl)-[5-(trifluoromethyl)-1H-pyrazol-3-yl]methanone |
| 059 | (7-methyl-1,3,4,5-tetrahydropyrido[4,3-b]indol-2-yl)-[5-(trifluoromethyl)-1H-pyrazol-3-yl]methanone |
| 060 | (6,8-difluoro-1,3,4,5-tetrahydropyrido[4,3-b]indol-2-yl)-[5-(trifluoromethyl)-1H-pyrazol-3-yl]methanone |
| 061 | (6-bromo-9-methyl-1,3,4,5-tetrahydropyrido[4,3-b]indol-2-yl)-[5-(trifluoromethyl)-1H-pyrazol-3-yl]methanone |
| 063 | (6-fluoro-9-methyl-1,3,4,5-tetrahydropyrido[4,3-b]indol-2-yl)-(1H-indol-2-yl)methanone |
| 077 | (6-fluoro-4,4,9-trimethyl-3,5-dihydro-1H-pyrido[4,3-b]indol-2-yl)-[5-(trifluoromethyl)-1H-pyrazol-3-yl]methanone |
| 079 | (7R,10S)- or (7S,10R)-(4-fluoro-1-methyl-5,6,7,8,9,10-hexahydro-7,10-epiminocyclohepta[b]indol-11-yl) (5-(trifluoromethyl)-1H-pyrazol-3-yl)methanone |
| 080 | (7S,10R)- or (7R,10S)-4-fluoro-1-methyl-5,6,7,8,9,10-hexahydro-7,10-epiminocyclohepta[b]indol-11-yl) (5-(trifluoromethyl)-1H-pyrazol-3-yl)methanone |
| 081 | (6,9-difluoro-1,3,4,5-tetrahydropyrido[4,3-b]indol-2-yl)-[5-(trifluoromethyl)-1H-pyrazol-3-yl]methanone |
| 082 | [6-fluoro-8-(trifluoromethyl)-1,3,4,5-tetrahydropyrido[4,3-b]indol-2-yl]-[5-(trifluoromethyl)-1H-pyrazol-3-yl]methanone |
| 086 | (6-fluoro-8-methoxy-1,3,4,5-tetrahydropyrido[4,3-b]indol-2-yl)-[5-(trifluoromethyl)-1H-pyrazol-3-yl]methanone |
| 087 | [6-fluoro-9-(trifluoromethyl)-1,3,4,5-tetrahydropyrido[4,3-b]indol-2-yl]-[5-(trifluoromethyl)-1H-pyrazol-3-yl]methanone |
| 088 | (6-chloro-8-methoxy-1,3,4,5-tetrahydropyrido[4,3-b]indol-2-yl)-[5-(trifluoromethyl)-1H-pyrazol-3-yl]methanone |
| 092 | (6-fluoro-9-methyl-1,3,4,5-tetrahydropyrido[4,3-b]indol-2-yl)-[2-(trifluoromethyl)thiazol-4-yl]methanone |
| 093 | (4-bromo-3-pyridyl)-(6-fluoro-9-methyl-1,3,4,5-tetrahydropyrido[4,3-b]indol-2-yl)methanone |
| 094 | (3-bromo-4-pyridyl)-(6-fluoro-9-methyl-1,3,4,5-tetrahydropyrido[4,3-b]indol-2-yl)methanone |
| 095 | (5-bromo-2-methoxy-3-pyridyl)-(6-fluoro-9-methyl-1,3,4,5-tetrahydropyrido[4,3-b]indol-2-yl)methanone |
| 096 | (6-bromo-1H-indazol-4-yl)-(6-fluoro-9-methyl-1,3,4,5-tetrahydropyrido[4,3-b]indol-2-yl)methanone |
| 097 | [2-amino-4-(trifluoromethyl)thiazol-5-yl]-(6-fluoro-9-methyl-1,3,4,5-tetrahydropyrido[4,3-b]indol-2-yl)methanone |
| 098 | [3-(4-bromophenyl)-5-methyl-isoxazol-4-yl]-(6-fluoro-9-methyl-1,3,4,5-tetrahydropyrido[4,3-b]indol-2-yl)methanone |
| 104 | 3-(6-fluoro-9-methyl-1,3,4,5-tetrahydropyrido[4,3-b]indole-2-carbonyl)-1H-pyrazole-5-carboxylic acid |
| 105 | rac-(6-fluoro-3,9-dimethyl-1,3,4,5-tetrahydropyrido[4,3-b]indol-2-yl)-[5-(trifluoromethyl)-1H-pyrazol-3-yl]methanone |
| 106 | rac-(6-fluoro-1,9-dimethyl-1,3,4,5-tetrahydropyrido[4,3-b]indol-2-yl)-[5-(trifluoromethyl)-1H-pyrazol-3-yl]methanone |
| 107 | 8-methoxy-N-(5-methyl-1H-pyrazol-3-yl)-1,3,4,5-tetrahydropyrido[4,3-b]indole-2-carboxamide |
| 108 | (R)-(6-fluoro-3,9-dimethyl-1,3,4,5-tetrahydropyrido[4,3-b]indol-2-yl)-[5-(trifluoromethyl)-1H-pyrazol-3-yl]methanone |
| 109 | (S)-(6-fluoro-3,9-dimethyl-1,3,4,5-tetrahydropyrido[4,3-b]indol-2-yl)-[5-(trifluoromethyl)-1H-pyrazol-3-yl]methanone |
| 112 | (6-fluoro-3,3,9-trimethyl-4,5-dihydro-1H-pyrido[4,3-b]indol-2-yl)-[5-(trifluoromethyl)-1H-pyrazol-3-yl]methanone |
| 113 | [(S)-6,9-difluoro-3-methyl-1,3,4,5-tetrahydropyrido[4,3-b]indol-2-yl]-[5-(trifluoromethyl)-1H-pyrazol-3-yl]methanone |
| 114 | [(R)-6-fluoro-3,9-dimethyl-1,3,4,5-tetrahydropyrido[4,3-b]indol-2-yl]-(1H-indol-2-yl)methanone |
| 115 | [(S)-8-methoxy-6-fluoro-3-methyl-1,3,4,5-tetrahydropyrido[4,3-b]indol-2-yl]-[5-(trifluoromethyl)-1H-pyrazol-3-yl]methanone |
| 116 | rac-(6-fluoro-1-methyl-8-methoxy-1,3,4,5-tetrahydropyrido[4,3-b]indol-2-yl)-(5-(trifluoromethyl)-1H-pyrazol-3-yl)methanone |
| 117 | [(R)-8-methoxy-6-fluoro-3-methyl-1,3,4,5-tetrahydropyrido[4,3-b]indol-2-yl]-[5-(trifluoromethyl)-1H-pyrazol-3-yl]methanone |
| 119 | (8-methoxy-1,3,4,5-tetrahydropyrido[4,3-b]indol-2-yl)-(3-methyl-1-propyl-pyrazol-4-yl)methanone |
| 120 | [2-(dimethylamino)-4-pyridyl]-(8-methoxy-1,3,4,5-tetrahydropyrido[4,3-b]indol-2-yl)methanone |
| 121 | (6-fluoro-3-isopropyl-8-methoxy-1,3,4,5-tetrahydropyrido[4,3-b]indol-2-yl)-(5-methyl-1H-pyrazol-3-yl)methanone |
| 122 | (6,9-difluoro-8-methoxy-spiro[4,5-dihydro-3H-pyrido[4,3-b]indole-1,1'-cyclopropane]-2-yl)-(5-methyl-1H-pyrazol-3-yl)methanone |
| 123 | (6,9-difluoro-1,3-dimethyl-1,3,4,5-tetrahydropyrido[4,3-b]indol-2-yl)-(5-methyl-1H-pyrazol-3-yl)methanone |
| 124 | (6,9-difluoro-8-methoxy-spiro[4,5-dihydro-1H-pyrido[4,3-b]indole-3,1'-cyclopropane]-2-yl)-(5-methyl-1H-pyrazol-3-yl)methanone |
| 125 | [6-(dimethylamino)-1H-indol-2-yl]-(8-methylspiro[3,5-dihydro-1H-pyrido[4,3-b]indole-4,1'-cyclopropane]-2-yl)methanone |

| | |
|---|---|
| 126 | (4-ethyl-6-fluoro-9-methyl-1,3,4,5-tetrahydropyrido[4,3-b]indol-2-yl)-(5-methyl-1H-pyrazol-3-yl)methanone |
| 127 | 6-fluoro-9-methyl-2-(5-methyl-1H-pyrazole-3-carbonyl)-1,3,4,5-tetrahydropyrido[4,3-b]indole-3-carboxylic acid |
| 128 | [6-(dimethylamino)-1H-indol-2-yl]-[8-methyl-1-(trifluoromethyl)-1,3,4,5-tetrahydropyrido[4,3-b]indol-2-yl]methanone |
| 129 | (6-fluoro-8-methoxy-1,4-dimethyl-1,3,4,5-tetrahydropyrido[4,3-b]indol-2-yl)-(5-methyl-1H-pyrazol-3-yl)methanone |
| 130 | (6-fluoro-8-methoxy-9-methyl-1,3,4,5-tetrahydropyrido[4,3-b]indol-2-yl)-(5-methyl-1H-pyrazol-3-yl)methanone |
| 131 | 6-fluoro-4,9-dimethyl-2-(5-methyl-1H-pyrazole-3-carbonyl)-3,5-dihydro-1H-pyrido[4,3-b]indole-4-carboxylic acid |
| 132 | (4,4-difluoro-8-methoxy-3,5-dihydro-1H-pyrido[4,3-b]indol-2-yl)-(5-methyl-1H-pyrazol-3-yl)methanone |
| 133 | (3,6-dimethyl-4,8,10-triazatricyclo[7.4.0.02,7]trideca-1(9),2(7),10,12-tetraen-4-yl)-(5-methyl-1H-pyrazol-3-yl)methanone |
| 134 | (6,6-dimethyl-4,8,12-triazatricyclo[7.4.0.02,7]trideca-1(9),2(7),10,12-tetraen-4-yl)-(5-methyl-1H-pyrazol-3-yl)methanone |
| 135 | 2-(5-bromofuran-2-carbonyl)-8-methoxy-1,3,4,5-tetrahydropyrido[4,3-b]indole-4-carboxylic acid |

In the following, the present invention shall be illustrated by means of some examples, which are not construed to be viewed as limiting the scope of the invention.

The following abbreviations are hereinafter used in the accompanying examples: Acetic acid (AcOH), aryl (Ar), Apparent triplet (app-t), Apparent doublet of triplet (app-dt), Apparent doublet (app-d), aqueous (aq.), atmospheres (atm), broad signal (bs), carbon nuclear magnetic resonance spectroscopy ($^{13}$C-NMR), doublet (d), dichloromethane (DCM), doublet of doublet (dd), doublet of doublet of triplets (ddt), ethyldiisopropylamine (DIPEA), doublet of quartet (dq), N,N-dimethylformamide (DMF), dimethyl sulfoxide (DMSO), Hexadeuterodimethyl sulfoxide (DMSO-d$_6$), doublet of triplet (dt), N-(3-dimethylamino propyl)-N'-ethylcarbodiimide hydrochloride (EDC-HCl), half maximal effective concentration (EC50), equivalents (equiv. or eq.), enantiomeric excess (e.e.) electrospray ionization (ESI), diethyl ether (Et$_2$O), ethanol (EtOH) ethyl acetate (EtOAc), hour (h), proton nuclear magnetic resonance spectroscopy ($^1$H NMR), 1-[bis-(dimethylamino)methylene]-1H-1,2,3-triazolo[4,5-b]pyridinium 3-oxid hexafluorophosphate (HATU), high performance liquid chromatography (HPLC), hertz (Hz), hydrochloridric acid (HCl), coupling constant (J), liter (L), molarity (M), multiplet (m), methyl (Me), acetonitrile (MeCN), methanol (MeOH), milligram (mg), megahertz (MHz), minutes (min), milliliter (mL), millimole (mmol), Mass Spectrometry (MS), molecular weight (mw), number of atoms or counterions (n), Sodium hydride (NaH), Sodium Hydroxide (NaOH), Sodium bicarbonate (NaHCO$_3$), Sodium carbonate (Na$_2$CO$_3$), Sodium sulphate (Na$_2$SO$_4$), Ammonium Chloride (NH$_4$Cl), Ammonium Formiate (NH$_4$HCO$_2$), not determined (nd), nanomolar (nM), Nuclear Magnetic Resonace (NMR), nuclear Overhauser enhancement spectroscopy (NOESY), nucleophile (Nu), palladium on charcoal (Pd/C), protecting group (Pg), phenyl (Ph), parts per million (ppm), iso-propyl (i-Pr), quartet (q), substituent (R), racemic (rac), room temperature (rt), singlet (s), temperature (T), triplet or time (t), retention time (t$_R$), triethylamine (Et$_3$N), tetrahydrofuran (THF), thin-layer chromatography (TLC), Ultra-Performance Liquid Chromatography-Mass Spectroscopy (UPLC-MS), anionic ligand, halide, substituent, or number (X), chemical shift (δ), microliter (μL), Micromolar (μM).

Chemicals, Materials and Methods

Solvents and reagents were obtained from commercial suppliers and were used without further purification.

Automated column chromatography purifications were performed on Teledyne ISCO apparatus (CombiFlash® Rf) with pre-packed silica gel columns of different sizes (Redisep). NMR experiments were run on a Bruker Avance III 400 system (400.13 MHz for $^1$H, and 100.62 MHz for $^{13}$C), equipped with a BBI probe and Z-gradients and Bruker FT NMR Avance III 600 MHz spectrometer equipped with a 5 mm CryoProbe™ QCI $^1$H/$^{19}$F-$^{13}$C/$^{15}$N-D quadruple resonance, a shielded z-gradient coil and the automatic sample changer SampleJet™ NMR system (600 MHz for $^1$H, 151 MHz for $^{13}$C and 565 MHz for $^{19}$F). Chemical shifts for $^1$H and $^{13}$C spectra were recorded in parts per million using the residual non-deuterated solvent as the internal standard (for CDCl$_3$: 7.26 ppm, $^1$H and 77.16 ppm, $^{13}$C; for DMSO-d$_6$: 2.50 ppm, $^1$H; 39.52 ppm, $^{13}$C, for D$_2$O: TSP as internal standard 0.00 ppm).

The analyses by UPLC/MS were run on a Waters ACQUITY UPLC/MS system consisting of a SQD (Single Quadrupole Detector) Mass Spectrometer equipped with an Electrospray Ionization interface and a Photodiode Array Detector. The PDA range was 210-400 nm. The analyses were performed on either an ACQUITY UPLC HSS T3 C$_{18}$ column (50×2.1 mmID, particle size 1.8 μm) with a VanGuard HSS T3 C$_{18}$ pre-column (5×2.1 mmID, particle size 1.8 μm) (Log D<1) or an ACQUITY UPLC BEH C$_{18}$ column (50×2.1 mmID, particle size 1.7 μm) with a VanGuard BEH C$_{18}$ pre-column (5×2.1 mmID, particle size 1.7 μm) (Log D>1).

The mobile phase was 10 mM NH$_4$OAc in H$_2$O at pH 5 adjusted with AcOH (A) and 10 mM NH$_4$OAc in MeCN—H$_2$O (95:5) at pH 5 (B).

Electrospray ionization in positive and negative mode was applied in the mass scan range 100-650 Da or 150-750 Da.

Analyses were performed either with "Polar method", "Generic method" and "Apolar Method" herein reported:

Method A:
Column: Waters ACQUITY UPLC BEH C$_{18}$, 1.7 μm, 50×2.1 mmID
Pre-column: VanGuard BEH C$_{18}$, 1.7 μm, 5×2.1 mmID
Linear gradient: 0-0.2 min: 5% B, 0.2-2.7 min: 5-95% B, 2.7-2.8 min: 95-100% B, 2.8-3.0 min: 100% B
Flow rate: 0.5 mL/min Method B:
Column: Waters ACQUITY UPLC HSS T3 C$_{18}$, 1.8 μm, 50×2.1 mmID
Pre-column: VanGuard HSS T3 C$_{18}$, 1.8 μm, 5×2.1 mmID
Linear gradient: 0-0.2 min: 0% B, 0.2-2.7 min: 0-50% B, 2.7-2.8 min: 50-100% B, 2.8-3.0 min: 100% B
Flow rate: 0.5 mL/min Method C:
Column: Waters ACQUITY UPLC BEH C$_{18}$, 1.7 μm, 50×2.1 mmID
Pre-column: VanGuard BEH C$_{18}$, 1.7 μm, 5×2.1 mmID
Gradient: 0-0.2 min: 50% B, 0.2-2.7 min: 50-100% B, 2.7-3.0 min: 100% B
Flow rate: 0.5 mL/min The chiral separations by HPLC were run on a Waters Alliance HPLC instrument consisting of an e2695 Separation Module and a 2998 Photodiode Array Detector. The PDA range was 210-400 nm. The analyses were performed in isocratic mode on a Daicel ChiralCel OD-H column (250×4.6 mmID, particle size 5 μm) at 25° C.

PREPARATIONS AND EXAMPLES

The compounds exemplified in this invention may be prepared from readily available starting materials using the following general methods and procedures for example exemplified in Michael B. Smith—March's Advanced Organic Chemistry: reactions, mechanisms, and structure—7th Edition, John Wiley & Sons Inc., 2013.

It is well known to one of ordinary skill in the art that transformation of a chemical function into another may require that one or more reactive centers in the compound containing this function be protected in order to avoid undesired side reactions. Protection of such reactive centers, and subsequent de-protection at the end of the synthetic transformations, can be accomplished following standard procedures described, for instance, in Peter G. M. Wuts—Green's Protective Groups in Organic Synthesis, Fifth Edition, John Wiley & Sons Inc., 2014.

It will be appreciated that where typical or preferred experimental conditions (i.e. reaction temperatures, time, moles of reagents, solvents, etc.) are given, other experimental conditions can also be used unless otherwise stated. Optimum reaction conditions may vary with the particular reactants or solvents used, but such conditions can be determined by the person skilled in the art, using routine optimization procedures.

The synthesis of a compound of Formula (Ia) and (Ib), according to the synthetic processes described below, can be conducted in a stepwise manner, whereby each intermediate is isolated and purified by standard purification techniques such as, for example, column chromatography, before carrying out the subsequent reaction. Alternatively, two or more steps of the synthetic sequence can be carried out in a so-called "one-pot" procedure, as known in the art, whereby only the compound resulting from the two or more steps is isolated and purified.

The compounds of (Ia) and (Ib), prepared with the methods described herein below, may be treated or purified by conventional techniques or means for example by filtration, distillation, chromatography, recrystallization and combination thereof.

The salts of compounds of (Ia) and (Ib) may be prepared by reacting a basic compound with the desired acid in solution, or by reacting an acidic compound with the desired base in solution.

With the aim of better illustrating the present invention, the syntheses of example compounds reported in Table 1 are provided.

GENERAL PROCEDURES

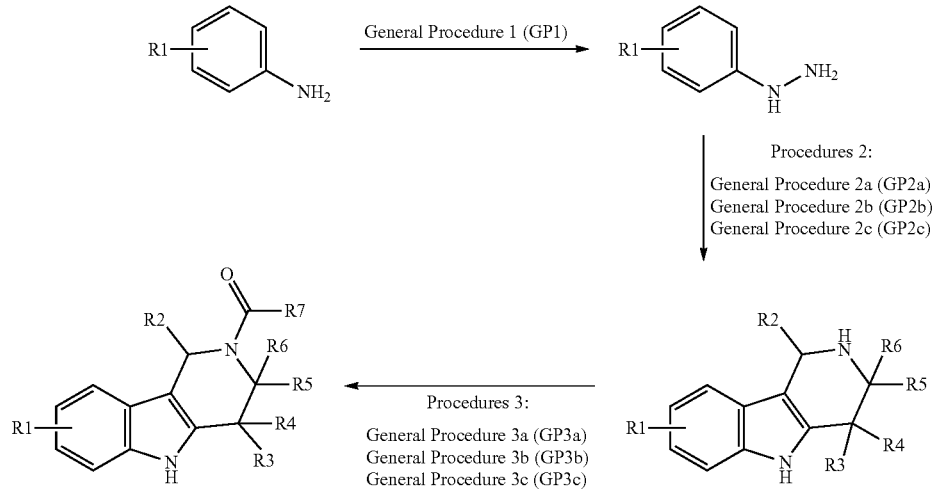

General Procedure 1 (GP1)

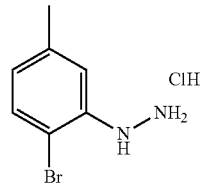

[Int-1.1] (2-Bromo-5-methyl-phenyl)hydrazine hydrochloride: 2-Bromo-5-methyl-aniline (1.5 g, 1 eq., 8.15 mmol) was added at 0° C. to a vigorously stirred aqueous solution of HCl 36% (2.9 mL). To the so-obtained suspension, a solution of sodium nitrite (1.1 g, 1.9 eq., 15.8 mmol) in water (1.8 mL) and a solution of tin chloride (4.5 g, 2.4 eq., 19.8 mmol) in HCl 6M (8.2 mL) were added. The reaction mixture was stirred at room temperature for 24 h, and basified with NaOH 12 M. The aqueous phase was extracted with Et$_2$O (3×20 mL); the combined organic extracts were dried over Na$_2$SO$_4$, and filtered. To obtain the hydrazine hydrochloride a saturated solution of HCl in Et$_2$O was added. The salt was filtered and washed with Et$_2$O, obtaining a white solid (1.7 g, 89%): $^1$H NMR (400 MHz, DMSO-d$_6$): δ 10.16 (bs, 3H), 7.80 (bs, 1H), 7.44 (d, J=8.0 Hz, 1H), 6.93 (d, J=1.8 Hz, 1H), 6.76 (dd, J=8.1, 1.8 Hz, 1H), 2.28 (s, 3H). UPLC-MS: t$_R$=1.81 min (method A); MS (ESI) m/z calcd for C$_7$H10BrN$_2$ (M+H)$^+$: 201.0, found: 201.2.

Procedures 2

General Procedure 2a (GP2a)

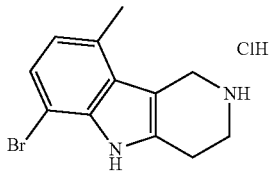

[Int-2 0.1] 6-Bromo-9-methyl-2, 3,4,5-tetrahydro-1H-pyrido [4,3-b]indole hydrochloride: To a solution of [Int-1.1] (1 g, 1 eq., 4.21 mmol) and tert-butyl 4-oxopiperidine-1-carboxylate (0.8 g, 1 eq., 4.21 mmol) in EtOH (15 mL), HCl 36% (4 mL) was added. The reaction mixture was heated at 80° C. and stirred for 16 h. The suspension was filtered and washed with Et$_2$O to furnish the title compound as brown solid (0.6 g, 50%): $^1$H NMR (400 MHz, DMSO-d$_6$): δ 11.27 (s, 1H), 9.21 (bs, 2H), 7.17 (d, J=7.7 Hz, 1H), 6.72 (dd, J=7.7, 0.9 Hz, 1H), 4.55 (s, 2H), 3.44 (t, J=6.1 Hz, 2H), 3.04 (t, J=6.1 Hz, 2H), 2.50 (s, 3H). UPLC-MS: $t_R$=1.57 min (method A); MS (ESI) m/z calcd for C$_{12}$H$_{14}$BrN$_2$ (M+H)$^+$: 365.0.0, found: 265.3.

General Procedure 2b (GP2b)

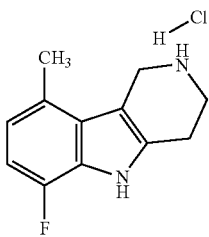

[Int-2 0.2] 6-Fluoro-9-methyl-2, 3,4,5-tetrahydro-1H-pyrido [4,3-b]indole hydrochloride: A solution of [Int-1.2] (0.5 g, 2.83 mmol) and tert-butyl 4-oxopiperidine-1-carboxylate (0.564 g, 2.83 mmol) in EtOH (5 mL) was stirred at room temperature, until the formation of hydrazone intermediate. 2,4,6-Trichloro-1,3,5-triazine (0.208 g, 1.13 mmol) was added and reaction mixture was heated to 90° C. for 8 h. The reaction mixture was cooled to room temperature and the obtained precipitate was filtered and washed with cold EtOH. The crude product was obtained as a light orange solid (0.65 g, 95%). UPLC-MS: $t_R$=1.31 min (method A); MS (ESI) m/z calcd for C$_{12}$H$_{14}$FN$_2$ (M+H)$^+$: 205.1, found: 205.8.

General Procedure 2c (GP2c)

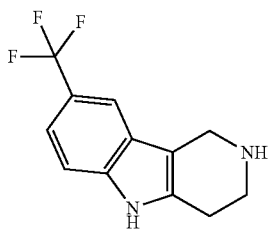 [SMILES: FC(F)(F)c1ccc2[nH]c3c(c2c1)CNCC3]

[Int-2.3] 8-(Trifluoromethyl)-2,3,4,5-tetrahydro-1H-pyrido [4,3-b]indole: 4-Trifluoromethylphenyl hydrazine (0.5 g, 2.84 mmol) and 4-oxopiperidine-1-carboxylate (0.4 g, 2.84 mmol) were dissolved in EtOH (15 mL) and the reaction mixture was stirred at room temperature for 30 min, until the complete formation of hydrazone. Solvent was removed under reduced pressure and the crude mixture was dissolved in AcOH (25 mL) following by addition of trifluoroborate diethyletherate (0.7 mL, 5.68 mmol). The reaction was stirred at 90° C. for 16 h. The solvent was removed and the crude mixture was poured into 2M aq.NaOH (15 mL) and extracted with DCM (2×10 mL), dried over Na$_2$SO$_4$, filtered and concentrated in vacuo to afford the crude product as brown solid, which was used in the next step without any further purification. $^1$H NMR (400 MHz, DMSO-d$_6$): δ 7.68 (s, 1H), 7.44 (d, J=8.4 Hz, 1H), 7.27 (d, J=8.6 Hz, 1H), 3.88 (d, J=4.9 Hz, 2H), 3.02 (q, J=5.5 Hz, 2H), 2.70 (t, J=5.7 Hz, 2H). UPLC-MS: $t_R$=1.59 min (method A); MS (ESI) m/z calcd for C$_{12}$H$_{12}$F$_3$N$_2$ (M+H)$^+$: 241.1, found: 242.1.

Procedures 3

General Procedure 3a (GP3a)

[6-(Dimethylamino)-1H-indol-2-yl]-(1,3,4,5-tetrahydropyrido [4,3-b] indol-2-yl) methanone: 6-(Dimethylamino)-1H-indole-2-carboxylic acid (0.02 g, 1 eq., 0.12 mmol), HATU (0.05 g, 1.1 eq., 0.13 mmol) and DIPEA (0.04 mL, 2 eq., 0.24 mmol) were dissolved in DMF (2 mL) and stirred at room temperature for 10 min. 2,3,4,5-Tetrahydro-1H-pyrido [4,3-b] indole (0.03 g, 1 eq., 0.12 mmol) was added and the reaction mixture was stirred at room temperature for 16 h. The reaction was quenched with 2M aq. HCl (10 mL) and the aqueous phase was extracted with EtOAc (2×10 mL). The combined extracts were washed sequentially with water (15 mL) and brine (15 mL), dried over Na$_2$SO$_4$, filtered and concentrated in vacuo to afford the crude product. The title compound was obtained after preparative LC-MS, as a white solid (0.01 g, 34%). $^1$H NMR (400 MHz, DMSO-d$_6$): δ 11.11 (s, 1H), 10.97 (s, 1H), 7.46 (dd, J=8.1, 4.8 Hz, 2H), 7.32 (d, J=8.0 Hz, 1H), 7.10-7.02 (m, 1H), 6.97 (t, J=7.5 Hz, 1H), 6.87 (s, 1H), 6.75 (dd, J=8.9, 2.3 Hz, 1H), 6.64 (d, J=2.2 Hz, 1H), 4.94 (s, 2H), 4.12 (d, J=5.9 Hz, 2H), 2.98 (s, 2H), 2.92 (s, 6H). UPLC-MS: $t_R$=2.27 min (method A); MS (ESI) m/z calcd for C$_{22}$H$_{23}$N$_4$O (M+H)$^+$: 359.2, found: 359.3.

General Procedure 3b (GP3b)

1,3,4,5-Tetrahydropyrido[4,3-b]indol-2-yl-[5-(trifluoromethyl)-1H-pyrazol-3-yl]methanone: To a solution of 5-(trifluoromethyl)-1H-pyrazole-3-carboxylic acid (20 mg, 0.12 mmol) in DCM (1 ml), DMF (cat.) and oxalyl chloride (20 µL, 0.24 mmol) were added at 0° C. under N$_2$ atmosphere, and the reaction mixture was stirred at room temperature for 30 min. The solvent was removed under reduced pressure. Toluene (3 mL) was added and solvent evaporated again. The obtained acyl chloride was added to a solution of 2,3,4,5-tetrahydro-1H-pyrido[4,3-b]indole (0.02 g, 1 eq., 0.12 mmol) and Et$_3$N (0.03 mL, 2 eq., 0.24 mmol) in DCM (2 mL) cooled to 0° C. The reaction mixture was stirred at room temperature for 16 h, and quenched with aq. 2M HCl (10 mL). The aqueous phase was extracted with DCM (2×10 mL, and the combined extracts were washed with water (15 mL), brine (15 mL), dried over Na$_2$SO$_4$, filtered and concentrated in vacuo to afford the crude product, which was purified by flash chromatography eluting with cyclohexane/ EtOAc (8:2) to give the pure title compound as white solid (0.02 g, 45%). $^1$H NMR (400 MHz, DMSO-d6): δ 14.39 (s, 1H), 10.99 (s, 1H), 7.54-7.40 (m, 1H), 7.37-7.17 (m, 2H), 7.11-6.87 (m, 2H), 4.86 (d, J=31.0 Hz, 2H), 4.20-3.73 (m, 2H), 2.95 (d, J=33.2 Hz, 2H). UPLC-MS: $t_R$=2.27 min (method A); MS (ESI) m/z calcd for $C_{16}H_{14}F_3N_4O$ (M+H)$^+$: 335.1, found: 335.3.

General Procedure 3c (GP3c)

(5-bromo-2-furyl)-(1,3,4,5-tetrahydropyrido[4,3-b]indol-2-yl)methanone: 5-Bromofuran-2-carboxylic acid (0.06 g, 1 eq., 0.32 mmol), 2,3,4,5-Tetrahydro-1H-pyrido[4,3-b]indole (0.06 g, 1 eq., 0.32 mmol), Et$_3$N (0.09 mL, 2 eq., 0.64 mmol) and EDC-HCl (0.07 g, 1.1 eq., 0.38 mmol) were dissolved in DCM (2 mL) and stirred at room temperature for 16 h. The reaction was quenched with aq. 2M HCl (10 mL) and the aqueous phase was extracted with EtOAc (2×10 mL). The combined extracts were washed with water (15 mL), brine (15 mL), dried over Na$_2$SO$_4$, filtered and concentrated in vacuo to afford the crude product, which was purified by flash chromatography eluting with DCM/EtOAc (0 to 20%) to give the pure title compound as white solid (0.02 g, 20%). $^1$H NMR (400 MHz, DMSO-d$_6$): δ 10.96 (s, 1H), 7.43 (d, J=7.7 Hz, 1H), 7.37-7.24 (m, 1H), 7.14 (d, J=3.5 Hz, 1H), 7.05 (ddd, J=8.2, 7.0, 1.2 Hz, 1H), 7.01-6.93 (m, 1H), 6.81 (d, J=3.5 Hz, 1H), 4.81 (bs, 2H), 3.99 (t, J=5.7 Hz, 2H), 2.94 (bs, 2H). UPLC-MS: $t_R$=2.17 min (method A); MS (ESI) m/z calcd for $C_{16}H_{14}BrN_2O_2$ (M+H)$^+$: 345.0, found: 345.6.

Synthesis of Substituted Phenyl-Hydrazines

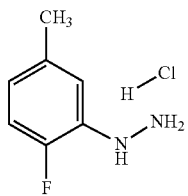

[Int-1.2] (2-Fluoro-5-methyl-phenyl)hydrazine hydrochloride: Following GP1, the title compound was obtained from 2-fluoro-5-methyl-aniline, as crude product as a light brown powder in a quantitative yield. $^1$H NMR (400 MHz, DMSO-d6): δ 10.02 (s, 3H), 8.81 (s, 1H), 6.97 (dd, J=8.6, 2.2 Hz, 1H), 6.91 (dd, J=12.0, 8.1 Hz, 1H), 6.50 (ddd, J=7.5, 4.6, 2.1 Hz, 1H), 2.23 (s, 3H). UPLC-MS: $t_R$=1.39 min (Method A); MS (ESI) m/z calcd for $C_7H_{10}FN_2$ (M+H)$^+$: 141.1, found: 141.3.

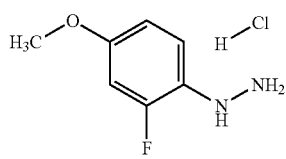

[Int-1.3] (2-Fluoro-4-methoxy-phenyl) hydrazine hydrochloride: Following GP1, the title compound was obtained from 2-fluoro-3-methoxy-aniline, as a light pink powder in 51% yield. UPLC-MS: $t_R$=1.42 min (Method A); MS (ESI) m/z calcd for $C_7H10FN_2O$ (M+H)$^+$: 157.1, found: 157.3.

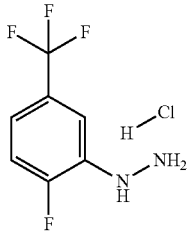

[Int-1.4] (2-Fluoro-5-(trifluoromethyl)phenyl)hydrazine hydrochloride: Following GP1, the title compound was obtained from 2-fluoro-5-(trifluoromethyl) aniline, as a light pink powder in 15% yield. $^1$H NMR (400 MHz, DMSO-d6): δ 10.49 (br s, 3H), 8.68 (s, 1H), 7.62 (dd, J=7.9, 2.2 Hz, 1H), 7.43 (dd, J=11.2, 8.5 Hz, 1H), 7.36-7.29 (m, 1H). UPLC-MS: $t_R$=1.37 min (Method A); MS (ESI) m/z calcd for $C_7H_7F_4N_2$ (M+H)$^+$: 195.0, found: 195.2

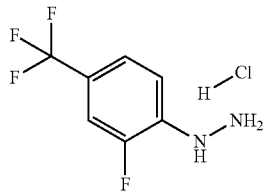

[Int-1.5] (2-Fluoro-4-(trifluoromethyl)phenyl) hydrazine hydrochloride: Following GP1, the title compound was obtained from 2-fluoro-3-(trifluoromethyl) aniline, as a light brown powder in 66% yield. $^1$H NMR (400 MHz, DMSO-d6): δ 10.49 (br s, 3H), 8.87 (s, 1H), 7.64 (dd, J=11.7, 2.0 Hz, 1H), 7.57 (dd, J=8.5, 2.0 Hz, 1H), 7.31 (t, J=8.5 Hz, 1H). UPLC-MS: $t_R$=1.42 min (Method A); MS (ESI) m/z calcd for $C_7H_7F_4N_2$ (M+H)$^+$: 195.0, found: 195.6.

Synthesis of Substituted Tetrahydro-γ-Carbolines

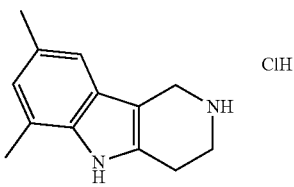

[Int-2 0.5] 6,8-Dimethyl-2, 3,4,5-tetrahydro-1H-pyrido[4,3-b]indole hydrochloride: Following GP2a, the title compound was obtained from (2,4-dimethylphenyl)hydrazine, and tert-butyl 4-oxopiperidine-1-carboxylate, as a brown solid in 47% yield. $^1$H NMR (400 MHz, DMSO-d6): δ 10.81 (s, 1H), 7.01 (s, 1H), 6.71 (s, 1H), 4.15 (s, 2H), 2.93 (t, J=6.0 Hz, 2H), 2.39 (s, 3H), 2.32 (s, 3H). UPLC-MS: $t_R$=1.52 min (Method A); MS (ESI) m/z calcd for $C_{13}H_{17}N_2$ (M+H)$^+$: 201.1, found: 201.3.

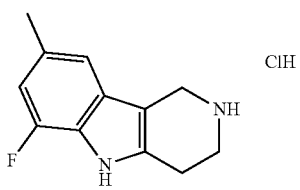

[Int-2 0.6] 6-Fluoro-8-methyl-2, 3,4,5-tetrahydro-1H-pyrido [4,3-b]indole hydrochloride: Following GP2a, the title compound was obtained from (2-fluoro-4-methyl-phenyl)hydrazine, and tert-butyl 4-oxopiperidine-1-carboxylate, as a brown solid in 63% yield. $^1$H NMR (400 MHz, DMSO-d6): δ 11.46 (s, 1H), 7.08 (s, 1H), 6.79 (d, J=12.4 Hz, 1H), 4.27 (s, 2H), 3.47 (t, J=6.1 Hz, 2H), 3.00 (t, J=6.0 Hz, 2H), 2.37 (s, 3H). UPLC-MS: $t_R$=1.44 min (Method A); MS (ESI) m/z calcd for $C_{12}H_{14}FN_2$ (M+H)$^+$: 205.1, found: 205.2.

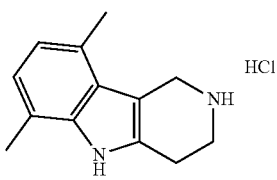

[Int-2 0.7] 6,9-Dimethyl-2, 3,4,5-tetrahydro-1H-pyrido [4,3-b]indole hydrochloride: Following GP2a, the title compound was obtained from (2,5 dimethylphenyl)hydrazine, and tert-butyl 4-oxopiperidine-1-carboxylate, as a brown solid in 47% yield. UPLC-MS: $t_R$=1.47 min (Method A); MS (ESI) m/z calcd for $C_{13}H_{17}N_2$ (M+H)$^+$: 201.1, found: 201.3.

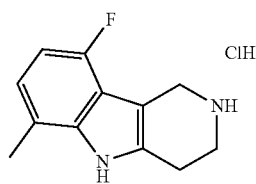

[Int-2.8] 9-Fluoro-6-methyl-2,3,4,5-tetrahydro-1H-pyrido [4,3-b]indole hydrochloride: Following GP2a, the title compound was obtained from (5-fluoro-2-methyl-phenyl)hydrazine hydrochloride, and tert-butyl 4-oxopiperidine-1-carboxylate, as a brown solid in 26% yield. $^1$H NMR (400 MHz, DMSO-d$_6$): δ 11.35 (s, 1H), 6.87-6.80 (m, 1H), 6.68 (dd, J=10.8, 7.9 Hz, 1H), 4.38 (s, 2H), 3.46 (t, J=6.1 Hz, 2H), 3.03 (t, J=6.2 Hz, 2H), 2.40 (s, 3H). UPLC-MS: $t_R$=1.44 min (Method A); MS (ESI) m/z calcd for $C_{12}H_{14}FN_2$ (M+H)$^+$: 205.1, found: 205.3.

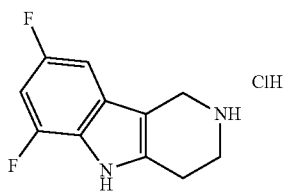 [SMILES: Fc1cc(F)c2[nH]c3c(c2c1)CNCC3 ; Cl]

[Int-2.9] 6,8-Difluoro-2,3,4,5-tetrahydro-1H-pyrido[4,3-b]indole hydrochloride: Following GP2a, the title compound was obtained from (2,4-difluoro-phenyl)hydrazine hydrochloride, and tert-butyl 4-oxopiperidine-1-carboxylate, as a brown solid in 51% yield: $^1$H NMR (400 MHz, DMSO-d$_6$) δ 11.76 (s, 1H), 9.28 (s, 2H), 7.19 (dd, J=9.4, 2.2 Hz, 1H), 6.98 (ddd, J=11.7, 9.8, 2.3 Hz, 1H), 4.26 (s, 2H), 3.46 (t, J=6.1 Hz, 2H), 3.03 (t, J=6.1 Hz, 2H). UPLC-MS: $t_R$=1.35 min (Method A); MS (ESI) m/z calcd for $C_{11}H_{11}F_2N_2$(M+H)$^+$: 209.1, found: 209.3.

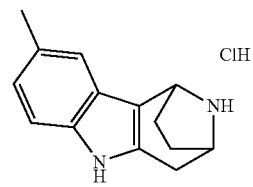 [SMILES: Cc1ccc2[nH]c3c(c2c1)C1CCC(C3)N1 ; Cl]

[Int-2 0.11] 2-Methyl-5, 6,7,8,9,10-hexahydro-7,10-epimino cyclohepta[b]indole hydrochloride: Following GP2a, the title compound was obtained from 4-tolyl hydrazine and tert-butyl 3-oxo-8-azabicyclo[3.2.1]octane-8-carboxylate, as a white solid in 36% yield. UPLC-MS: $t_R$=1.48 min (Method A); MS (ESI) m/z calcd for $C_{14}H_{17}N_2$(M+H)$^+$: 212.1, found: 212.2.

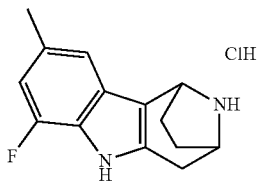 [SMILES: Cc1cc(F)c2[nH]c3c(c2c1)C1CCC(C3)N1 ; Cl]

[Int-2.12] 4-Fluoro-2-methyl-5,6,7,8,9,10-hexahydro-7,10-epiminocyclohepta[b]indole hydrochloride: Following GP2a, the title compound was obtained from (2-fluoro-4-methyl-phenyl)hydrazine hydrochloride and tert-butyl 3-oxo-8-azabicyclo[3.2.1]octane-8-carboxylate, as a white solid in 36% yield. UPLC-M S: $t_R$=1.55 min (Method A); MS (ESI) m/z calcd for $C_{14}H_{16}FN_2$ (M+H)$^+$: 231.1, found: 231.2.

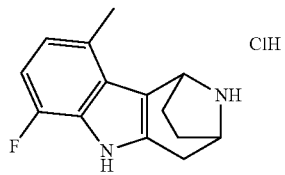 [SMILES: Cc1ccc(F)c2[nH]c3c(c12)C1CCC(C3)N1 ; Cl]

[Int-2 0.13] 4-Fluoro-1-methyl-5, 6,7,8,9,10-hexahydro-7,10-epiminocyclohepta[b]indole hydrochloride: Following GP2a, the title compound was obtained from [Int-1.2] and tert-butyl 3-oxo-8-azabicyclo[3.2.1]octane-8-carboxylate, as a white solid in 37% yield. UPLC-MS: $t_R$=1.56 min (Method A); MS (ESI) m/z calcd for $C_{14}H_{16}FN_2$ (M+H)$^+$: 231.1, found: 231.3.

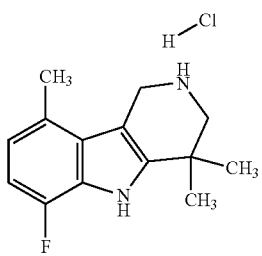

[Int-2 0.14] 6-Fluoro-4, 4,9-trimethyl-1,2,3,5-tetrahydro-pyrido[4,3-b]indole hydrochloride: Following GP2a, the title compound was obtained from [Int-1.2] and tert-butyl 3,3-dimethyl-4-oxo-piperidine-1-carboxylate, as a brown solid in 34% yield. UPLC-MS: $t_R$=1.49 min (Method A); MS (ESI) m/z calcd for $C_{14}H_{18}FN_2$ (M+H)$^+$: 233.1, found: 233.1.

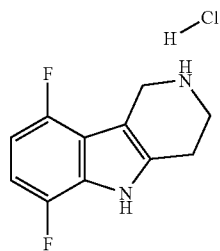

[Int-2.17] 6,9-Difluoro-2,3,4,5-tetrahydro-1H-pyrido[4,3-b]indole hydrochloride: Following GP2a, the title compound was obtained from (2,5-difluorophenyl)hydrazine and tert-butyl 4-oxopiperidine-1-carboxylate, as a brown solid in 22% yield. UPLC-MS: $t_R$=1.69 min (Method A); MS (ESI) m/z calcd for $C_{11}H_{11}F_2N_2$ (M+H)$^+$: 209.1, found: 209.5.

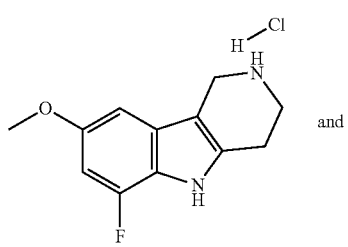

and

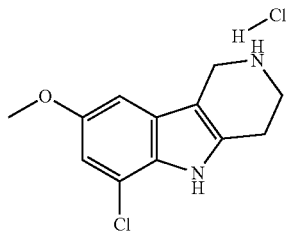

[Int-2.18] Mixture of 6-Fluoro-8-methoxy-2,3,4,5-tetrahydro-1H-pyrido [4,3-b]indole hydrochloride and 6-Chloro-8-methoxy-2, 3,4,5-tetrahydro-1H-pyrido [4,3-b] indole hydrochloride: Following GP2a, a mixture of the title compounds was obtained from [Int-1.3] and tert-butyl 4-oxopiperidine-1-carboxylate, as brown solid in 39% total yield. UPLC-MS: $t_R$1=1.39 min (Method A); MS (ESI) m/z calcd for $C_{12}H_{13}ClN_2O$ (M+H)$^+$: 237.1, found: 237.4; $t_R$2=1.52 min (Method A); MS (ESI) m/z calcd for $C_{12}H_{14}FN_2O$ (M+H)$^+$: 221.1, found: 221.8.

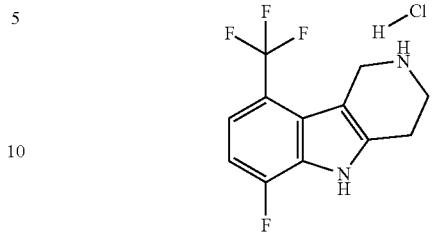

[Int-2 0.20] 6-Fluoro-9-(trifluoromethyl)-2,3,4,5-tetrahydro-1H-pyrido[4,3-b]indole hydrochloride: Following GP2a, the title compound was obtained from [Int-1.4] and tert-butyl 4-oxopiperidine-1-carboxylate, as a brown solid in 21% yield. UPLC-MS: $t_R$=1.41 min (Method A); MS (ESI) m/z calcd for $C_{12}H_{11}F_4N_2$ (M+H)$^+$: 259.1, found: 259.1.

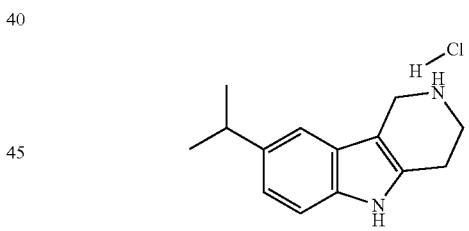

[Int-2 0.21] 6-Fluoro-8-(trifluoromethyl)-2,3,4,5-tetrahydro-1H-pyrido [4,3-b] indole hydrochloride: Following GP2a, the title compound was obtained from [Int-1.5] and tert-butyl 4-oxopiperidine-1-carboxylate, as a brown solid in 32% yield: UPLC-MS: $t_R$=1.41 min (Method A); MS (ESI) m/z calcd for $C_{12}H_{11}F_4N_2$ (M+H)$^+$: 259.1, found: 259.1.

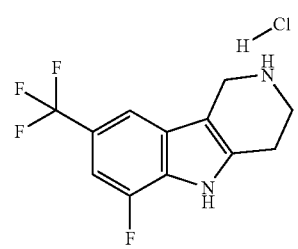

[Int-2.22] 8-Isopropyl-2,3,4,5-tetrahydro-1H-pyrido[4,3-b]indole hydrochloride: Following GP2a, the title compound was obtained from (4-isopropylphenyl)hydrazine and tert-butyl 4-oxopiperidine-1-carboxylate, as a white solid in 42% yield. UPLC-MS: $t_R$=1.67 min (Method A); MS (ESI) m/z calcd for $C_{14}H_{19}N_2$ (M+H)$^+$: 215.1, found: 215.2.

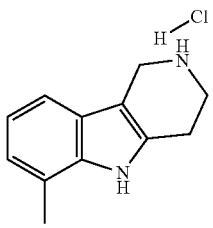

[Int-2 0.23] 6-Methyl-2, 3,4,5-tetrahydro-1H-pyrido [4,3-b]indole hydrochloride: Following GP2a, the title compound was obtained from o-tolylhydrazine and tert-butyl 4-oxopiperidine-1-carboxylate, as a white solid in 42% yield. UPLC-MS: $t_R$=1.31 min (Method A); MS (ESI) m/z calcd for $C_{12}H_{15}N_2(M+H)^+$:187.1, found: 187.2.

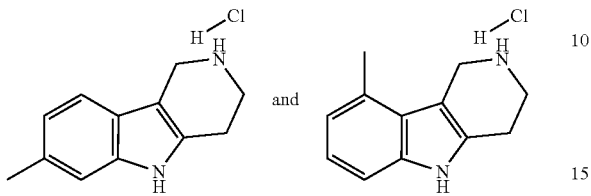

[Int-2.24] Mixture of 7-methyl-2,3,4,5-tetrahydro-1H-pyrido [4,3-b] indole hydrochloride and 9-methyl-2,3,4,5-tetrahydro-1H-pyrido[4,3-b]indole hydrochloride: Following GP2a, a mixture of the title compounds was obtained from (3-methylphenyl)hydrazine and tert-butyl 4-oxopiperidine-1-carboxylate, as a white solid in 50% total yield. UPLC-MS: $t_{R1}$=1.27 min, $t_{R2}$=1.31 min (Method A); MS (ESI) m/z calcd for $C_{12}H_{15}N_2(M+H)^+$:187.1, found: 187.1.

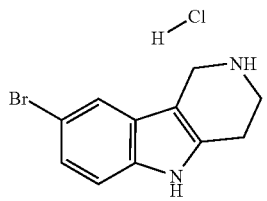

[Int-2.25] 8-Bromo-2,3,4,5-tetrahydro-1H-pyrido[4,3-b]indole hydrochloride: Following GP2a, the title compound was obtained from (4-bromophenyl)hydrazine hydrochloride and tert-butyl 4-oxopiperidine-1-carboxylate, after purification by trituration with chilled ethanol, as an off-white solid in 16% yield. $^1$H NMR (400 MHz, DMSO-$d_6$) δ 11.38 (s, 1H), 9.24 (br s, 2H), 7.69 (d, J=1.9 Hz, 1H), 7.32 (d, J=8.6 Hz, 1H), 7.20 (dd, J=8.6, 1.9 Hz, 1H), 4.28 (s, 2H), 3.46 (t, J=6.1 Hz, 2H), 3.03 (t, J=6.1 Hz, 2H); UPLC-MS: $t_R$=1.48 min (generic method); MS (ESI) m/z calcd for $C_{11}H_{12}BrN_2$ (M+H)$^+$: 251.0, found: 251.1.

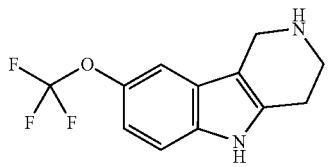 [SMILES: FC(F)(F)Oc1ccc2[nH]c3c(c2c1)CNCC3]

[Int-2.26] 8-(Trifluoromethoxy)-2,3,4,5-tetrahydro-1H-pyrido[4,3-b]indole: Following GP2a, the title compound was obtained from (4-trifluoromethoxy)hydrazine hydrochloride and tert-butyl 4-oxopiperidine-1-carboxylate, after purification by trituration with chilled ethanol as the solvent. The solid was partitioned between EtOAc (50 mL) and sat. aq. NaHCO$_3$ (50 mL). The organic phase was separated, washed with brine (50 mL), dried over anhydrous Na$_2$SO$_4$, filtered and the solvent evaporated under reduced pressure. The resultant residue was purified by silica gel flash-column chromatography, with DCM/MeOH (9:1) as the eluent, to yield the title compound as a yellow solid in 8% yield. $^1$H NMR (400 MHz, DMSO-$d_6$) δ 11.11 (s, 1H), 7.41-7.23 (m, 2H), 6.97 (dd, J=8.9, 2.3 Hz, 1H), 3.94 (s, 2H), 3.12 (t, J=5.8 Hz, 2H), 2.76 (t, J=5.8 Hz, 2H); UPLC-MS: $t_R$=1.64 min (generic method); MS (ESI) m/z calcd for $C_{12}H_{12}F_3N_2O$ (M+H)$^+$: 257.1, found: 257.2.

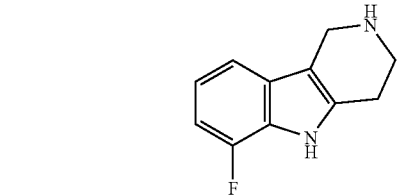 [SMILES: Fc1cccc2c3c([nH]c12)CCNC3]

[Int-2.27] 6-Fluoro-2,3,4,5-tetrahydro-1H-pyrido[4,3-b]indole: Following GP2a, the title compound was obtained from (2-fluorophenyl)hydrazine hydrochloride and tert-butyl 4-oxopiperidine-1-carboxylate, after purification by trituration with chilled ethanol as the solvent. The solid was partitioned between EtOAc (50 mL) and sat. aq. NaHCO$_3$ (50 mL). The organic phase was separated, washed with brine (50 mL), dried over anhydrous Na$_2$SO$_4$, filtered and the solvent evaporated under reduced pressure. The resultant residue was purified by silica gel flash-column chromatography, with DCM/MeOH/Et$_3$N (9:1:0.1) as the eluent, to yield the title compound as an off-white solid in 5% yield. $^1$H NMR (400 MHz, DMSO-d6) δ 11.25 (s, 1H), 7.16 (d, J=7.7 Hz, 1H), 6.96-6.77 (m, 1H), 3.94 (s, 2H), 3.11 (t, J=5.8 Hz, 2H), 2.75 (t, J=5.8 Hz, 2H); UPLC-MS: $t_R$=1.25 min (generic method); MS (ESI) m/z calcd for $C_{11}H_{12}FN_2$ (M+H)$^+$: 191.1, found: 191.1.

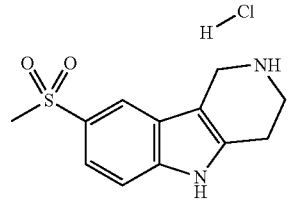

[Int-2 0.28] 8-Methylsulfonyl-2, 3,4,5-tetrahydro-1H-pyrido [4,3-b]indole hydrochloride: Following GP2c, the title compound was obtained from (4-methylsulfonylphenyl)hydrazine hydrochloride and piperidin-4-one hydrochloride, after purification by trituration with DCM as the solvent, as a yellow solid in a quantitative yield. UPLC-MS: $t_R$=1.08 min (generic method); MS (ESI) m/z calcd for $C_{12}H_{15}N_2O_2S$ (M+H)$^+$: 251.1, found: 251.1.

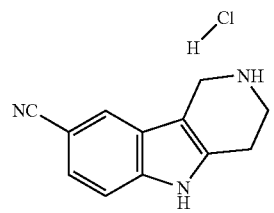

[Int-2.29] 2,3,4,5-Tetrahydro-1H-pyrido[4,3-b]indole-8-carbonitrile hydrochloride: Following GP2c, the title compound was obtained from 4-hydrazinobenzonitrile hydrochloride and piperidin-4-one hydrochloride, after purification by trituration with chilled ethanol as the solvent, as a yellow solid in 73% yield. UPLC-MS: $t_R$=1.10 min (generic method); MS (ESI) m/z calcd for $C_{12}H_{12}N_3$ (M+H)$^+$: 198.1, found: 198.1.

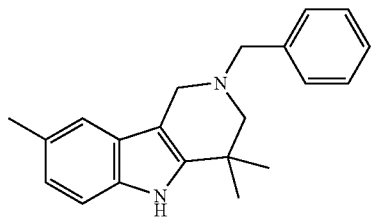 [SMILES: Cc1ccc2[nH]c3c(c2c1)CN(Cc1ccccc1)CC3(C)C]

[Int-2.30] 2-Benzyl-4,4,8-trimethyl-3,5-dihydro-1H-pyrido [4,3-b]indole: Following GP2a, the title compound was obtained from p-tolylhydrazine and 1-benzyl-3,3-dimethyl-piperidin-4-one, after purification by trituration with chilled ethanol as the solvent. The solid was partitioned between EtOAc (50 mL) and sat. aq. NaHCO$_3$ (50 mL). The organic phase was separated, washed with brine (50 mL), dried over anhydrous Na$_2$SO$_4$, filtered and the solvent evaporated under reduced pressure. The resultant residue was purified by silica gel flash-column chromatography, with DCM/MeOH (95:5) as the eluent, to yield the title compound as a yellow oil in 16% yield. $^1$H NMR (400 MHz, DMSO-d$_6$) δ 10.64 (s, 1H), 7.45-7.31 (m, 4H), 7.30-7.23 (m, 1H), 7.14 (d, J=8.2 Hz, 1H), 7.02 (br s, 1H), 6.81 (dd, J=8.2, 1.6 Hz, 1H), 3.72 (s, 2H), 3.51 (s, 2H), 2.45 (s, 2H), 2.31 (s, 3H), 1.26 (s, 6H); UPLC-MS: $t_R$=1.82 min (apolar method); MS (ESI) m/z calcd for $C_{21}H_{25}N_2$(M+H)$^+$: 305.2, found: 305.3.

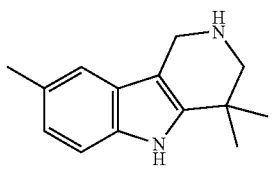

[Int-2 0.31] 4,4,8-Trimethyl-1,2, 3,5-tetrahydropyrido [4,3-b]indole: To a solution of [Int-2.30] (0.1 g, 0.33 mmol) in EtOH (5 mL) were added NH$_4$HCO$_2$ (0.208 g, 3.30 mmol) and Pd/C (0.010 g), and the resultant mixture stirred at room temperature for 4 h. The suspension was filtered through a pad of celite and the filtrate evaporated under reduced pressure. The resultant residue was partitioned between EtOAc (50 mL) and sat. aq. NaHCO$_3$ (50 mL). The organic phase was separated, washed with brine (50 mL), dried over anhydrous Na$_2$SO$_4$, filtered and the solvent evaporated under reduced pressure to yield the title compound as a yellow solid in a quantitative yield. $^1$H NMR (400 MHz, DMSO-d$_6$) δ 10.57 (s, 1H), 7.14 (d, J=8.1 Hz, 1H), 7.06 (br s, 1H), 6.81 (dd, J=8.1, 1.6 Hz, 1H), 3.79 (s, 2H), 2.71 (s, 2H), 2.33 (s, 3H), 1.24 (s, 6H); UPLC-MS: $t_R$=1.50 min (generic method); MS (ESI) m/z calcd for $C_{14}H_{19}N_2$ (M+H)$^+$: 215.2, found: 215.2.

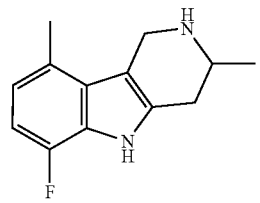

[Int-2.32] (R/S)-6-Fluoro-3,9-dimethyl-2, 3,4,5-tetrahydro-1H-pyrido[4,3-b]indole: Following GP2b, using [Int-1.2] and tert-butyl 2-methyl-4-oxo-piperidine-1-carboxylate a 8:2 mixture of regioisomers was afforded. Hydrochloride salt was removed with sat. aq. NaHCO$_3$, and aqueous layer was extracted with EtOAc (3×20 mL). Organics were dried over Na$_2$SO$_4$, filtered, and evaporated After purification by neutral alumina chromatography with DCM/MeOH/NH$_3$ (95:5:0.1) the title compound was obtained as a brown solid with a 29% yield. $^1$H-NMR (400 MHz, DMSO-d6) δ 11.03 (bs), 6.64 (dd, J=11.3, 7.6 Hz, 1H), 6.57 (ddd, J=7.9, 4.8, 0.7 Hz, 1H), 4.17 (dd, J=14.8, 1.1 Hz, 1H), 4.08 (app-dt, J=14.8, 1.8, 1.8 Hz, 1H), 2.89 (m, 1H), 2.67 (ddd, J=17.5, 3.5, 1.5 Hz, 1H), 2.34 (m, 1H), 2.44 (s, 3H), 1.18 (d, J=6.3 Hz, 3H). UPLC-MS: $t_R$=1.46 min (Method A); MS (ESI) m/z calcd for $C_{19}H_{17}FN_2O$ (M+H)$^+$: 218.27; found: 219.4.

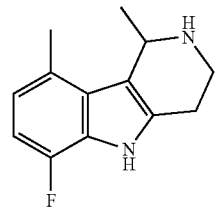 [SMILES: Cc1ccc(F)c2[nH]c3c(c12)C(C)NCC3]

[Int-2.33] (R/S)-6-Fluoro-1,9-dimethyl-2, 3,4,5-tetrahydro-1H-pyrido[4,3-b]indole: Following GP2b, using [Int-1.2] and tert-butyl 2-methyl-4-oxo-piperidine-1-carboxylate, a 8:2 mixture of regioisomers was afforded. Hydrochloride salt was removed with sat. aq. NaHCO$_3$, and aqueous layer was extracted with EtOAc (3×20 mL). Organics were dried over Na$_2$SO$_4$, filtered, and evaporated Purification by neutral alumina column chromatography with DCM/MeOH:NH$_3$ (95:5:0.1) gave the title compound as a brown resin with a 6% yield: $^1$H-NMR (400 MHz, DMSO-d6) δ 11.06 (bs), 6.66 (dd, J=11.1, 7.6 Hz, 1H), 6.58-6.61 (m, 1H), 4.39 (q, J=6.5 Hz, 1H), 3.10 (ddd, J=13.1, 10.2, 4.9 Hz, 1H), 2.97 (ddd, J=12.8, 6.1, 2.2 Hz, 1H), 2.66 (m, 1H), 2.56 (ddd, J=16.0, 4.8, 2.0 Hz, 1H), 2.50 (s, 3H), 1.37 (d, J=6.5 Hz, 3H). UPLC-MS: $t_R$=1.46 min (Method A); MS (ESI) m/z calcd for $C_{19}H_{17}FN_2O$ (M+H)$^+$: 218.27; found: 219.4.

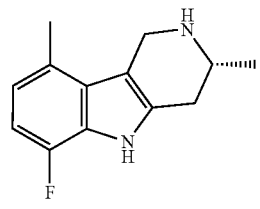 [SMILES: Cc1ccc(F)c2[nH]c3c(c12)CN[C@H](C)C3]

[Int-2.34] (R)-6-Fluoro-3,9-dimethyl-2, 3,4,5-tetrahydro-1H-pyrido[4,3-b]indole: Following GP2b, using [Int-1.2] and tert-butyl (R)-2-methyl-4-oxo-piperidine-1-carboxylate, a 8:2 mixture of regioisomers was afforded. Hydrochloride salt was removed with sat. aq. NaHCO₃, and aqueous layer was extracted with EtOAc (3×20 mL). Organics were dried over Na₂SO₄, filtered, and evaporated After purification by neutral alumina chromatography with DCM/MeOH/NH₃ (95:5:0.1) the title compound was obtained as a brown solid with a 28% yield. ¹H-NMR (400 MHz, DMSO-d6) δ 11.03 (bs), 6.64 (dd, J=11.3, 7.6 Hz, 1H), 6.57 (ddd, J=7.9, 4.8, 0.7 Hz, 1H), 4.17 (dd, J=14.8, 1.1 Hz, 1H), 4.08 (app-dt, J=14.8, 1.8, 1.8 Hz, 1H), 2.89 (m, 1H), 2.67 (ddd, J=17.5, 3.5, 1.5 Hz, 1H), 2.34 (m, 1H), 2.44 (s, 3H), 1.18 (d, J=6.3 Hz, 3H). UPLC-MS: t$_R$=1.46 min (Method A); MS (ESI) m/z calcd for C₁₉H₁₇FN₂O (M+H)⁺: 218.27; found: 219.4.

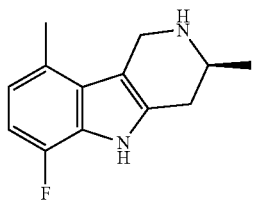 [SMILES: Cc1ccc(F)c2[nH]c3c(c12)CN[C@@H](C)C3]

[Int-2.35] (S)-6-fluoro-3,9-dimethyl-2, 3,4,5-tetrahydro-1H-pyrido[4,3-b]indole: Following GP2b, using [Int-1.2] and tert-butyl (S)-2-methyl-4-oxo-piperidine-1-carboxylate, a 8:2 mixture of regioisomers was afforded. Hydrochloride salt was removed with sat. aq. NaHCO₃, and aqueous layer was extracted with EtOAc (3×20 mL). Organics were dried over Na₂SO₄, filtered, and evaporated. After purification by neutral alumina chromatography with DCM/MeOH/NH₃ (95:5:0.1) the title compound was obtained as a brown solid with a 28% yield. ¹H-NMR (400 MHz, DMSO-d6) δ 11.03 (bs), 6.64 (dd, J=11.3, 7.6 Hz, 1H), 6.57 (ddd, J=7.9, 4.8, 0.7 Hz, 1H), 4.17 (dd, J=14.8, 1.1 Hz, 1H), 4.08 (app-dt, J=14.8, 1.8, 1.8 Hz, 1H), 2.89 (m, 1H), 2.67 (ddd, J=17.5, 3.5, 1.5 Hz, 1H), 2.34 (m, 1H), 2.44 (s, 3H), 1.18 (d, J=6.3 Hz, 3H). UPLC-MS: t$_R$=1.46 min (Method A); MS (ESI) m/z calcd for C₁₉H₁₇FN₂O (M+H)⁺: 218.27; found: 219.4.

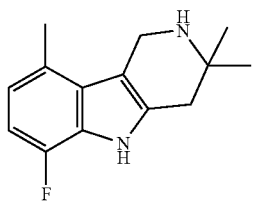 [SMILES: Cc1ccc(F)c2[nH]c3c(c12)CNC(C)(C)C3]

[Int-2 0.36] 6-Fluoro-3, 3,9-trimethyl-2, 3,4,5-tetrahydro-1H-pyrido[4,3-b]indole: Following GP2b, using [Int-1.2] and tert-butyl 2,2-dimethyl-4-oxo-piperidine-1-carboxylate, the title compound was obtained after purification by neutral alumina chromatography with DCM/MeOH/NH₃ (95:5:0.1), as a brown solid with a 15% yield. ¹H-NMR (400 MHz, CDCl₃) δ 8.28 (bs, 1H), 6.62-6.72 (m, 2H), 4.28 (s, 2H), 2.52 (s, 2H), 2.35 (s, 3H), 1.42 (s, 6H). UPLC-MS: t$_R$=1.46 min (Method A); MS (ESI) m/z calcd for C₁₄H₁₇FN₂ (M+H)⁺: 233.3; found: 233.5.

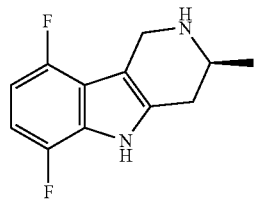

[Int-2.37] (S)-6,9-Difluoro-3-methyl-2, 3,4,5-tetrahydro-1H-pyrido[4,3-b]indole: Following GP2c, using (2,5-difluorophenyl)hydrazine hydrochloride and tert-butyl (S)-methyl-4-oxo-piperidine-1-carboxylate, a 8:2 mixture of regioisomers was afforded. Hydrochloride salt salt was removed with sat. aq. NaHCO₃, and aqueous layer was extracted with EtOAc (3×20 mL). Organics were dried over Na₂SO₄, filtered, and evaporated After purification by neutral alumina chromatography with DCM/MeOH/NH₃ (95:5:0.1) the title compound was obtained as a brown solid with a 23% yield. ¹H-NMR (400 MHz, DMSO-d6) δ 11.40 (bs, 1H), 6.75 (ddd, J=12.1, 8.5, 3.6 Hz, 1H), 6.61 (ddd, J=11.7, 8.5, 3.2 Hz, 1H), 3.99 (d, J=15.6 Hz, 1H), 3.94 (app-dt, J=15.1, 1.9, 1.9 Hz, 1H), 2.92 (m, 1H), 2.69 (ddd, J=16.3, 3.7, 1.6 Hz, 1H), 2.34 (app-dt, J=16.2, 2.0, 2.0 Hz, 1H), 1.18 (d, J=6.3 Hz, 3H). UPLC-MS: t$_R$=1.29 min (Method A); MS (ESI) m/z calcd for C₁₂H₁₂F₂N₂ (M+H)⁺: 223.1; found: 223.4.

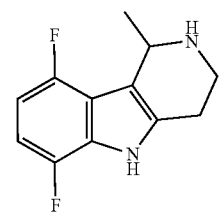 [SMILES: CC1NCCc2[nH]c3c(F)ccc(F)c3c21]

[Int-2.38] (R/S)-6,9-Difluoro-1-methyl-2,3,4,5-tetrahydro-1H-pyrido[4,3-b]indole: Following GP2c, using (2,5-difluorophenyl)hydrazine hydrochloride and tert-butyl (S)-methyl-4-oxo-piperidine-1-carboxylate, a 8:2 mixture of regioisomers was afforded. Hydrochloride salt was removed with sat. aq. NaHCO₃, and aqueous layer was extracted with EtOAc (3×20 mL). Organics were dried over Na₂SO₄, filtered, and evaporated Purification by neutral alumina column chromatography with DCM/MeOH:NH₃ (95:5:0.1) gave the title compound as a brown resin with a 6% yield. ¹H-NMR (400 MHz, DMSO-d6) δ 11.06 (bs), 6.66 (dd, J=11.1, 7.6 Hz, 1H), 6.58-6.61 (m, 1H), 4.39 (q, J=6.5 Hz, 1H), 3.10 (ddd, J=13.1, 10.2, 4.9 Hz, 1H), 2.97 (ddd, J=12.8, 6.1, 2.2 Hz, 1H), 2.66 (m, 1H), 2.56 (ddd, J=16.0, 4.8, 2.0 Hz, 1H), 2.50 (s, 3H), 1.37 (d, J=6.5 Hz, 3H). UPLC-MS: t$_R$=1.46 min (Method A); MS (ESI) m/z calcd for C₁₉H₁FN₂O (M+H)⁺: 218.27; found: 219.4.

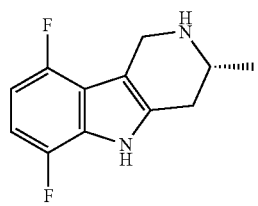 [SMILES: C[C@@H]1Cc2[nH]c3c(F)ccc(F)c3c2CN1]

[Int-2.39] (R)-6,9-Difluoro-3-methyl-2, 3,4,5-tetrahydro-1H-pyrido[4,3-b]indole: Following GP2c, using (2,5-difluorophenyl)hydrazine hydrochloride and tert-butyl (R)-methyl-4-oxo-piperidine-1-carboxylate, a 8:2 mixture of regioisomers was afforded. Hydrochloride salt was removed with sat. aq. NaHCO₃, and aqueous layer was extracted with EtOAc (3×20 mL). Organics were dried over Na₂SO₄, filtered, and evaporated After purification by neutral alumina chromatography with DCM/MeOH/NH₃ (95:5:0.1) the title compound was obtained as a brown solid with a 23% yield. ¹H-NMR (400 MHz, DMSO-d6) δ 11.40 (bs, 1H), 6.75 (ddd, J=12.1, 8.5, 3.6 Hz, 1H), 6.61 (ddd, J=11.7, 8.5, 3.2 Hz, 1H), 3.99 (d, J=15.6 Hz, 1H), 3.94 (app-dt, J=15.1, 1.9, 1.9 Hz, 1H), 2.92 (m, 1H), 2.69 (ddd, J=16.3, 3.7, 1.6 Hz, 1H), 2.34 (app-dt, J=16.2, 2.0, 2.0 Hz, 1H), 1.18 (d, J=6.3 Hz, 3H). UPLC-MS: $t_R$=1.29 min (Method A); MS (ESI) m/z calcd for $C_{12}H_{12}F_2N_2$ (M+H)⁺: 223.1; found: 223.4.

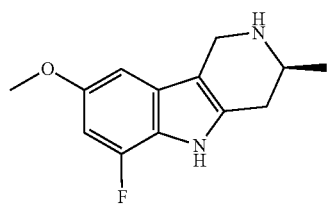

[Int-2.40] (S)-6-Fluoro-8-methoxy-3-methyl-2,3,4,5-tetrahydro-1H-pyrido[4,3-b]indole: Following GP2b, using [Int-1.3] and tert-butyl (S)-methyl-4-oxo-piperidine-1-carboxylate, a 7:3 mixture of regioisomers was afforded. Hydrochloride salt was removed with sat. aq. NaHCO₃, and aqueous layer was extracted with EtOAc (3×20 mL). Organics were dried over Na₂SO₄, filtered, and evaporated After purification by neutral alumina chromatography with DCM/MeOH/NH₃ (95:5:0.1) the title compound was obtained as a brown solid with a 18% yield. ¹H-NMR (400 MHz, DMSO-d6) D 10.90 (bs), 6.66 (d, J=2.2 Hz, 1H), 6.50 (dd, J=12.8, 2.1 Hz, 1H), 3.87 (d, J=14.5 Hz, 1H), 3.80 (d, J=13.8 Hz, 1H), 3.73 (s, 3H), 3.16 (m, 1H), 2.92 (m, 1H), 2.66 (m, 1H), 2.32 (m, 1H), 1.19 (d, J=6.3 Hz, 3H). UPLC-MS: $t_R$=1.28 min (Method A); MS (ESI) m/z calcd for $C_{13}H_{15}FN_2O$ (M+H)⁺: 235.27; found: 235.4.

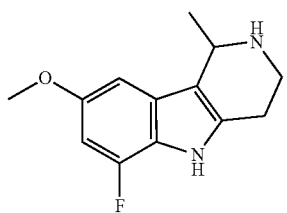 [SMILES: COc1cc(F)c2[nH]c3c(c2c1)C(C)NCC3]

[Int-2.41] (R/S)-6-Fluoro-1-methyl-6-methoxy-2,3,4,5-tetrahydro-1H-pyrido[4,3-b]indole: Following GP2b, using [Int-1.3] and tert-butyl (S)-methyl-4-oxo-piperidine-1-carboxylate a 7:3 mixture of regioisomers was afforded. Hydrochloride salt was removed with sat. aq. NaHCO₃, and aqueous layer was extracted with EtOAc (3×20 mL). Organics were dried over Na₂SO₄, filtered, and evaporated Purification by neutral alumina column chromatography with DCM/MeOH:NH₃ (95:5:0.1) gave the title compound as a brown solid with a 6% yield. ¹H-NMR (400 MHz, DMSO-d6) δ 10.94 (bs), 6.71 (d, J=2.1 Hz, 1H), 6.51 (dd, J=12.8, 2.1 Hz, 1H), 4.03 (q, J=6.5 Hz, 1H), 3.73 (s, 3H), 3.17 (m, 1H), 3.11 (app-dt, J=12.5, 5.0, 5.0 Hz, 1H), 2.84 (ddd, J=12.3, 7.5, 5.2 Hz, 1H), 2.61 (app-dtd, J=16.6, 5.1, 5.1, 1.2 Hz, 1H), 1.36 (d, J=6.5 Hz, 3H). UPLC-MS: $t_R$=1.28 min (Method A); MS (ESI) m/z calcd for $C_{13}H_{15}FN_2O$ (M+H)⁺: 235.27; found: 235.4.

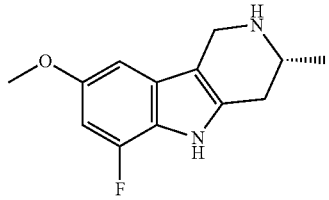

[Int-2.42] (3R)-6-Fluoro-8-methoxy-3-methyl-2,3,4,5-tetrahydro-1H-pyrido[4,3-b]indole: Following GP2b, using [Int-1.3] and tert-butyl (2R)-methyl-4-oxo-piperidine-1-carboxylate, a 7:3 mixture of regioisomers was afforded. Hydrochloride salt was removed with sat. aq. NaHCO₃, and aqueous layer was extracted with EtOAc (3×20 mL). Organics were dried over Na₂SO₄, filtered, and evaporated After purification by neutral alumina chromatography with DCM/MeOH/NH₃ (95:5:0.1) the title compound was obtained as a brown solid with a 18% yield. ¹H-NMR (400 MHz, DMSO-d6) δ 10.90 (bs), 6.66 (d, J=2.2 Hz, 1H), 6.50 (dd, J=12.8, 2.1 Hz, 1H), 3.87 (d, J=14.5 Hz, 1H), 3.80 (d, J=13.8 Hz, 1H), 3.73 (s, 3H), 3.16 (m, 1H), 2.92 (m, 1H), 2.66 (m, 1H), 2.32 (m, 1H), 1.19 (d, J=6.3 Hz, 3H). UPLC-MS: $t_R$=1.28 min (Method A); MS (ESI) m/z calcd for $C_{13}H_{15}FN_2O$ (M+H)⁺: 235.27; found: 235.4.

Synthesis of Final Compounds (1-Phenyl-1-H-pyrazol-4-yl)-(1,3,4,5-tetrahydropyrido[4,3-b]indol-2-yl)methanone: Following GP3b, the title compound was obtained from 2,3,4,5-tetrahydro-1H-pyrido[4,3-b]indole (0.060 g, 0.32 mmol) and 1-phenylpyrazole-4-carboxylic acid (0.030 g, 0.32 mmol), after purification by silica gel flash-column chromatography with DCM/EtOAc (8:2) as the eluent, as a white solid (0.030 g, 26%). ¹H NMR (400 MHz, DMSO-d₆): δ 10.95 (s, 1H), 8.89 (s, 1H), 8.07 (s, 1H), 7.98-7.88 (m, 2H), 7.54 (dd, J=8.6, 7.3 Hz, 2H), 7.45 (d, J=7.8 Hz, 1H), 7.42-7.33 (m, 1H), 7.30 (d, J=8.0 Hz, 1H), 7.04 (t, J=7.4 Hz, 1H), 6.96 (s, 1H), 5.00-4.70 (m, 2H), 4.09-3.93 (m, 2H), 3.07-2.83 (m, 2H). UPLC-MS: $t_R$=2.12 min (Method A); MS (ESI) m/z calcd for $C_{21}H_{19}N_9O$ (M+H)⁺: 343.1, found: 343.2.

(8-Methoxy-1,3,4,5-tetrahydropyrido[4,3-b]indol-2-yl)-[5-(trifluoromethyl)-1H-pyrazol-3-yl]methanone: Following GP3a, the title compound was obtained from 8-methoxy-2,3,4,5-tetrahydro-1H-pyrido[4,3-b]indole (0.040 g, 0.20 mmol) and 5-(trifluoromethyl)-1H-pyrazole-3-carboxylic acid (0.036 g, 0.20 mmol), after purification by silica gel flash-column chromatography with DCM/EtOAc (8:2) as the eluent, as a white solid (0.055 g, 76%). ¹H NMR showed the presence of conformers: ¹H NMR (400 MHz, DMSO-d₆) δ 14.38 (s, 1H), 10.79 (s, 1H), 7.42-7.08 (m, 2H), 7.14-6.83 (m, 1H), 6.68 (dd, J=8.6, 2.4 Hz, 1H), 5.02-4.63 (m, 2H), 4.12-3.84 (m, 2H), 3.84-3.56 (m, 3H), 3.11-2.72 (m, 2H); UPLC-MS: $t_R$=2.00 min (generic method); MS (ESI) m/z calcd for $C_{17}H_{16}F_3N_4O_2$ (M+H)⁺: 365.1, found: 365.1.

(8-Methyl-1, 3,4,5-tetrahydropyrido[4,3-b] indol-2-yl)-[5-(trifluoromethyl)-1H-pyrazol-3-yl]methanone: Following GP3a, the title compound was obtained from 8-methyl- 2,3,4,5-tetrahydro-1H-pyrido[4,3-b]indole (0.037 g, 0.20 mmol) and 5-(trifluoromethyl)-1H-pyrazole-3-carboxylic acid (0.036 g, 0.20 mmol), after purification by silica gel flash-column chromatography with DCM/EtOAc (8:2) as the eluent, as a white solid (0.030 g, 40%). $^1$H NMR showed the presence of conformers: $^1$H NMR (400 MHz, DMSO-d$_6$) δ 14.37 (s, 1H), 10.82 (s, 17H), 7.37-6.96 (m, 3H) 6.87 (s, 3H), 4.92-4.69 (m, 2H), 4.10-3.77 (m, 2H), 3.04-2.71 (m, 2H), 2.43-2.25 (m, 3H); UPLC-MS: $t_R$=2.21 min (generic method); MS (ESI) m/z calcd for $C_{17}H_{16}F_3N_4O$ (M+H)$^+$: 349.1, found: 349.1.

(5-Methyl-1H-pyrazol-3-yl)-(8-methyl-1,3,4,5-tetrahydropyrido[4,3-b]indol-2-yl)-methanone: Following GP3a, the title compound was obtained from 8-methyl-2,3,4,5-tetrahydro-1H-pyrido[4,3-b]indole (0.037 g, 0.20 mmol) and 5-methyl-1H-pyrazole-3-carboxylic acid (0.032 g, 0.20 mmol), after purification by silica gel flash-column chromatography with DCM/EtOAc (1:1) as the eluent, as an off-white solid (0.031 g, 49%). $^1$H NMR showed the presence of conformers: $^1$H NMR (400 MHz, DMSO-d$_6$) δ 12.86 (s, 1H), 10.75 (s, 1H), 7.29-6.97 (m, 2H), 6.91-6.76 (m, 1H), 6.60-6.20 (m, 1H), 4.90 (app-d, J=130.5 Hz, 2H), 4.19 (s, 1H), 3.98 (s, 1H), 2.99-2.67 (m, 2H), 2.41-2.30 (m, 3H), 2.31-2.21 (m, 3H); UPLC-MS: $t_R$=1.82 min (generic method); MS (ESI) m/z calcd for $C_{17}H_{19}N_4O$ (M+H)$^+$: 295.2, found: 295.1.

(5-Isopropyl-1H-pyrazol-3-yl)-(8-methyl-1,3,4,5-tetrahydropyrido[4,3-b]indol-2-yl)-methanone: Following GP3a, the title compound was obtained from 8-methyl-2,3,4,5-tetrahydro-1H-pyrido[4,3-b]indole (0.037 g, 0.20 mmol) and 5-isopropyl-1H-pyrazole-3-carboxylic acid (0.036 g, 0.20 mmol), after purification by silica gel flash-column chromatography with DCM/EtOAc (4:6) as the eluent, as a white solid (0.037 g, 54%). $^1$H NMR showed the presence of conformers: $^1$H NMR (400 MHz, DMSO-d6) δ 12.91 (s, 1H), 10.75 (s, 1H), 7.28-6.95 (m, 2H), 6.93-6.75 (m, 1H), 6.62-6.20 (m, 1H), 4.93 (app-d, J=150.3 Hz, 2H), 4.21 (s, 1H), 3.98 (s, 1H), 3.19-2.69 (m, 3H), 2.35 (app-d, J=13.1 Hz, 3H), 1.31-1.02 (m, 6H); UPLC-MS: $t_R$=2.06 min (generic method); MS (ESI) m/z calcd for $C_{19}H_{23}N_4O$ (M+H)$^+$: 323.2, found: 323.2.

(8-Methyl-1, 3,4,5-tetrahydropyrido[4,3-b] indol-2-yl)-(1H-pyrazol-3-yl)methanone: Following GP3a, the title compound was obtained from 8-methyl-2,3,4,5-tetrahydro-1H-pyrido[4,3-b]indole (0.037 g, 0.20 mmol) and 1H-pyrazole-3-carboxylic acid (0.022 g, 0.20 mmol), after purification by silica gel flash-column chromatography with DCM/EtOAc (4:6) as the eluent, as an off-white solid (0.022 g, 37%). $^1$H NMR showed the presence of conformers: $^1$H NMR (400 MHz, DMSO-d6) 13.22 (s, 1H), 10.78 (s, 1H), 8.02-7.44 (m, 1H), 7.37-6.96 (m, 2H), 6.96-6.77 (m, 1H), 6.74-6.45 (m, 1H), 4.93 (app-d, J=123.2 Hz, 2H), 4.19 (s, 1H), 4.01 (s, 1H), 3.06-2.72 (m, 2H), 2.36 (app-d, J=16.1 Hz, 3H); UPLC-MS: $t_R$=1.75 min (generic method); MS (ESI) m/z calcd for $C_{16}H_{17}N_4O$ (M+H)$^+$: 281.1, found: 281.1.

[6-(Dimethylamino)-1H-indol-2-yl]-(8-methyl-1,3,4,5-tetrahydropyrido[4,3-b]indol-2-yl)-methanone: Following GP3a, the title compound was obtained from 8-methyl-2,3,4,5-tetrahydro-1H-pyrido[4,3-b]indole (0.037 g, 0.20 mmol) and 6-(dimethylamino)-1H-indole-2-carboxylic acid (0.048 g, 0.20 mmol), after purification by silica gel flash-column chromatography with DCM/EtOAc (4:6) as the eluent, as an off-white solid (0.020 g, 33%). $^1$H NMR (400 MHz, DMSO-d$_6$) δ 11.09 (s, 1H), 10.80 (s, 1H), 7.46 (d, J=8.8 Hz, 1H), 7.22 (s, 1H), 7.18 (d, J=8.2 Hz, 1H), 6.91-6.80 (m, 2H), 6.74 (dd, J=8.9, 2.2 Hz, 1H), 6.63 (d, J=2.1 Hz, 1H), 4.91 (br s, 2H), 4.09 (s, 2H), 2.99-2.90 (m, 2H), 2.91 (s, 6H), 2.35 (s, 3H); UPLC-MS: $t_R$=2.44 min (generic method); MS (ESI) m/z calcd for $C_{23}H_{25}N_4O$ (M+H)$^+$: 373.2, found: 373.1.

1H-Indol-2-yl-(8-methyl-1,3,4,5-tetrahydropyrido[4,3-b]indol-2-yl)methanone: Following GP3a, the title compound was obtained from 8-methyl-2,3,4,5-tetrahydro-1H-pyrido[4,3-b]indole (0.037 g, 0.20 mmol) and 1H-indole-2-carboxylic acid (0.032 g, 0.20 mmol), after purification by silica gel flash-column chromatography with DCM/EtOAc (8:2) as the eluent, as a white solid (0.025 g, 35%). $^1$H NMR (400 MHz, DMSO-d$_6$) δ 11.61 (s, 1H), 10.82 (s, 1H), 7.66 (d, J=7.9 Hz, 1H), 7.46-7.43 (m, 1H), 7.27-7.13 (m, 3H), 7.07 (ddd, J=7.9, 6.9, 1.0 Hz, 1H), 6.97 (br s, 1H), 6.91-6.83 (m, 1H), 4.92 (br s, 2H), 4.06 (s, 2H), 2.96 (s, 2H), 2.35 (s, 3H); UPLC-MS: $t_R$=2.41 min (generic method); MS (ESI) m/z calcd for $C_{21}H_{20}N_3O$ (M+H)$^+$: 330.2, found: 330.1. [011] (8-Methyl-1, 3,4,5-tetrahydropyrido[4,3-b]indol-2-yl)-[2-(trifluoromethyl)-1H-imidazol-4-yl]-methanone: Following GP3a, the title compound was obtained from 8-methyl-2,3,4,5-tetrahydro-1H-pyrido[4,3-b]indole (0.037 g, 0.20 mmol) and 2-(trifluoromethyl)-1H-imidazole-4-carboxylic acid (0.036 g, 0.20 mmol), after purification by silica gel flash-column chromatography with DCM/MeOH (95:5) as the eluent, as a white solid (0.052 g, 78%). $^1$H NMR showed the presence of conformers: $^1$H NMR (400 MHz, DMSO-d$_6$) δ 14.10 (br s, 1H), 10.77 (s, 1H), 7.91 (br s, 1H), 7.33-6.95 (m, 2H), 6.86 (d, J=8.2 Hz, 1H), 5.34-4.53 (m, 2H), 4.52-3.64 (m, 2H), 2.90 (br s, 2H), 2.36 (s, 3H); UPLC-MS: $t_R$=2.00 min (generic method); MS (ESI) m/z calcd for $C_{17}H_{16}F_3N_4O$ (M+H)$^+$: 349.1, found: 349.1.

(3,5-Dimethyl-1H-pyrazol-4-yl)-(8-methyl-1,3,4,5-tetrahydropyrido [4,3-b] indol-2-yl) methanone: Following GP3a, the title compound was obtained from 8-methyl-2,3,4,5-tetrahydro-1H-pyrido[4,3-b]indole (0.037 g, 0.20 mmol) and 3,5-dimethyl-1H-pyrazole-4-carboxylic acid (0.028 g, 0.20 mmol), after purification by silica gel flash-column chromatography with DCM/MeOH (95:5) as the eluent, as a white solid (0.010 g, 13%). $^1$H NMR (400 MHz, DMSO-d$_6$) δ 12.43 (s, 1H), 10.74 (s, 1H), 7.16 (app-d, J=8.2 Hz, 2H), 6.85 (dd, J=8.0, 1.7 Hz, 1H), 4.61 (br s, 2H), 3.83 (br s, 2H), 2.79 (br s, 2H), 2.33 (s, 3H), 2.16 (s, 3H), 2.08 (s, 3H); UPLC-MS: $t_R$=1.72 min (generic method); MS (ESI) m/z calcd for $C_{18}H_{21}N_4O$ (M+H)$^+$: 309.2, found: 309.2.

(8-Methyl-1, 3,4,5-tetrahydropyrido[4,3-b] indol-2-yl)-(5-phenyl-1H-pyrazol-3-yl)-methanone: Following GP3a, the title compound was obtained from 8-methyl-2,3,4,5-tetrahydro-1H-pyrido[4,3-b]indole (0.037 g, 0.20 mmol) and 5-phenyl-1H-pyrazole-3-carboxylic acid (0.038 g, 0.20 mmol), after purification by silica gel flash-column chromatography with DCM/EtOAc (7:3) as the eluent, as a white solid (0.040 g, 38%). $^1$H NMR showed the presence of conformers: $^1$H NMR (400 MHz, DMSO-d6) δ 13.79-13.27 (m, 1H), 10.78 (s, 1H), 8.01-7.69 (m, 2H), 7.57-7.31 (m, 3H), 7.31-7.11 (m, 2H), 7.12-6.97 (m, 1H), 6.96-6.79 (m, 1H), 5.29-4.50 (m, 2H), 4.40-3.76 (m, 2H), 3.04-2.78 (m, 2H), 2.35 (app-d, J=20.7 Hz, 3H); UPLC-MS: $t_R$=2.19 min (generic method); MS (ESI) m/z calcd for $C_{22}H_{21}N_4O$ (M+H)$^+$: 357.2, found: 357.2.

(8-Methyl-1, 3,4,5-tetrahydropyrido[4,3-b] indol-2-yl)-(1-phenylpyrazol-4-yl)methanone: Following GP3a, the title compound was obtained from 8-methyl-2,3,4,5-tetrahydro-1H-pyrido[4,3-b]indole (0.037 g, 0.20 mmol) and 1-phenylpyrazol-4-carboxylic acid (0.038 g, 0.20 mmol), after purification by silica gel flash-column chromatography with DCM/EtOAc (7:3) as the eluent, as a white solid (0.065 g, 69%). $^1$H NMR (400 MHz, DMSO-d$_6$) δ 10.80 (s, 1H), 8.89 (s, 1H), 8.07 (s, 1H), 7.98-7.87 (m, 2H), 7.59-7.48 (m, 2H), 7.42-7.31 (m, 1H), 7.23 (s, 1H), 7.18 (d, J=8.2 Hz, 1H), 6.86 (d, J=8.2 Hz, 1H), 4.83 (app-d, J=44.9 Hz, 2H), 3.98 (app-t, J=5.7 Hz, 2H), 2.92 (app-d, J=24.3 Hz, 2H), 2.35 (s, 3H); UPLC-MS: $t_R$=2.28 min (generic method); MS (ESI) m/z calcd for $C_{22}H_{21}N_4O$ (M+H)$^+$: 357.2, found: 357.2.

(5-Isopropyl-1H-pyrazol-3-yl)-(8-methoxy-1,3,4,5-tetrahydropyrido[4,3-b]indol-2-yl)-methanone: Following GP3a, the title compound was obtained from 8-methoxy-2,3,4,5-tetrahydro-1H-pyrido[4,3-b]indole (0.040 g, 0.20 mmol) and 5-isopropyl-1H-pyrazole-3-carboxylic acid (0.031 g, 0.20 mmol), after purification by silica gel flash-column chromatography with DCM/EtOAc (7:3) as the eluent, as a pink solid (0.052 g, 78%). $^1$H NMR showed the presence of conformers: $^1$H NMR (400 MHz, DMSO-d6) δ 12.94 (s, 1H), 10.73 (s, 1H), 7.19 (d, J=8.7 Hz, 1H), 6.88 (app-d, J=93.7 Hz, 1H), 6.69 (dd, J=8.8, 2.4 Hz, 1H), 6.60-6.31 (m, 1H), 4.94 (app-d, J=144.9 Hz, 2H), 4.29-4.15 (m, 1H), 4.08-3.87 (m, 1H), 3.78 (s, 3H), 3.14-2.81 (m, 3H), 1.26 (d, J=6.8 Hz, 6H); UPLC-MS: $t_R$=1.85 min (generic method); MS (ESI) m/z calcd for $C_{19}H_{23}N_9O_2$ (M+H)$^+$: 339.1, found: 339.2.

(8-Methoxy-1,3,4,5-tetrahydropyrido[4,3-b]indol-2-yl)(5-methyl-1H-pyrazol-3-yl)-methanone: Following GP3a, the title compound was obtained from 8-methoxy-2,3,4,5-tetrahydro-1H-pyrido[4,3-b]indole (0.040 g, 0.20 mmol) and 5-methyl-1H-pyrazole-3-carboxylic acid (0.25 g, 0.20 mmol), after purification by silica gel flash-column chromatography with DCM/MeOH (95:5) as the eluent, as an off-white solid (0.058 g, 95%). $^1$H NMR showed the presence of conformers: $^1$H NMR (400 MHz, DMSO-d$_6$) δ 12.86 (s, 1H), 10.72 (s, 1H), 7.18 (d, J=8.6 Hz, 1H), 6.87 (app-d, J=89.3 Hz, 1H), 6.72-6.61 (m, 1H), 6.57-6.27 (m, 1H), 4.90 (app-d, J=124.2 Hz, 2H), 4.18 (s, 1H), 3.97 (s, 1H), 3.90-3.56 (m, 3H), 2.99-2.72 (m, 2H), 2.34-2.11 (m, 3H); UPLC-MS: $t_R$=1.61 min (generic method); MS (ESI) m/z calcd for $C_{17}H_{19}N_4O_2$ (M+H)$^+$: 311.1, found: 311.1.

(8-Methoxy-1,3,4,5-tetrahydropyrido[4,3-b]indol-2-yl)-(1-phenylpyrazol-4-yl)methanone: Following general procedure 3a, the title compound was obtained from 8-methoxy-2,3,4,5-tetrahydro-1H-pyrido[4,3-b]indole (0.040 g, 0.20 mmol) and 1-phenylpyrazole-4-carboxylic acid (0.038 g, 0.20 mmol), after purification by silica gel flash-column chromatography with DCM/EtOAc (7:3) as the eluent, as a white solid (0.065 g, 92%). $^1$H NMR (400 MHz, DMSO-ds) δ 10.77 (s, 1H), 8.89 (s, 1H), 8.08 (s, 1H), 7.98-7.88 (m, 2H), 7.54 (dd, J=8.6, 7.3 Hz, 2H), 7.42-7.31 (m, 1H), 7.19 (d, J=8.7 Hz, 1H), 6.99 (s, 1H), 6.68 (dd, J=8.7, 2.4 Hz, 1H), 4.83 (app-d, J=42.1 Hz, 2H), 3.98 (app-t, J=5.7 Hz, 2H), 3.75 (s, 3H), 3.12-2.73 (s, 2H); UPLC-MS: $t_R$=2.06 min (generic method); MS (ESI) m/z calcd for $C_{22}H_{21}N_4O_2$ (M+H)$^+$: 373.2, found: 373.1.

(8-Methyl-1,3,4,5-tetrahydropyrido[4,3-b]indol-2-yl)-[1-methyl-5-(trifluoromethyl)pyrazol-3-yl]methanone: To a solution of 5-trifluoromethyl-1H-pyrazole-3-carboxylic acid (0.150 g, 0.8 mmol) in THF (4 mL) and DMF (4 mL) under nitrogen atmosphere, NaH (60% dispersion in mineral oil, 0.067 g, 1.68 mmol) was added at 0° C. Mixture was stirred for 10 min and MeI (60 µL, 0.96 mmol) was added, stirring for other 3 h at room temperature. Mixture was quenched with aqueous HCl 1M until pH 4-5. The aqueous layer was extracted with EtOAc (3×20 mL). Collected organic layers were washed with water (10 mL) and brine (10 mL), dried with Na$_2$SO$_4$, filtered and solvent evaporated to afford a crud product which was used in the next step without any further purification. Following GP3c the obtained carboxylic acid was coupled with 8-methyl-2,3,4,5-tetrahydro-1H-pyrido[4,3-b]indole. The title compound was obtained, after purification by silica gel flash-column chromatography with DCM/EtOAc (75:15) as the eluent, as a white solid (0.097 g, 18% overall). $^1$H-NMR showed the presence of conformers: $^1$H NMR (400 MHz, DMSO-d$_6$) 10.78 (s, 1H), 7.27-7.08 (m, 3H), 6.86 (app-t, J=8.7 Hz, 1H), 4.85 (app-d, J=69.3 Hz, 2H), 4.08 (t, J=5.9 Hz, 1H), 4.05 (s, 3H), 3.99 (t, J=5.6 Hz, 1H), 2.94-2.76 (m, 2H), 2.35 (app-d, J=14.9 Hz, 3H). UPLC-MS: $t_R$=2.31 min (Method A); MS (ESI) m/z calcd for $C_{18}H_{18}F_3N_4O$ (M+H)$^+$: 363.1, found: 363.2.

(5-Isopropyl-1H-pyrazol-3-yl)-(1,3,4,5-tetrahydropyrido[4,3-b]indol-2-yl)methanone: Following GP3b, the title compound was obtained from 2,3,4,5-tetrahydro-1H-pyrido[4,3-b]indole (0.033 g, 0.19 mmol) and 5-isopropyl-1H-pyrazole-3-carboxylic acid (0.03 g, 0.19 mmol), after purification by silica gel flash-column chromatography with DCM/EtOAc (8:2) as the eluent, as a white solid (0.013 g, 23%). $^1$H-NMR showed the presence of conformers: $^1$H NMR (400 MHz, DMSO-d$_6$): δ 12.92 (s, 1H), 10.90 (s, 1H), 7.44 (d, J=7.8 Hz, 1H), 7.30 (d, J=7.9 Hz, 1H), 7.09-6.88 (m, 2H), 6.41-6.30 (m, 1H), 5.20-5.11 (m, 1H), 4.83-4.71 (m, 1H), 4.29-4.19 (m, 1H), 4.00-3.95 (m, 1H), 3.05-2.94 (m, 1H), 2.94-2.82 (m, 2H), 1.24 (d, J=6.7 Hz, 6H). UPLC-MS: $t_R$=1.91 min (Method A); MS (ESI) m/z calcd for $C_{18}H_{21}N_4O$ (M+H)$^+$: 309.2, found: 309.2.

[6-(Dimethylamino)-1H-indol-2-yl]-(8-methoxy-1,3,4,5-tetrahydropyrido [4,3-b] indol-2-yl) methanone: Following GP3c, the title compound was obtained from 8-methoxy-2,3,4,5-tetrahydro-1H-pyrido[4,3-b]indole (0.025 g, 0.12 mmol) and 6-(dimethylamino)-1H-indole-2-carboxylic acid (0.025 g, 0.12 mmol), after purification by silica gel flash-column chromatography with DCM/EtOAc (50:50) as the eluent, as a white solid (0.023 g, 50%). $^1$H NMR (400 MHz, DMSO-d$_6$) δ 11.09 (s, 1H), 10.76 (s, 1H), 7.45 (d, J=8.8 Hz, 1H), 7.18 (d, J=8.7 Hz, 1H), 6.96 (d, J=2.4 Hz, 1H), 6.85 (s, 1H), 6.73 (dd, J=8.9, 2.3 Hz, 1H), 6.66 (dd, J=8.7, 2.4 Hz, 1H), 6.63 (d, J=2.2 Hz, 1H), 4.89 (bs, 2H), 4.05 (s, 2H), 3.74 (s, 3H), 2.93 (bs, 2H), 2.90 (s, 6H). UPLC-MS: $t_R$=2.17 min (Method A); MS (ESI) m/z calcd for $C_{23}H_{25}N_4O_2$ (M+H)$^+$: 389.2, found: 389.2.

2-(5-Bromo-2-furoyl)-8-methoxy-2,3,4,5-tetrahydro-1H-pyrido[4,3-b]indole: Following GP3c, the title compound was obtained from 8-methoxy-2,3,4,5-tetrahydro-1H-pyrido[4,3-b]indole (0.063 g, 0.26 mmol) and 5-bromofuran-2-carboxylic acid (0.050 g, 0.26 mmol), after purification by silica gel flash-column chromatography with cyclohexane/EtOAc (8:2) as the eluent, as an off-white solid (0.076 g, 77%). $^1$H NMR (400 MHz, DMSO-d6) δ 10.77 (s, 1H), 7.18 (d, J=8.7 Hz, 1H), 7.14 (d, J=3.6 Hz, 1H), 6.95 (br s, 1H), 6.80 (d, J=3.5 Hz, 1H), 6.68 (dd, J=8.7, 2.5 Hz, 1H), 4.77 (br s, 2H), 3.97 (app-t, J=5.6 Hz, 2H), 3.75 (s, 3H), 2.90 (br s, 2H); UPLC-MS: $t_R$=2.07 min (generic method); MS (ESI) m/z calcd for $C_{17}H_{16}BrN_2O_3$ (M+H)$^+$: 375.0, found: 375.1.

(5-Bromo-2-furyl)-(8-methyl-1,3,4,5-tetrahydropyrido[4,3-b]indol-2-yl)methanone: Following GP3c, the title compound was obtained from 8-methyl-2,3,4,5-tetrahydro-1H-pyrido[4,3-b]indole (0.050 g, 0.27 mmol) and 5-bromofuran-2-carboxylic acid (0.052 g, 0.27 mmol), after purification by silica gel flash-column chromatography with DCM/EtOAc (90:10) as the eluent, as a white solid (0.058 g, 60%). $^1$H NMR (400 MHz, DMSO-d6) δ 10.80 (s, 1H), 7.26-7.15 (m, 2H), 7.13 (d, J=3.5 Hz, 1H), 6.87 (dd, J=8.2, 1.6 Hz, 1H), 6.79 (d, J=3.5 Hz, 1H), 4.78 (bs, 2H), 3.97 (t, J=5.7 Hz, 2H), 2.90 (bs, 2H), 2.35 (s, 3H). UPLC-MS: $t_R$=2.30 min (Method A); MS (ESI) m/z calcd for $C_{17}H_{16}BrN_2O_2$ (M+H)$^+$: 359.0, found: 359.0.

(8-Methyl-1,3,4,5-tetrahydropyrido[4,3-b] indol-2-yl)-[5-(trifluoromethyl)-2-furyl]-methanone: Following GP3c, the title compound was obtained from 8-methyl-2,3,4,5-tetrahydro-1H-pyrido[4,3-b]indole (0.050 g, 0.27 mmol) and 5-trifluoromethyl-2-carboxylic acid (0.048 g, 0.27 mmol), after purification by silica gel flash-column chromatography with DCM/EtOAc (90:10) as the eluent, as a white solid (0.078 g, 83%). $^1$H-NMR showed the presence of conformers: $^1$H NMR (400 MHz, DMSO-d6) δ 10.83 (s, 1H), 7.43 (dq, J=3.7, 1.2 Hz, 1H), 7.35-7.07 (m, 3H), 6.88 (dd, J=8.2, 1.6 Hz, 1H), 4.81 (app-d, J=40.3 Hz, 2H), 3.98 (s, 2H), 3.10-2.80 (m, 2H), 2.36 (s, 3H). UPLC-MS: $t_R$=2.41 min (Method A); MS (ESI) m/z calcd for $C_{18}H_{16}F_3N_2O_2$ (M+H)$^+$: 349.1, found: 349.1.

(4-Bromo-2-furyl)-(8-methyl-1, 3,4,5-tetrahydropyrido[4,3-b]indol-2-yl)methanone: Following GP3c, the title compound was obtained from 8-methyl-2,3,4,5-tetrahydro-1H-pyrido[4,3-b]indole (0.050 g, 0.27 mmol) and 4-bromofuran-2-carboxylic acid (0.051 g, 0.27 mmol), after purification by silica gel flash-column chromatography with DCM/EtOAc (90:10) as the eluent, as a white solid (0.068 g, 70%). $^1$H NMR (400 MHz, DMSO-d6) δ 10.81 (s, 1H), 8.14 (d, J=0.8 Hz, 1H), 7.28 (s, 1H), 7.21 (s, 1H), 7.19 (d, J=8.2 Hz, 1H), 6.87 (dd, J=8.2, 1.6 Hz, 1H), 5.04-4.57 (m, 2H), 3.97 (t, J=5.7 Hz, 2H), 2.91 (bs, 2H), 2.36 (s, 3H). UPLC-MS: $t_R$=2.31 min (Method A); MS (ESI) m/z calcd for $C_{17}H_{16}BrN_2O_2$ (M+H)$^+$: 359.0, found: 359.0.

(8-Methoxy-1,3,4,5-tetrahydropyrido[4,3-b]indol-2-yl)-(1H-pyrazol-3-yl)methanone: Following GP3c, the title compound was obtained from 8-methoxy-2,3,4,5-tetrahydro-1H-pyrido[4,3-b]indole (0.070 g, 0.35 mmol) and 1H-pyrazole-3-carboxylic acid (0.039 g, 0.35 mmol), after purification by silica gel flash-column chromatography with DCM/EtOAc (55:45) as the eluent, as a white solid (0.030 g, 30%). $^1$H-NMR showed the presence of conformers: $^1$H NMR (400 MHz, DMSO-d$_6$) δ 13.21 (s, 1H), 10.74 (s, 1H), 7.82 (s, 1H), 7.18 (d, J=8.6 Hz, 1H), 7.07-6.72 (m, 1H), 6.72-6.53 (m, 2H), 5.19-4.66 (m, 2H), 4.16 (s, 1H), 4.07-3.93 (m, 1H), 3.74 (app-d, J=18.0 Hz, 3H), 3.01-2.75 (m, 2H). UPLC-MS: $t_R$=1.52 min (Method A); MS (ESI) m/z calcd for $C_6H_{17}N_4O_2$ (M+H)$^+$: 297.1, found: 297.2.

(8-Methoxy-1,3,4,5-tetrahydropyrido[4,3-b]indol-2-yl)-(5-phenyl-1H-pyrazol-3-yl)-methanone: Following GP3c, the title compound was obtained from 8-methoxy-2,3,4,5-tetrahydro-1H-pyrido[4,3-b]indole (0.030 g, 0.15 mmol) and 5-phenyl-1H-pyrazole-3-carboxylic acid (0.028 g, 0.15 mmol), after purification by silica gel flash-column chromatography with DCM/EtOAc (50:50) as the eluent, as a white solid (0.016 g, 29%). $^1$H NMR showed the presence of conformers: $^1$H NMR (400 MHz, DMSO-d$_6$) δ 13.66 (s, 1H), 10.76 (s, 1H), 7.84 (app-d, J=7.5 Hz, 2H), 7.47 (app-t, J=7.6 Hz, 2H), 7.42-7.32 (m, 1H), 7.19 (d, J=8.6 Hz, 1H), 7.08 (s, 1H), 7.04-6.76 (m, 1H), 6.73-6.59 (m, 1H), 5.22-4.60 (m, 2H), 4.39-3.92 (m, 2H), 3.74 (app-d, J=23.1 Hz, 3H), 2.91 (app-d, J=28.6 Hz, 2H). UPLC-MS: $t_R$=2.00 min (Method A); MS (ESI) m/z calcd for $C_{22}H_{21}N_4O_2$ (M+H)$^+$: 373.2, found: 373.2.

(8-Methoxy-1, 3,4,5-tetrahydropyrido [4,3-b] indol-2-yl)-[2-(trifluoromethyl)-1H-imidazol-4-yl]methanone: Following GP3c, the title compound was obtained from 8-methoxy-2,3,4,5-tetrahydro-1H-pyrido[4,3-b]indole (0.030 g, 0.15 mmol) and 2-(trifluoromethyl)-1H-imidazole-4-carboxylic acid (0.027 g, 0.15 mmol), after purification by silica gel flash-column chromatography with DCM/EtOAc (60:40) as the eluent, as a white solid (0.022 g, 40%). $^1$H-NMR showed the presence of conformers: $^1$H NMR (400 MHz, DMSO-d6) δ 14.10 (s, 1H), 10.74 (s, 1H), 7.90 (s, 1H), 7.18 (d, J=8.7 Hz, 1H), 7.07-6.73 (m, 1H), 6.67 (dd, J=8.7, 2.4 Hz, 1H), 5.28-4.60 (m, 2H), 4.42-3.85 (m, 2H), 3.75 (s, 3H), 3.03-2.77 (m, 2H). UPLC-MS: $t_R$=1.69 min (Method A); MS (ESI) m/z calcd for $C_{17}H_{16}F_3N_4O_2$(M+H)$^+$: 365.1, found: 365.1.

2-Furyl-(8-methyl-1, 3,4,5-tetrahydropyrido[4,3-b]indol-2-yl)methanone: Following GP3c, the title compound was obtained from 8-methyl-2,3,4,5-tetrahydro-1H-pyrido[4,3-b]indole (0.050 g, 0.27 mmol) and furan-2-carboxylic acid (0.030 g, 0.27 mmol), after purification by silica gel flash-column chromatography with DCM/EtOAc (90:10) as the eluent, as a white solid (0.058 g, 76%). $^1$H NMR (400 MHz, DMSO-d$_6$) δ 10.80 (s, 1H), 7.88 (dd, J=1.8, 0.8 Hz, 1H), 7.23-7.14 (m, 2H), 7.08 (d, J=3.3 Hz, 1H), 6.86 (dd, J=8.2, 1.7 Hz, 1H), 6.66 (dd, J=3.5, 1.8 Hz, 1H), 4.80 (bs, 2H), 3.99 (t, J=5.3 Hz, 2H), 2.90 (bs, 2H), 2.35 (s, 3H). UPLC-MS: $t_R$=2.07 min (Method A); MS (ESI) m/z calcd for $C_{17}H_{17}N_2O_2$ (M+H)$^+$: 281.1, found: 281.1.

(5-tert-Butyl-1H-pyrazol-3-yl)-(8-methyl-1,3,4,5-tetrahydropyrido[4,3-b]indol-2-yl)-methanone: Following GP3c, the title compound was obtained from 8-Methyl-2,3,4,5-tetrahydro-1H-pyrido[4,3-b]indole (0.050 g, 0.27 mmol) and 5-tert-Butyl-1H-pyrazole-3-carboxylic acid (0.045 g, 0.27 mmol), after purification by silica gel flash-column chromatography with DCM/EtOAc (8:2) as the eluent, as a white solid (0.046 g, 51%). $^1$H NMR (400 MHz, DMSO-d$_6$): δ 12.96 (s, 1H), 10.76 (s, 1H), 7.29-7.01 (m, 2H), 6.94-6.82 (m, 1H), 6.42-6.28 (m, 1H), 5.16 (bs, 1H), 4.75 (bs, 1H), 4.29-4.15 (m, 1H), 4.02-3.95 (m, 1H), 2.98-2.79 (m, 2H), 2.43-2.29 (m, 3H), 1.31 (s, 9H). UPLC-MS: $t_R$=2.16 min (Method A); MS (ESI) m/z calcd for $C_{20}H_{25}N_4O$ (M+H)$^+$: 337.2, found: 337.2.

1H-Indol-2-yl-(1,3,4,5-tetrahydropyrido[4,3-b]indol-2-yl)methanone: Following GP3a, the title compound was obtained from 2,3,4,5-tetrahydro-1H-pyrido[4,3-b]indole (0.050 g, 0.31 mmol) and 1H-Indole-2-carboxylic acid (0.053 g, 0.31 mmol), after purification by preparative LC/MS, as a white solid (0.021 g, 32%). $^1$H NMR (400 MHz, DMSO-d$_6$): δ 11.62 (s, 1H), 10.98 (s, 1H), 7.66 (dt, J=8.0, 1.0 Hz, 1H), 7.48-7.40 (m, 2H), 7.32 (d, J=8.0 Hz, 1H), 7.20 (ddd, J=8.2, 7.0, 1.2 Hz, 1H), 7.14-7.01 (m, 2H), 6.98 (d, J=5.4 Hz, 2H), 4.95 (s, 2H), 4.12 (d, J=6.9 Hz, 2H), 3.00 (s, 2H). UPLC-MS: $t_R$=2.24 min (Method A); MS (ESI) m/z calcd for $C_{20}H_{18}N_3O$ (M+H)$^+$: 316.1, found: 316.3.

(5-Cyclopropyl-1H-pyrazol-3-yl)-(8-methyl-1,3,4,5-tetrahydropyrido[4,3-b]indol-2-yl)methanone: Following GP3c, the title compound was obtained from 8-Methyl-2,3,4,5-tetrahydro-1H-pyrido[4,3-b]indole (0.050 g, 0.27 mmol) and 5-Cyclopropyl-1H-pyrazole-3-carboxylic acid (0.041 g, 0.27 mmol), after purification by silica gel flash-column chromatography with DCM/EtOAc (8:2) as the eluent, as a white solid (0.042 g, 48%). $^1$H NMR (400 MHz, DMSO-d$_6$): δ 12.98 (d, J=38.2 Hz, 1H), 10.76 (s, 1H), 7.33-6.99 (m, 2H), 6.94-6.77 (m, 1H), 6.40-6.17 (m, 1H), 5.07 (s, 1H), 4.74 (s, 1H), 4.24-4.10 (m, 1H), 3.99-3.87 (m, 1H), 3.01-2.76 (m, 2H), 2.45-2.33 (m, 3H), 1.99-1.87 (m, 1H), 1.02-0.88 (m, 2H), 0.80-0.66 (m, 2H). UPLC-MS: $t_R$=1.98 min (Method A); MS (ESI) m/z calcd for $C_{19}H_{21}N_4O$ (M+H)$^+$: 321.2, found: 321.3.

(8-Methyl-1,3,4,5-tetrahydropyrido[4,3-b]indol-2-yl)-[3-(trifluoromethyl)-1H-pyrazol-4-yl]-methanone: Following GP3c, the title compound was obtained from 8-Methyl-2,3,4,5-tetrahydro-1H-pyrido[4,3-b]indole (0.06 g, 0.27 mmol) and 3-(Trifluoromethyl)-1H-pyrazole-4-carboxylic acid (0.049 g, 0.27 mmol), after purification by silica gel flash-column chromatography with DCM/EtOAc (75:25) as the eluent, as a white solid (0.036 g, 39%). $^1$H NMR (400 MHz, DMSO-d6): δ 13.95 (s, 1H), 10.79 (s, 1H), 8.38-8.21 (m, 1H), 7.33-6.98 (m, 2H), 7.01-6.73 (m, 1H), 4.81-4.67 (m, 1H), 4.61-4.47 (m, 1H), 4.11-3.89 (m, 1H), 3.75-3.59 (m, 1H), 2.97-2.75 (m, 2H), 2.45-2.19 (m, 3H). UPLC-MS: $t_R$=1.97 min (Method A); MS (ESI) m/z calcd for $C_{17}H_{16}F_3N_4O$ (M+H)$^+$: 349.1, found: 349.1.

(8-Methyl-1, 3,4,5-tetrahydropyrido[4,3-b]indol-2-yl)-[5-(trifluoromethyl)-2-pyridyl]-methanone: Following GP3c, the title compound was obtained from 8-methyl-2,3,4,5-tetrahydro-1H-pyrido[4,3-b]indole (0.050 g, 0.27 mmol) and 5-(trifluoromethyl)pyridine-2-carboxylic acid (0.051 g, 0.27 mmol), after purification by silica gel flash-column chromatography with DCM/EtOAc (90:10) as the eluent, as a white solid (0.069 g, 71%). $^1$H-NMR showed the presence of conformers. Major conformer: $^1$H NMR (400 MHz, DMSO-d$_6$) δ 10.80 (s, 1H), 9.07-9.03 (m, 1H), 8.41-8.37 (m, 1H), 7.87 (dt, J=8.2, 0.8 Hz, 1H), 7.28-7.24 (m, 1H), 7.20 (d, J=8.2 Hz, 1H), 6.88 (dd, J=8.2, 1.6 Hz, 1H), 4.83 (s, 1H), 3.66 (t, J=5.7 Hz, 2H), 2.84 (t, J=5.7 Hz, 2H), 2.38 (s, 3H); Minor conformer: $^1$H NMR (400 MHz, DMSO-ds) δ 10.81 (s, 1H), 9.09-9.00 (m, 1H), 8.37-8.32 (m, 1H), 7.81 (dt, J=8.2, 0.8 Hz, 1H), 7.16 (d, J=8.2 Hz, 1H), 7.00 (d, J=1.6 Hz, 1H), 6.83 (dd, J=8.3, 1.6 Hz, 1H), 4.55 (t, J=1.4 Hz, 2H), 4.06 (t, J=5.8 Hz, 2H), 2.91 (t, J=5.8 Hz, 2H), 2.28 (s, 3H). UPLC-MS: $t_R$=2.30 min (Method A); MS (ESI) m/z calcd for $C_{19}H_{17}F_3N_3O$ (M+H)$^+$: 360.1, found: 360.2.

(8-Methyl-1, 3,4,5-tetrahydropyrido[4,3-b] indol-2-yl)-[6-(trifluoromethyl)-1H-indol-2-yl]methanone: Following GP3c, the title compound was obtained from 8-methyl-2,3,4,5-tetrahydro-1H-pyrido[4,3-b]indole (0.050 g, 0.27 mmol) and 6-(trifluoromethyl)-1H-indole-2-carboxylic acid (0.061 g, 0.27 mmol), after purification by silica gel flash-column chromatography with DCM/EtOAc (90:10) as the eluent, as a white solid (0.078 g, 73%). $^1$H-NMR showed the presence of conformers: $^1$H NMR (400 MHz, DMSO-d$_6$) δ 12.11 (s, 1H), 10.83 (s, 1H), 7.88 (d, J=8.4 Hz, 1H), 7.76 (s, 1H), 7.36 (dd, J=8.5, 1.6 Hz, 1H), 7.29-7.15 (m, 2H), 7.10 (bs, 1H), 6.87 (d, J=8.2 Hz, 1H), 5.25-4.56 (m, 2H), 4.10 (s, 2H), 2.97 (bs, 2H), 2.35 (s, 3H). UPLC-MS: $t_R$=2.63 min (Method A); MS (ESI) m/z calcd for $C_{22}H_{19}F_3N_3O$ (M+H)$^+$: 398.1, found: 398.2.

(8-Isopropyl-1,3,4,5-tetrahydropyrido[4,3-b]indol-2-yl)-[5-(trifluoromethyl)-1H-pyrazol-3-yl]-methanone: Following GP3c, the title compound was obtained from [Int-2.22] (0.060 g, 0.24 mmol) and 5-(trifluoromethyl)-1H-pyrazole-3-carboxylic acid (0.047 g, 0.26 mmol), after purification by silica gel flash-column chromatography with DCM/EtOAc (80:20) as the eluent, as a white solid (0.056 g, 62%). $^1$H-NMR showed the presence of conformers. $^1$H NMR (400 MHz, DMSO-d6) δ 14.38 (s, 1H), 10.82 (s, 1H), 7.37-7.14 (m, 3H), 6.95 (d, J=8.2 Hz, 1H), 4.83 (app-d, J=27.1 Hz, 2H), 3.96 (app-d, J=33.3 Hz, 2H), 3.08-2.81 (m, 3H), 1.31-1.20 (m, 6H). UPLC-MS: $t_R$=2.43 min (Method A); MS (ESI) m/z calcd for $C_{19}H_{20}F_3N_4O$ (M+H)$^+$: 377.2, found: 377.2.

(6-Methyl-1,3,4,5-tetrahydropyrido[4,3-b]indol-2-yl)-[5-(trifluoromethyl)-1H-pyrazol-3-yl]-methanone: Following GP3c, the title compound was obtained from [Int-2.23] (0.06 g, 0.27 mmol) and 5-(trifluoromethyl)-1H-pyrazole-3-carboxylic acid (0.053 g, 0.30 mmol), after purification by silica gel flash-column chromatography with DCM/EtOAc (85:15) as the eluent, as a white solid (0.040 g, 42%). $^1$H-NMR showed the presence of conformers: $^1$H NMR (400 MHz, DMSO-d6) δ 14.39 (s, 1H), 10.90 (s, 1H), 7.50-7.08 (m, 2H), 7.11-6.64 (m, 2H), 4.84 (app-d, J=30.8 Hz, 2H), 3.99 (app-d, J=38.2 Hz, 2H), 2.96 (app-d, J=31.2 Hz, 2H), 2.44 (s, 3H). UPLC-MS: $t_R$=2.19 min (Method A); MS (ESI) m/z calcd for $C_{17}H_{16}F_3N_4O$ (M+H)$^+$: 349.2, Found: 349.2.

(8-Fluoro-1,3,4,5-tetrahydropyrido[4,3-b]indol-2-yl)-[5-(trifluoromethyl)-1H-pyrazol-3-yl]methanone: Following GP3c, the title compound was obtained from 8-fluoro-2,3,4,5-tetrahydro-1H-pyrido[4,3-b]indole (0.050 g, 0.26 mmol) and 5-(trifluoromethyl)-1H-pyrazole-3-carboxylic acid (0.047 g, 0.26 mmol), after purification by silica gel flash-column chromatography with DCM/EtOAc (80:20) as the eluent, as a white solid (0.012 g, 13%). $^1$H NMR (400 MHz, DMSO-d$_6$): δ 14.39 (s, 1H), 11.10 (s, 1H), 7.38-7.12 (m, 3H), 6.88 (s, 1H), 4.96-4.72 (m, 2H), 4.16-3.84 (m, 2H), 3.05-2.85 (m, 2H). UPLC-MS: $t_R$=2.08 min (Method A); MS (ESI) m/z calcd for $C_{16}H_{13}F_4N_4O$ (M+H)$^+$: 353.2, found: 353.2.

(2-Methyl-5,6,7,8,9,10-hexahydro-7,10-epimino cyclohepta[b]indol-11-yl) (5-(trifluoromethyl)-1H-pyrazol-3-yl)methanone: Following GP3b, the title compound was obtained from [Int-2.11] (0.070 g, 0.28 mmol) and 5-(trifluoromethyl)-1H-pyrazole-3-carboxylic acid (0.061 g, 0.34 mmol), after purification by silica gel flash-column chromatography with DCM/EtOAc (70:30) as the eluent, as a white solid (0.070 g, 67%). $^1$H NMR (400 MHz, DMSO-d$_6$) δ 14.35 (s, 1H), 10.80 (app-d, J=8.5 Hz, 1H), 7,32 and 7.01 (s, 1H), 7.28 (s, 1H), 7.16 (dd, J=8.2, 4.1 Hz, 1H), 6.85 (d, J=8.3 Hz, 1H), 5.81-5.47 (m, 1H), 4.95 (app-d, J=42.0 Hz, 1H), 3.51-3.33 (m, 1H), 2.71 (t, J=16.5 Hz, 1H), 2.37 (app-d, J=10.0 Hz, 3H), 2.34-2.17 (m, 1H), 2.15-1.87 (m, 2H), 1.74 (s, 1H). UPLC-MS: $t_R$=2.28 min (Method A); MS (ESI) m/z calcd for $C_{19}H_{18}F_3N_4O$ (M+H)$^+$: 375.1, found: 375.2.

(1H-Indol-2-yl) (2-methyl-5,6,7,8,9,10-hexahydro-7,10-epiminocyclohepta[b]indol-11-yl)methanone: Following GP3c, the title compound was obtained from [Int-2.11] (0.100 g, 0.40 mmol) and 1H-indole-2-carboxylic acid (0.065 g, 0.40 mmol), after purification by silica gel flash-column chromatography with DCM/EtOAc (80:20) as the eluent, as a white solid (0.072 g, 49%). $^1$H NMR (400 MHz, DMSO-d$_6$): δ 11.79-11.20 (m, 1H), 10.79 (s, 1H), 7.72-7.49 (m, 1H), 7.50-7.36 (m, 1H), 7.32 (s, 1H), 7.25-7.13 (m, 2H), 7.11-6.94 (m, 1H), 6.93-6.72 (m, 1H), 5.98-5.32 (m, 1H), 5.32-4.75 (m, 1H), 3.53-3.41 (m, 2H), 3.07-2.64 (m, 1H), 2.38 (s, 3H), 2.36-2.16 (m, 1H), 2.16-1.86 (m, 2H), 1.81-1.67 (m, 1H). UPLC-MS: $t_R$=2.44 min (Method A); MS (ESI) m/z calcd for $C_{23}H_{22}N_3O$ (M+H)$^+$: 356.2, found: 356.2.

(5-Bromofuran-2-yl) (2-methyl-5, 6,7,8,9,10-hexahydro-7,10-epiminocyclohepta[b]indol-11-yl)methanone: Following GP3c, the title compound was obtained from [Int-2.11] (0.070 g, 0.28 mmol) and 5-bromofuran-2-carboxylic acid (0.053 g, 0282 mmol), after purification by silica gel flash-column chromatography with DCM/EtOAc (80:20) as the eluent, as a white solid (0.053 g, 49%). $^1$H NMR (400 MHz, DMSO-d6): δ 10.77 (s, 1H), 7.29 (s, 1H), 7.21-6.92 (m, 2H), 6.84 (dd, J=8.2, 1.6 Hz, 1H), 6.80-6.65 (m, 1H), 5.91-5.49 (m, 1H), 5.01 (d, J=27.0 Hz, 1H), 2.83-2.58 (m, 1H), 2.37 (s, 3H), 2.32-2.10 (m, 2H), 2.04-1.84 (m, 2H), 1.81-1.64 (m, 1H). UPLC-MS: $t_R$=2.40 min (Method A); MS (ESI) m/z calcd for $C_{19}H_{18}BrN_2O_2$ (M+H)$^+$: 385.0, found: 385.7.

(8-Methyl-1, 3,4,5-tetrahydropyrido[4,3-b] indol-2-yl)-[6-(trifluoromethyl)-2-pyridyl]methanone: Following GP3c, the title compound was obtained from 8-methyl-2,3,4,5-tetrahydro-1H-pyrido[4,3-b]indole hydrochloride (0.056 g, 0.30 mmol) and 6-(trifluoromethyl)pyridine-2-carboxylic acid (0.057 g, 0.30 mmol), after purification by silica gel flash-column chromatography with DCM/EtOAc (80:20) as the eluent, as a white solid (0.055 g, 12%). $^1$H NMR (400 MHz, DMSO-d$_6$)): 10.81 (d, J=8.2 Hz, 1H), 8.25 (dt, J=12.6, 7.7 Hz, 1H), 8.03 (dd, J=7.7, 3.9 Hz, 1H), 7.94 (dd, J=28.2, 7.8 Hz, 1H), 7.26 (s, 1H), 7.19 (dd, J=13.8, 8.1 Hz, 1H), 6.88

(dt, J=21.4, 10.5 Hz, 1H), 4.92-4.71 (m, 1H), 4.64-4.37 (m, 1H), 4.22-3.97 (m, 1H), 3.69-3.60 (m, 1H), 2.58-2.45 (m, 1H), 2.37 (s, 3H), 2.33-2.21 (m, 1H). UPLC-MS: $t_R$=2.30 min (Method A); MS (ESI) m/z calcd for $C_{19}H_{17}F_3N_3O$ (M+H)$^+$: 360.1, found: 360.2.

(6-Fluoro-9-methyl-1, 3,4,5-tetrahydropyrido [4,3-b]indol-2-yl]-[5-(trifluoromethyl)-1H-pyrazol-3-yl]methanone: Following GP3c, the title compound was obtained from [Int-2.2] (0.1 g, 0.42 mmol) and 5-(trifluoromethyl)-1H-pyrazole-3-carboxylic acid (0.076 g, 0.42 mmol), after purification by silica gel flash-column chromatography with DCM/EtOAc (80:20) as the eluent, as a white solid (0.031 g, 20%). $^1$H NMR (400 MHz, DMSO-d$_6$): δ 14.42 (s, 1H), 11.39 (s, 1H), 7.20 (s, 1H), 6.73 (t, J=9.6 Hz, 1H), 6.66 (s, 1H), 5.09 (d, J=35.3 Hz, 2H), 4.25-3.84 (m, 2H), 2.93 (d, J=31.2 Hz, 2H), 2.55 (s, 3H). UPLC-MS: $t_R$=2.22 min (Method A); MS (ESI) m/z calcd for $C_{17}H_{15}F_4N_4O$ (M+H)$^+$: 367.2, found: 367.3.

[8-(Trifluoromethoxy)-1,3,4,5-tetrahydropyrido[4,3-b]indol-2-yl]-[5-(trifluoromethyl)-1H-pyrazol-3-yl]methanone: Following GP3a, the title compound was obtained from [Int-2.26] (0.051 g, 0.20 mmol) and 5-(trifluoromethyl)-1H-pyrazole-3-carboxylic acid (0.036 g, 0.20 mmol), after purification by silica gel flash-column chromatography with DCM/EtOAc (7:3) as the eluent, as a white solid (0.072 g, 88%). $^1$H NMR (400 MHz, DMSO-d$_6$) δ 14.38 (s, 1H), 11.29 (s, 1H), 7.51 (s, 1H), 7.38 (d, J=8.7 Hz, 1H), 7.25 (d, J=39.2 Hz, 1H), 7.01 (d, J=8.7 Hz, 1H), 4.86 (app-d, J=35.4 Hz, 2H), 3.98 (app-d, J=34.4 Hz, 2H), 2.96 (app-d, J=38.7 Hz, 2H); UPLC-MS: $t_R$=2.33 min (generic method); MS (ESI) m/z calcd for $C_{17}H_{13}F_6N_4O_2$ (M+H)$^+$: 419.1, found: 419.2.

(8-Bromo-1,3,4,5-tetrahydropyrido[4,3-b]indol-2-yl)-[5-(trifluoromethyl)-1H-pyrazol-3-yl]methanone: Following GP3a, the title compound was obtained from [Int-2.25] (0.05 g, 0.2 mmol) and 5-(trifluoromethyl)-1H-pyrazole-3-carboxylic acid (0.036 g, 0.2 mmol), after purification by silica gel flash-column chromatography with DCM/EtOAc (7:3) as the eluent, as a white solid (0.068 g, 92%). $^1$H NMR (400 MHz, DMSO-d6) δ 14.37 (s, 1H), 11.21 (s, 1H), 7.70 (s, 1H), 7.35-7.09 (m, 3H), 4.84 (app-d, J=38.0 Hz, 2H), 3.97 (app-d, J=36.1 Hz, 2H), 2.94 (app-d, J=35.8 Hz, 2H); UPLC-MS: $t_R$=2.26 min (generic method); MS (ESI) m/z calcd for $C_{16}H_{13}BrF_3N_4O$ (M+H)$^+$: 413.0, found: 413.1.

[5-(Trifluoromethyl)-1H-pyrazol-3-yl]-(4,4,8-trimethyl-3,5-dihydro-1H-pyrido [4,3-b] indol-2-yl)methanone: Following general procedure 3a, the title compound was obtained from [Int-2.31] (0.043 g, 0.20 mmol) and 5-(trifluoromethyl)-1H-pyrazole-3-carboxylic acid (0.036 g, 0.20 mmol), after purification by silica gel flash-column chromatography with DCM/EtOAc (9:1) as the eluent, as an off-white solid (0.032 g, 58%). $^1$H NMR showed the presence of conformers: $^1$H NMR (400 MHz, DMSO-d6) δ 14.39 (s, 1H), 10.85 (s, 1H), 7.39-7.03 (m, 3H), 6.87 (app-d, J=8.4 Hz, 1H), 5.01-4.64 (m, 2H), 3.96-3.45 (m, 2H), 2.44-2.23 (m, 3H), 1.33 (s, 3H), 1.24 (s, 3H); UPLC-MS: $t_R$=2.35 min (generic method); MS (ESI) m/z calcd for $C_{19}H_{20}F_3N_4O$ (M+H)$^+$: 377.2, found: 377.2.

[5-(trifluoromethyl)-1H-pyrazol-3-yl]-[8-(trifluoromethyl)-1,3,4,5-tetrahydropyrido[4,3-b]indol-2-yl]methanone: Following GP3c, the title compound was obtained from [Int-2.3] (0.1 g, 0.42 mmol) and 5-(trifluoromethyl)-1H-pyrazole-3-carboxylic acid (0.075 g, 0.42 mmol), after purification by silica gel flash-column chromatography with DCM/EtOAc (80:20) as the eluent, as a white solid (0.038 g, 22%). $^1$H NMR (400 MHz, DMSO-d6): δ 14.38 (s, 1H), 11.48 (d, J=6.3 Hz, 1H), 7.93 (s, 1H), 7.50 (t, J=6.8 Hz, 1H), 7.42-7.10 (m, 2H), 4.92 (d, J=36.6 Hz, 2H), 4.00 (d, J=32.1 Hz, 2H), 2.98 (d, J=35.7 Hz, 2H). UPLC-MS: $t_R$=2.26 min (Method A); MS (ESI) m/z calcd for $C_{17}H_{13}F_6N_4O$ (M+H)$^+$: 403.1, found: 403.3.

(6,8-Methyl-1,3,4,5-tetrahydropyrido[4,3-b]indol-2-yl)-[5-(trifluoromethyl)-1H-pyrazol-3-yl]methanone: Following GP3c, the title compound was obtained from [Int-2.5] (0.085 g, 0.36 mmol) and 5-(trifluoromethyl)-1H-pyrazole-3-carboxylic acid (0.065 g, 0.36 mmol), after purification by preparative LC/MS, as a white solid (0.031 g, 24%). $^1$H NMR (400 MHz, DMSO-d$_6$): δ 14.39 (s, 1H), 10.76 (s, 1H), 7.23 (d, J=29.1 Hz, 1H), 7.05 (d, J=16.4 Hz, 1H), 6.69 (s, 1H), 4.81 (d, J=30.4 Hz, 2H), 3.98 (d, J=37.0 Hz, 2H), 2.94 (d, J=30.5 Hz, 2H), 2.39 (s, 3H), 2.33 (d, J=10.9 Hz, 3H). UPLC-MS: $t_R$=2.31 min (Method A); MS (ESI) m/z calcd for $C_{18}H_{18}F_3N_4O$ (M+H)$^+$: 363.1, found: 363.2. [050] (6-Fluoro-1,3,4,5-tetrahydropyrido[4,3-b]indol-2-yl)-[5-(trifluoromethyl)-1H-pyrazol-3-yl]methanone: Following GP3a, the title compound was obtained from [Int-2.27] (0.038 g, 0.20 mmol) and 5-(trifluoromethyl)-1H-pyrazole-3-carboxylic acid (0.036 g, 0.20 mmol), after purification by silica gel flash-column chromatography with DCM/EtOAc (8:2) as the eluent, as a white solid (0.052 g, 92%). $^1$H NMR (400 MHz, DMSO-d$_6$) δ 14.38 (s, 1H), 11.46 (s, 1H), 7.37-7.12 (m, 2H), 7.04-6.74 (m, 2H), 4.85 (app-d, J=32.5 Hz, 2H), 3.98 (app-d, J=36.6 Hz, 2H), 2.95 (app-d, J=36.5 Hz, 2H); UPLC-MS: $t_R$=2.12 min (generic method); MS (ESI) m/z calcd for $C_{16}H_{13}F_4N_4O$ (M+H)$^+$: 353.1, found: 353.1.

(6-Fluoro-8-methyl-1,3,4,5-tetrahydropyrido[4,3-b]indol-2-yl)-[5-(trifluoromethyl)-1H-pyrazol-3-yl]methanone: Following GP3c, the title compound was obtained from [Int-2.6] (0.147 g, 0.61 mmol) and 5-(trifluoromethyl)-1H-pyrazole-3-carboxylic acid (0.110 g, 0.61 mmol), after purification by preparative LC/MS, as a white solid (0.015 g, 6%). $^1$H NMR (400 MHz, DMSO-d6): δ 14.39 (s, 1H), 11.31 (s, 1H), 7.24 (d, J=30.2 Hz, 1H), 7.08 (d, J=12.7 Hz, 1H), 6.74 (d, J=12.3 Hz, 1H), 4.82 (d, J=31.7 Hz, 2H), 3.98 (d, J=34.1 Hz, 2H), 2.94 (d, J=34.6 Hz, 2H), 2.37 (d, J=8.5 Hz, 3H). UPLC-MS: $t_R$=2.24 min (Method A); MS (ESI) m/z calcd for $C_{17}H_{15}F_4N_4O$ (M+H)$^+$: 367.1, found: 367.2.

(8-Methylsulfonyl-1,3,4,5-tetrahydropyrido[4,3-b]indol-2-yl]-[5-(trifluoromethyl)-1H-pyrazol-3-yl]methanone: Following GP3c, the title compound was obtained from [Int-2.28] (0.068 g, 0.24 mmol) and 5-(trifluoromethyl)-1H-pyrazole-3-carboxylic acid (0.043 g, 0.24 mmol), after purification by silica gel flash-column chromatography with Cyclohexane/EtOAc (50:50) as the eluent, as a white solid in (0.031 g, 31%): $^1$H NMR (400 MHz, DMSO-d$_6$): δ 14.40 (s, 1H), 11.63 (s, 1H), 8.14 (d, J=1.7 Hz, 1H), 7.62-7.56 (m, 1H), 7.56-7.49 (m, 1H), 7.29 (d, J=61.9 Hz, 1H), 4.94 (d, J=38.4 Hz, 2H), 4.02 (tq, J=12.6, 6.6, 5.9 Hz, 2H), 3.21-3.10 (m, 3H), 3.00 (d, J=38.3 Hz, 2H). UPLC-MS: $t_R$=1.71 min (Method A); MS (ESI) m/z calcd for $C_{17}H_{16}F_3N_4O_3S$ (M+H)$^+$: 413.1, found: 413.2.

(4-Fluoro-2-methyl-5,6,7,8,9,10-hexahydro-7,10-epiminocyclohepta[b]indol-11-yl) (5-(trifluoromethyl)-1H-pyrazol-3-yl)methanone: Following GP3c, the title compound was obtained from [Int-2.12] (0.134 g, 0.50 mmol) and 5-(trifluoromethyl)-1H-pyrazole-3-carboxylic acid (0.090 g, 0.50 mmol), after purification by silica gel flash-column chromatography with Cyclohexane/EtOAc (0 to 80%) as the eluent, as a white solid (0.063 g, 32%). $^1$H NMR (400 MHz, DMSO-d6): δ 14.38 (s, 1H), 11.28 (d, J=6.1 Hz, 1H), 7.24 (d, J=47.6 Hz, 1H), 7.08 (d, J=44.0 Hz, 1H), 6.70 (d, J=12.6 Hz, 1H), 5.80-5.58 (m, 1H), 4.98 (d, J=26.8 Hz, 1H), 3.42 (d, J=4.7 Hz, 1H), 2.72 (t, J=15.8 Hz, 1H), 2.44-2.22 (m, 4H), 2.16-2.00 (m, 1H), 1.94 (dt, J=21.3, 10.7 Hz, 1H), 1.76 (d, J=18.0 Hz, 1H). UPLC-MS: $t_R$=2.32 min (Method A); MS (ESI) m/z calcd for $C_{19}H_{17}F_4N_4O$ (M+H)$^+$: 393.1, found: 393.2.

(9-Fluoro-6-methyl-1,3,4,5-tetrahydropyrido[4,3-b]indol-2-yl)-[5-(trifluoromethyl)-1H-pyrazol-3-yl]methanone: Following GP3c, the title compound was obtained from [Int-2.8] (0.090 g, 0.37 mmol) and 5-(trifluoromethyl)-1H-pyrazole-3-carboxylic acid (0.067 g, 0.37 mmol), after purification by silica gel flash-column chromatography with Cyclohexane/EtOAc (0 to 80%) as the eluent, as a white solid (0.041 g, 13%). $^1$H NMR (400 MHz, DMSO-d$_6$): δ 14.41 (s, 1H), 11.21 (s, 1H), 7.21 (s, 1H), 6.79 (s, 1H), 6.70-6.55 (m, 1H), 4.90 (s, 2H), 3.99 (d, J=33.1 Hz, 2H), 2.96 (d, J=31.0 Hz, 2H), 2.40 (s, 3H). UPLC-MS: $t_R$=2.21 min (Method A); MS (ESI) m/z calcd for $C_{17}H_{15}F_4N_4O$ (M+H)$^+$: 367.1, found: 367.2.

(4-Fluoro-1-methyl-5,6,7,8,9,10-hexahydro-7,10-epiminocyclohepta[b]indol-11-yl) (5-(trifluoromethyl)-1H-pyrazol-3-yl)methanone: Following GP3a, the title compound was obtained from [Int-2.13] (0.200 g, 0.75 mmol) and 5-(trifluoromethyl)-1H-pyrazole-3-carboxylic acid (0.135 g, 0.75 mmol), after purification by silica gel flash-column chromatography with Cyclohexane/EtOAc (0 to 80%) as the eluent, as a white solid (0.056 g, 5%). $^1$H NMR (400 MHz, DMSO-d$_6$): δ 14.40 (s, 1H), 11.41 (d, J=12.5 Hz, 1H), 7.18 (d, J=110.2 Hz, 1H), 6.80-6.57 (m, 2H), 5.98-5.61 (m, 1H), 4.97 (d, J=26.9 Hz, 1H), 3.51-3.37 (m, 1H), 2.73 (t, J=15.2 Hz, 1H), 2.57 (s, 1H), 2.41-2.26 (m, 3H), 2.16-1.95 (m, 2H), 1.76 (d, J=8.1 Hz, 1H). UPLC-MS: $t_R$=2.29 min (Method A); MS (ESI) m/z calcd for $C_{19}H_{17}F_4N_4O$ (M+H)$^+$: 393.1, found: 393.2.

(6,9-Dimethyl-1,3,4,5-tetrahydropyrido[4,3-b]indol-2-yl)-[5-(trifluoromethyl)-1H-pyrazol-3-yl]methanone: Following GP3a, the title compound was obtained from [Int-2.7] (0.069 g, 0.29 mmol) and 5-(trifluoromethyl)-1H-pyrazole-3-carboxylic acid (0.052 g, 0.29 mmol), after purification by silica gel flash-column chromatography with Cyclohexane/EtOAc (0 to 90%) as the eluent, as a white solid (0.032 g, 31%). $^1$H NMR (400 MHz, DMSO-d6): δ 14.46 (s, 1H), 10.82 (s, 1H), 7.18 (s, 1H), 6.71 (d, J=7.2 Hz, 1H), 6.62 (d, J=8.6 Hz, 1H), 5.09 (d, J=35.8 Hz, 2H), 4.25-3.70 (m, 2H), 2.94 (d, J=26.5 Hz, 2H), 2.55 (s, 2H), 2.37 (s, 4H). UPLC-MS: $t_R$=2.25 min (Method A); MS (ESI) m/z calcd for $C_{18}H_{18}F_3N_4O$ (M+H)$^+$: 363.1, found: 363.2.

2-[5-(Trifluoromethyl)-1H-pyrazole-3-carbonyl]-1,3,4,5-tetrahydropyrido[4,3-b]indole-8-carbonitrile: Following GP3a, the title compound was obtained from [Int-2.29] (0.039 g, 0.20 mmol) and 5-(trifluoromethyl)-1H-pyrazole-3-carboxylic acid (0.036 g, 0.20 mmol), after purification by preparative LC-MS, as a white solid (0.012 g, 20%). $^1$H NMR (400 MHz, DMSO-d$_6$) δ 14.38 (s, 1H), 11.62 (s, 1H), 8.09 (s, 1H), 7.56-7.35 (m, 2H), 7.25 (app-d, J=36.1 Hz, 1H), 4.89 (app-d, J=35.9 Hz, 2H), 3.98 (app-d, J=36.7 Hz, 2H), 2.97 (app-d, J=37.1 Hz, 2H); UPLC-MS: $t_R$=1.92 min (generic method); MS (ESI) m/z calcd for $C_{17}H_{13}F_3N_5O$ (M+H)$^+$; 360.1, found: 360.2.

(9-Methyl-1,3,4,5-tetrahydropyrido[4,3-b]indol-2-yl)-[5-(trifluoromethyl)-1H-pyrazol-3-yl]methanone: Following GP3c, a mixture of regioisomer [058] and [059] was obtained from [Int-2.24] (0.2 g, 1.07 mmol) and 5-(trifluoromethyl)-1H-pyrazole-3-carboxylic acid (0.212 g, 1.18 mmol). The title compound was obtained, as pure isomer, after purification by preparative LC/MS, as a white solid (0.006 g, 7%). $^1$H NMR (400 MHz, DMSO-d$_6$) δ 14.36 (s, 1H), 10.92 (s, 1H), 7.24-7.03 (m, 2H), 6.90 (s, 1H), 6.70 (s, 1H), 5.24-4.96 (m, 2H), 4.11-3.81 (m, 2H), 3.04-2.80 (m, 2H), 2.58 and 2.46 (s, 3H). NOESY-2D: strong dipolar coupling between multiplet at 5.24-4.96 ppm and singlet at 5.58 ppm. UPLC-MS: $t_R$=2.13 min (Method A); MS (ESI) m/z calcd for $C_{17}H_{16}F_3N_4O$ (M+H)$^+$: 349.1, found: 349.1.

(7-Methyl-1,3,4,5-tetrahydropyrido[4,3-b]indol-2-yl)-[5-(trifluoromethyl)-1H-pyrazol-3-yl]methanone: Following GP3c, a mixture of regioisomer [058] and [059] was obtained from [Int-2.24] (0.200 g, 1.07 mmol) and 5-(trifluoromethyl)-1H-pyrazole-3-carboxylic acid (0.212 g, 1.18 mmol). The title compound was obtained, after purification by preparative LC/MS, as a pure isomer, as a white solid (0.006 g, 7%). $^1$H NMR (400 MHz, DMSO-d6) δ 14.31 (s, 1H), 10.80 (s, 1H), 7.39-7.27 (m, 1H), 7.20 (s, 1H), 7.09 (s, 1H), 6.79 (d, J=12.3 Hz, 1H), 4.97-4.69 (m, 2H), 4.11-3.81 (m, 2H), 3.01-2.81 (m, 2H), 2.37 (s, 3H). UPLC-MS: $t_R$=2.17 min (Method A); MS (ESI) m/z calcd for $C_{17}H_{16}F_3N_4O$ (M+H)$^+$: 349.1, found: 349.1.

(6,8-Difluoro-1,3,4,5-tetrahydropyrido[4,3-b]indol-2-yl)-[5-(trifluoromethyl)-1H-pyrazol-3-yl]methanone: Following GP3a, the title compound was obtained from [Int-2.9] (0.100 g, 0.41 mmol) and 5-(trifluoromethyl)-1H-pyrazole-3-carboxylic acid (0.074 g, 0.41 mmol), after purification by preparative LC/MS, as a white solid (0.049 g, 32%). $^1$H NMR (400 MHz, DMSO-d$_6$): δ 11.59 (s, 1H), 7.27 (s, 1H), 7.22 (dd, J=9.4, 2.3 Hz, 1H), 6.92 (t, J=10.7 Hz, 1H), 4.83 (d, J=36.4 Hz, 2H), 4.07-3.85 (m, 2H), 3.08-2.84 (m, 2H). UPLC-MS: $t_R$=2.23 min (Method A); MS (ESI) m/z calcd for $C_{16}H_{12}F_5N_4O$ (M+H)$^+$: 371.1, found: 371.2.

(6-Bromo-9-methyl-1,3,4,5-tetrahydropyrido[4,3-b]indol-2-yl)-[5-(trifluoromethyl)-1H-pyrazol-3-yl]methanone: Following GP3a, the title compound was obtained from [Int-2.1] (0.250 g, 0.83 mmol) and 5-(trifluoromethyl)-1H-pyrazole-3-carboxylic acid (0.149 g, 0.83 mmol), after purification by preparative LC/MS, as a white solid (0.110 g, 31%). $^1$H NMR (400 MHz, DMSO-d6): δ 11.14 (s, 1H), 7.21 (s, 1H), 7.12 (d, J=7.7 Hz, 1H), 6.77-6.60 (m, 1H), 5.09 (d, J=38.0 Hz, 2H), 3.96 (d, J=34.0 Hz, 2H), 2.96 (d, J=27.8 Hz, 2H), 2.61-2.36 (m, 3H). UPLC-MS: $t_R$=2.44 min (Method A); MS (ESI) m/z calcd for $C_{17}H_{15}BrF_3N_4O$ (M+H)$^+$: 428.2, found: 428.9.

(6-Fluoro-9-methyl-1,3,4,5-tetrahydropyrido[4,3-b]indol-2-yl)-(1H-indol-2-yl)methanone: Following GP3a, the title compound was obtained from [Int-2.2] (0.094 g, 0.46 mmol) and 1H-indole-2-carboxylic acid (0.074 g, 0.46 mmol), after purification by silica gel flash-column chromatography with Cyclohexane/EtOAc (0 to 50%) as the eluent, as a white solid (0.046 g, 29%). $^1$H NMR (400 MHz, DMSO-d6): δ 11.62 (bs, 1H), 11.39 (bs, 1H), 7.66 (dt, J=8.0, 0.8 Hz, 1H), 7.51-7.41 (m, 1H), 7.21 (ddd, J=8.2, 7.0, 1.2 Hz, 1H), 7.07 (ddd, J=8.0, 7.0, 1.0 Hz, 1H), 6.99-6.90 (m, 1H), 6.73 (dd, J=11.2, 7.9 Hz, 1H), 6.65 (t, J=6.3 Hz, 1H), 5.32-4.96 (m, 2H), 4.17-4.06 (m, 2H), 3.10-2.87 (m, 2H), 2.52 (s, 3H). UPLC-MS: $t_R$=2.46 min (Method A); MS (ESI) m/z calcd for $C_{21}H_{19}FN_3O$ (M+H)$^+$: 348.1, found: 348.2.

(6-Fluoro-4,4,9-trimethyl-3,5-dihydro-1H-pyrido[4,3-b]indol-2-yl)-(5-(trifluoromethyl)-1H-pyrazol-3-yl)-methanone: Following GP3a, the title compound was obtained from [Int-2.14] (0.3 g, 1.28 mmol) and 5-(trifluoromethyl)-1H-pyrazole-3-carboxylic acid (0.253 g, 1.40 mmol), after purification by silica gel flash-column chromatography with Cyclohexane/EtOAc (0 to 50%) as the eluent, as a white solid (0.045 g, 9%). $^1$H NMR (400 MHz, DMSO-d6): δ 14.42 (s, 1H), 11.34 (s, 1H), 7.15 (d, J=28.0 Hz, 1H), 6.73 (t, J=9.6 Hz, 1H), 6.63 (br s, 1H), 5.11 (br s, 2H), 3.77-3.72 (m, 2H), 2.50-2.048 (m, 3H), 1.37 (s, 3H), 1.28 (s, 3H). UPLC-MS: $t_R$=2.32 min (Method A); MS (ESI) m/z calcd for $C_{19}H_{19}F_4N_4O$ (M+H)$^+$: 395.1, found: 395.4.

(7R,10S)- or (7S,10R)-4-Fluoro-1-methyl-5,6,7,8,9,10-hexahydro-7,10-epiminocyclohepta[b]indol-11-yl)-(5-(trifluoromethyl)-1H-pyrazol-3-yl)-methanone: The title compound was obtained from compound [055] by means of semi-preparative chiral separation (Column: ChiralPak AD, 250×4.6 mm, 10 μm; mobile phase: n-Heptane-EtOH (75:25); Flow Rate: 1.0 mL/min; UV: 268 nm) as a white powder (0.023 g, 28%). $^1$H NMR (400 MHz, DMSO-d6): δ 14.41 (s, 1H), 11.41 (d, J=12.5 Hz, 1H), 7.18 (d, J=110.2 Hz, 1H), 6.79-6.57 (m, 2H), 5.98-5.61 (m, 1H), 4.97 (d, J=26.9 Hz, 1H), 3.51-3.37 (m, 1H), 2.73 (t, J=14.8 Hz, 1H), 2.57 (s, 1H), 2.41-2.26 (m, 3H), 2.16-1.95 (m, 2H), 1.76 (d, J=8.1 Hz, 1H). UPLC-MS: $t_R$=2.01 min (Method A); MS (ESI) m/z calcd for $C_{19}H_{17}F_4N_4O$ (M+H)$^+$: 393.1, found: 393.4.

(7S,10R)- or (7R,10S)-4-Fluoro-1-methyl-5,6,7,8,9,10-hexahydro-7,10-epiminocyclohepta[b]indol-11-yl)-(5-(trifluoromethyl)-1H-pyrazol-3-yl)-methanone: The title compound was obtained from compound [055] by means of semi-preparative chiral separation (Column: ChiralPak AD, 250×4.6 mm, 10 μm; mobile phase: n-Heptane-EtOH (75:25); Flow Rate: 1.0 mL/min; UV: 268 nm) as a white powder (0.024 g, 28%). $^1$H NMR (400 MHz, DMSO-d6): δ 14.40 (s, 1H), 11.41 (d, J=12.5 Hz, 1H), 7.18 (d, J=110.2 Hz, 1H), 6.80-6.57 (m, 2H), 5.98-5.61 (m, 1H), 4.97 (d, J=26.9 Hz, 1H), 3.51-3.37 (m, 1H), 2.73 (t, J=15.2 Hz, 1H), 2.57 (s, 1H), 2.41-2.26 (m, 3H), 2.16-1.95 (m, 2H), 1.76 (d, J=8.1 Hz, 1H). UPLC-MS: $t_R$=2.02 min (Method A); MS (ESI) m/z calcd for $C_{19}H_{17}F_4N_4O$ (M+H)$^+$: 393.1, found: 393.4.

(6,9-Difluoro-1,3,4,5-tetrahydropyrido[4,3-b]indol-2-yl)-(5-(trifluoromethyl)-1H-pyrazol-3-yl)methanone: Following GP3a, the title compound was obtained from [Int-2.17] (0.100 g, 0.41 mmol) and 5-(trifluoromethyl)-1H-pyrazole-3-carboxylic acid (0.081 g, 0.45 mmol), after purification by silica gel flash-column chromatography with Cyclohexane/EtOAc (0 to 30%) as the eluent, as a white solid (0.020 g, 13%). $^1$H NMR (400 MHz, DMSO-d6): δ 14.39 (s, 1H), 11.78 (s, 1H), 7.20 (s, 1H), 6.85 (t, J=8.6 Hz, 1H), 6.75-6.68 (m, 1H), 5.01-4.84 (m, 2H), 4.00-3.95 (m, 2H), 3.00-2.95 (m, 2H). UPLC-MS: $t_R$=2.32 min (Method A); MS (ESI) m/z calcd for $C_{16}H_{12}F_5N_4O$ (M+H)$^+$: 371.1, found: 371.3.

(6-Fluoro-8-(trifluoromethyl)-1,3,4,5-tetrahydropyrido[4,3-b] indol-2-yl)-(5-(trifluoromethyl)-1H-pyrazol-3-yl)methanone: Following GP3a, the title compound was obtained from [Int-2.21] (0.150 g, 0.51 mmol) and 5-(trifluoromethyl)-1H-pyrazole-3-carboxylic acid (0.101 g, 0.56 mmol), after purification by silica gel flash-column chromatography with Cyclohexane/EtOAc (0 to 50%) as the eluent, as a white solid (0.012 g, 6%). $^1$H NMR (400 MHz, DMSO-d6): δ 14.38 (s, 1H), 12.01 (s, 1H), 7.85 (s, 1H), 7.39-7.10 (m, 2H), 5.08-4.81 (m, 2H), 4.10-3.89 (m, 2H), 3.12-2.89 (m, 2H). UPLC-MS: $t_R$=2.06 min (Method A); MS (ESI) m/z calcd for $C_{17}H_{12}F_7N_4O$ (M+H)$^+$: 421.1, found: 421.5.

(6-Fluoro-8-methoxy-1,3,4,5-tetrahydropyrido[4,3-b]indol-2-yl)-(5-(trifluoromethyl)-1H-pyrazol-3-yl)-methanone: Following GP3a, the title compound was obtained from [Int-2.18] (0.150 g, 0.58 mmol) and 5-(trifluoromethyl)-1H-pyrazole-3-carboxylic acid (0.115 g, 0.64 mmol), after purification by preparative LC-MS, as a white solid (0.056 g, 25%). $^1$H NMR (400 MHz, DMSO-d6): δ 14.39 (br s, 1H), 11.25 (s, 1H), 7.28-7.17 (m, 1H), 6.92-6.80 (m, 1H), 6.59 (dd, J=12.8, 2.1 Hz, 1H), 4.87-4.76 (m, 2H), 4.08-3.88 (m, 2H), 3.77 (d, J=7.8 Hz, 3H), 3.03-2.83 (m, 2H). UPLC-MS: $t_R$=1.86 min (Method A); MS (ESI) m/z calcd for $C_{17}H_{15}F_4N_4O_2$ (M+H)$^+$: 383.1, found: 383.2.

(6-Fluoro-9-(trifluoromethyl)-1,3,4,5-tetrahydropyrido[4,3-b] indol-2-yl)-(5-(trifluoromethyl)-1H-pyrazol-3-yl)-methanone: Following GP3a, the title compound was obtained from [Int-2.20] (0.5 g, 1.70 mmol) and 5-(trifluoromethyl)-1H-pyrazole-3-carboxylic acid (0.335 g, 1.86 mmol), after purification by silica gel flash-column chromatography with Cyclohexane/EtOAc (0 to 50%) as the eluent, as a white solid (0.023 g, 7%). $^1$H NMR (400 MHz, DMSO-d6): δ 14.39 (br s, 1H), 12.20 (s, 1H), 7.41 (br s, 1H), 7.23-7.02 (m, 1H), 7.08 (t, J=9.3 Hz, 1H), 4.85 (s, 2H), 4.13-3.84 (m, 2H), 3.10-3.01 (m, 2H). UPLC-MS: $t_R$=2.03 min (Method A); MS (ESI) m/z calcd for $C_{17}H_{12}F_7N_4O$ (M+H)$^+$: 421.1, found: 421.3.

(6-Chloro-8-methoxy-1,3,4,5-tetrahydropyrido[4,3-b]indol-2-yl)-(5-(trifluoromethyl)-1H-pyrazol-3-yl) methanone: Following GP3a, the title compound was obtained from [Int-2.18] (0.150 g, 0.58 mmol) and 5-(trifluoromethyl)-1H-pyrazole-3-carboxylic acid (0.115 g, 0.64 mmol), after purification by preparative LC-MS, as a by-product of compound [086], as a white solid (0.020 g, 18%). $^1$H NMR (400 MHz, DMSO-d6): δ 14.37 (br s, 1H), 11.14 (s, 1H), 7.28-7.17 (m, 1H), 7.09-6.97 (m, 1H), 6.80 (d, J=2.2 Hz, 1H), 4.89-4.75 (m, 2H), 4.07-3.89 (m, 2H), 3.78 (s, 3H), 3.05-2.85 (m, 2H). UPLC-MS: $t_R$=2.13 min (Method A); MS (ESI) m/z calcd for $C_{17}H_{15}ClF_3N_4O$ (M+H)$^+$: 399.1, found: 399.9.

(6-Fluoro-9-methyl-1,3,4,5-tetrahydropyrido[4,3-b]indol-2-yl)-(2-(trifluoromethyl) thiazol-4-yl)methanone: Following GP3a, the title compound was obtained from [Int-2.2] (0.070 g, 0.29 mmol) and 2-(trifluoromethyl)thiazole-4-carboxylic acid (0.063 g, 0.32 mmol), after purification by silica gel flash-column chromatography with Cyclohexane/EtOAc (0 to 30%) as the eluent, as a white solid (0.033 g, 30%). $^1$H NMR (400 MHz, DMSO-d6): δ 11.36 (s, 1H), 8.63 (d, J=10.6 Hz, 1H), 6.78-6.58 (m, 2H), 5.20-5.07 (m, 2H), 4.03-3.83 (m, 2H), 2.91 (t, J=5.2 Hz, 2H), 2.56-2.35 (m, 3H). UPLC-MS: $t_R$=2.08 min (Method A); MS (ESI) m/z calcd for $C_{17}H_{14}F_4N_3OS$ (M+H)$^+$: 384.1, found: 384.5.

(4-Bromo-3-pyridyl)-(6-fluoro-9-methyl-1,3,4,5-tetrahydropyrido[4,3-b]indol-2-yl)methanone: Following GP3a, the title compound was obtained from [Int-2.2] (0.070 g, 0.29 mmol) and 4-bromopyridine-3-carboxylic acid (0.064 g, 0.32 mmol), after purification by silica gel flash-column chromatography with Cyclohexane/EtOAc (0 to 60%) as the eluent, as a white solid (0.037 g, 33%). $^1$H NMR (400 MHz, DMSO-d6): δ 11.39-11.35 (m, 1H), 8.67-8.59 (m, 1H), 8.52 (dd, J=8.1, 5.4 Hz, 1H), 7.88-7.66 (m, 1H), 6.77-6.55 (m, 1H), 6.71-6.66 (m, 1H), 5.26-4.95 (m, 2H), 3.54 (tt, J=5.9, 2.5 Hz, 2H), 2.98-2.77 (m, 2H), 2.57 (s, 3H). UPLC-MS: $t_R$=1.95 min (Method A); MS (ESI) m/z calcd for $C_{18}H_{16}BrFN_3O$ (M+H)$^+$: 388.0, found: 389.2.

(3-Bromo-4-pyridyl)-(6-fluoro-9-methyl-1,3,4,5-tetrahydropyrido[4,3-b]indol-2-yl)methanone: Following GP3a, the title compound was obtained from [Int-2.2] (0.070 g, 0.29 mmol) and 3-bromopyridine-4-carboxylic acid (0.064 g, 0.32 mmol), after purification by silica gel flash-column chromatography with Cyclohexane/EtOAc (0 to 50%) as the eluent, as a white solid (0.037 g, 33%). $^1$H NMR (400 MHz, DMSO-d6): δ 11.40-11.35 (m, 1H), 8.89-8.82 (m, 1H), 8.66 (dd, J=9.1, 4.8 Hz, 1H), 7.56-7.41 (m, 1H), 6.79-6.55 (m, 1H), 6.71-6.66 (m, 1H), 5.26-4.98 (m, 2H), 3.50 (q, J=5.8 Hz, 2H), 2.81 (t, J=5.9 Hz, 2H), 2.57 (s, 3H). UPLC-MS: $t_R$=1.99 min (Method A); MS (ESI) m/z calcd for $C_{18}H_{16}BrFN_3O$ (M+H)$^+$: 388.0, found: 389.5.

(5-Bromo-2-methoxy-3-pyridyl)-(6-fluoro-9-methyl-1,3,4,5-tetrahydropyrido[4,3-b]indol-2-yl)methanone: Following GP3a, the title compound was obtained from [Int-2.2] (0.070 g, 0.29 mmol) and 5-bromo-2-methoxy-pyridine-3-carboxylic acid (0.074 g, 0.32 mmol), after purification by silica gel flash-column chromatography with Cyclohexane/EtOAc (0 to 30%) as the eluent, as a white solid (0.017 g, 14%). $^1$H NMR (400 MHz, DMSO-d6): δ 11.37-11.31 (m, 1H), 8.40 (t, J=2.8 Hz, 1H), 8.02-7.93 (m, 1H), 6.74 (dd, J=11.2, 7.9 Hz, 1H), 6.71-6.65 (i, 1H), 5.10-4.58 (m, 2H), 3.91 (s, 3H), 3.52 (d, J=6.8 Hz, 2H), 2.94-2.71 (m, 2H), 2.55 (s, 3H). UPLC-MS: $t_R$=2.29 min (Method A); MS (ESI) m/z calcd for $C_{19}H_{18}BrFN_3O_2$ (M+H)$^+$: 418.0, found: 419.7.

(2-Amino-4-(trifluoromethyl)thiazol-5-yl)-(6-fluoro-9-methyl-1,3,4,5-tetrahydropyrido[4,3-b]indol-2-yl)-methanone: Following GP3a, the title compound was obtained from [Int-2.2] (0.070 g, 0.29 mmol) and 2-amino-4-(trifluoromethyl)thiazole-5-carboxylic acid (0.068 g, 0.32 mmol), after purification by silica gel flash-column chromatography with Cyclohexane/EtOAc (0 to 40%) as the eluent, as a white solid (0.021 g, 18%). $^1$H NMR (400 MHz, DMSO-d6): δ 11.35 (s, 1H), 7.72 (s, 2H), 6.73 (dd, J=11.2, 7.9 Hz, 1H), 6.65 (dd, J=8.0, 4.7 Hz, 1H), 5.15-4.65 (m, 2H), 3.95-3.65 (m, 2H), 2.83 (t, J=5.8 Hz, 2H), 2.52 (s, 3H). UPLC-MS: $t_R$=1.98 min (Method A); MS (ESI) m/z calcd for $C_{17}H_{15}F_4N_4OS$ (M+H)$^+$: 399.1, found: 399.0.

(3-(4-Bromophenyl)-5-methyl-isoxazol-4-yl)-(6-fluoro-9-methyl-1,3,4,5-tetrahydropyrido[4,3-b]indol-2-yl)-methanone: Following GP3a, the title compound was obtained from [Int-2.2] (0.070 g, 0.29 mmol) and 3-(4-bromophenyl)-5-methyl-isoxazole-4-carboxylic acid (0.090 g, 0.32 mmol), after purification by silica gel flash-column chromatography with Cyclohexane/EtOAc (0 to 30%) as the eluent, as a white solid (0.022 g, 16%). $^1$H NMR (400 MHz, DMSO-d6): δ 11.28-11.19 (r, 1H), 7.71 (d, J=8.2 Hz, 1H), 7.58 (d, J=8.2 Hz, 1H), 7.34 (q, J=8.4 Hz, 2H), 6.78-6.52 (m, 1H), 6.70-6.61 (m, 1H), 5.07 (br s, 2H), 3.56 (br s, 2H), 2.85 (br s, 2H), 2.17 (s, 3H), 1.40 (s, 3H). UPLC-MS: $t_R$=2.43 min (Method A); MS (ESI) m/z calcd for $C_{23}H_{20}BrFN_3O_2$ (M+H)$^+$: 468.1, found: 469.5.

3-(6-Fluoro-9-methyl-1,3,4,5-tetrahydropyrido[4,3-b]indole-2-carbonyl)-1H-pyrazole-5-carboxylic acid: Following GP3a, the title compound was obtained from [Int-2.2] (0.070 g, 0.29 mmol) and 1H-pyrazole-3,5-dicarboxylic acid (0.091 g, 0.58 mmol), after purification by preparative LC/MS, as a white solid (0.012 g, 12%). $^1$H NMR (400 MHz, DMSO-d6): δ 11.37-11.30 (m, 1H), 6.76-6.57 (m, 3H), 5.43-4.17 (m, 2H), 5.08-3.95 (m, 2H), 2.95-2.78 (m, 2H), 2.55 (s, 3H). UPLC-MS: $t_R$=1.40 min (Method A); MS (ESI) m/z calcd for $C_{17}H_{16}FN_4O_3$ (M+H)$^+$: 343.1, found: 343.2.

rac-(6-Fluoro-3,9-dimethyl-1,3,4, 5-tetrahydropyrido [4,3-b] indol-2-yl)-(5-(trifluoromethyl)-1H-pyrazol-3-yl)methanone: Following GP3a, the title compound was obtained from [Int-2.32] (0.070 g, 0.27 mmol) and 5-(trifluoromethyl)-1H-pyrazole-3-carboxylic acid (0.048 g, 0.27 mmol), after purification by silica gel flash-column chromatography with Cyclohexane/EtOAc (0 to 50%) as the eluent, as a white solid (0.049 g, 47%). $^1$H-NMR (400 MHz, DMSO-d6) δ 14.37 (bs), 11.36 (bs), 7.18 (bs), 6.73 (dd, J=11.2, 8.0 Hz, 1H), 6.66 (m, 1H), 4.48-5.57 (m, 3H), 3.13 (m, 1H), 2.69 (s, 3H), 2.65 (m, 1H), 2.34 (m, 1H), 1.26 (d, J=6.8 Hz, 3H). UPLC-MS: $t_R$=2.58 min (Method A); MS (ESI) m/z calcd for $C_{18}H_{17}F_4N_4O$ (M+H)$^+$: 381.1, found: 381.3.

rac-(6-Fluoro-1, 9-dimethyl-1,3,4, 5-tetrahydropyrido [4,3-b] indol-2-yl)-[5-(trifluoromethyl)-1H-pyrazol-3-yl]methanone: Following GP3a, the title compound was obtained from [Int-2.33] (0.090 g, 0.35 mmol) and 5-(trifluoromethyl)-1H-pyrazole-3-carboxylic acid (0.062 g, 035 mmol), after purification by silica gel flash-column chromatography with Cyclohexane/EtOAc (0 to 50%) as the eluent, as a white solid (0.060 g, 45%). $^1$H-NMR (400 MHz, DMSO-d6) δ 14.38 (bs), 11.41 (bs), 7.18 (bs), 6.75 (dd, J=11.1, 7.9 Hz, 1H), 6.68 (dd, J=8.2, 5 Hz, 1H), 5.99 (q, J=6.6 Hz, 1H), 4.15 (m, 1H), 3.71 (ddd, J=14.1, 11.9, 4.4 Hz), 3.13 (ddd, J=17.1, 11.9, 6.0 Hz, 1H), 2.82 (dd, J=16.5, 4.2 Hz, 1H), 2.58 (s, 3H), 1.56 (d, J=6.5 Hz, 3H). UPLC-MS: $t_R$=2.58 min (Method A); MS (ESI) m/z calcd for $C_{18}H_{17}F_4N$ (M+H)$^+$: 381.1, found: 381.3.

8-Methoxy-N-(5-methyl-1H-pyrazol-3-yl)-1,3,4,5-tetrahydropyrido[4,3-b]indole-2-carboxamide: To a solution of 5-methyl-1H-pyrazol-3-amine (0.026 g, 0.26 mmol) in DMF (2.0 mL), DIPEA (90 µL, 0.52 mmol) and carbonyldiimidazole (0.046 g, 0.26 mmol) were added. After 1 h stirring, 8-methoxy-2,3,4,5-tetrahydro-1H-pyrido[4,3-b]indole (0.054 g, 0.26 mmol) was added, and mixture stirred at room temperature for 12 h and at 60° C. for 4 h. EtOAc (20 mL) was added and organic layer was washed with water, aq. sat. NH$_4$Cl (15 mL) and brine (20 mL). The organic layer was dried over Na$_2$SO$_4$, filtered and concentrated in vacuo. Flash chromatography purification, eluting with cyclohexane/EtOAc (50:50) gave the pure title compound as pale yellow solid (0.012 g, 14%). $^1$H NMR (400 MHz, DMSO-d$_6$) δ 11.76 (s, 1H), 10.67 (s, 1H), 8.90 (s, 1H), 7.17 (d, J=8.7 Hz, 1H), 6.88 (d, J=2.4 Hz, 1H), 6.67 (dd, J=24.4, 8.7 Hz, 1H), 6.07 (s, 1H), 4.60 (s, 2H), 3.79 (t, J=5.7 Hz, 2H), 3.75 (s, 3H), 2.77 (t, J=5.7 Hz, 2H), 2.16 (s, 3H). UPLC-MS: $t_R$=1.59 min (method A); MS (ESI) m/z calcd for $C_{17}H_{20}N_5O_2$ (M+H)$^+$: 326.2, found: 326.2.

(R)-(6-Fluoro-3, 9-dimethyl-1,3,4, 5-tetrahydropyrido [4,3-b] indol-2-yl)-[5-(trifluoromethyl)-1H-pyrazol-3-yl]methanone: Following GP3a, the title compound was obtained from [Int-2.34] (0.070 g, 0.27 mmol) and 5-(trifluoromethyl)-1H-pyrazole-3-carboxylic acid (0.048 g, 0.27 mmol), after purification by silica gel flash-column chromatography with Cyclohexane/EtOAc (0 to 50%) as the eluent, as a white solid (0.049 g, 47%). $^1$H-NMR (400 MHz, DMSO-d6) δ 14.37 (bs), 11.36 (bs), 7.18 (bs), 6.73 (dd, J=11.2, 8.0 Hz, 1H), 6.66 (m, 1H), 4.48-5.57 (m, 3H), 3.13 (m, 1H), 2.69 (s, 3H), 2.65 (m, 1H), 2.34 (m, 1H), 1.26 (d, J=6.8 Hz, 3H). UPLC-MS: $t_R$=2.58 min (Method A); MS (ESI) m/z calcd for $C_{18}H_{17}F_4N_4O$ (M+H)$^+$: 381.1, found: 381.3. Chiral analysis: $t_R$=112.7 min; e.e.=97.3%

(S)-(6-Fluoro-3, 9-dimethyl-1,3,4, 5-tetrahydropyrido [4, 3-b] indol-2-yl)-[5-(trifluoromethyl)-1H-pyrazol-3-yl] methanone: Following GP3a, the title compound was obtained from [Int-2.35] (0.070 g, 0.27 mmol) and 5-(trifluoromethyl)-1H-pyrazole-3-carboxylic acid (0.048 g, 0.27 mmol), after purification by silica gel flash-column chromatography with Cyclohexane/EtOAc (0 to 50%) as the eluent, as a white solid (0.049 g, 47%). $^1$H-NMR (400 MHz, DMSO-d6) δ 14.37 (bs), 11.36 (bs), 7.18 (bs), 6.73 (dd, J=11.2, 8.0 Hz, 1H), 6.66 (m, 1H), 4.48-5.57 (m, 3H), 3.13 (m, 1H), 2.69 (s, 3H), 2.65 (m, 1H), 2.34 (m, 1H), 1.26 (d, J=6.8 Hz, 3H). UPLC-MS: $t_R$=2.58 min (Method A); MS (ESI) m/z calcd for $C_{18}H_{17}FN_4O$ (M+H)$^+$: 381.1, found: 381.3. Chiral analysis: $t_R$=104.39 min; e.e.=78.0%.

(6-Fluoro-3,3, 9-trimethyl-1,3,4, 5-tetrahydropyrido [4, 3-b] indol-2-yl)-(5-(trifluoromethyl)-1H-pyrazol-3-yl) methanone: Following GP3a, the title compound was obtained from [Int-2.36] (0.045 g, 0.19 mmol) and 5-(trifluoromethyl)-1H-pyrazole-3-carboxylic acid (0.080 g, 0.44 mmol), after purification by silica gel flash-column chromatography with Cyclohexane/EtOAc (0 to 50%) as the eluent, as a white solid (0.016 g, 20%). $^1$H-NMR (400 MHz, DMSO-d6) δ 14.29 (bs, 1H), 11.38 (bs, 1H), 7.14 (s, 1H), 6.70 (dd, J=11.3, 7.8 Hz, 1H), 6.59 (ddd, J=7.8, 4.7, 0.6 Hz, 1H), 5.0 (s, 2H), 2.96 (s, 2H), 2.30 (s, 3H), 1.59 (s, 6H).

UPLC-MS: $t_R$=2.45 min (Method A); MS (ESI) m/z calcd for $C_{19}H_{19}F_4N_4O$ (M+H)+: 394.4, found: 394.5.

[(S)-6, 9-Difluoro-3-methyl-1,3,4, 5-tetrahydropyrido [4, 3-b] indol-2-yl]-[5-(trifluoromethyl)-1H-pyrazol-3-yl] methanone: Following GP3a, the title compound was obtained from [Int-2.37] (0.024 g, 0.108 mmol) and 5-(trifluoromethyl)-1H-pyrazole-3-carboxylic acid (0.022 g, 0.12 mmol), after purification by silica gel flash-column chromatography with Cyclohexane/EtOAc (0 to 50%) as the eluent, as a white solid (0.021 g, 46%). $^1$H-NMR (400 MHz, DMSO-d6) δ 14.37 (bs, 1H), 11.76 (s, 1H), 7.16 (bs, 1H), 6.84 (ddd, J=11.8, 8.8, 3.5 Hz, 1H), 6.71 (m, 1H), 4.30-5.43 (m, 3H), 3.12 (m, 1H), 2.68 (m, 1H), 1.26 (d, J=6.7 Hz, 3H). UPLC-MS: $t_R$=2.17 min (Method A); MS (ESI) m/z calcd for $C_{17}H_{14}F_5N_4O$ (M+H)+: 384.1, found: 385.4.

[(R)-6-Fluoro-3, 9-dimethyl-1,3,4, 5-tetrahydropyrido [4, 3-b] indol-2-yl]-(1H-indol-2-yl) methanone: Following GP3a, the title compound was obtained from [Int-2.34] (0.025 g, 0.114 mmol) and indole 2-carboxylic acid (0.02 g, 0.13 mmol), after purification by silica gel flash-column chromatography with Cyclohexane/EtOAc (0 to 50%) as the eluent, as a white solid (0.036 g, 87%). $^1$H-NMR (400 MHz, DMSO-d6) δ 11.59 (s, 1H), 11.35 (s, 1H), 7.64 (dd, J=8.0, 1.0 Hz, 1H), 7.44 (dd, J=8.2, 1.0 Hz, 1H), 7.20 (ddd, J=8.2, 7.0, 1.2 Hz, 1H), 7.06 (ddd, J=8.0, 7.0, 1.0 Hz, 1H) 6.91 (d, J=1.3 Hz, 1H), 6.73 (dd, J=11.2, 8.0 Hz, 1H), 6.65 (dd, J=7.9, 4.7 Hz, 1H), 5.60 (d, J=16.2 Hz, 1H), 5.22 (m, 1H), 4.68 (m, 1H), 3.23 (m, 1H), 2.70 (d, J=16.5 Hz, 1H), 2.53, (s, 3H), 1.28 (d, J=6.8 Hz, 3H). UPLC-MS: $t_R$=2.40 min (Method A); MS (ESI) m/z calcd for $C_{22}H_{21}FN_3O$ (M+H)+: 362.2, found: 362.5.

[(S)-8-Methoxy-6-fluoro-3-methyl-1,3, 4,5-tetrahydropyrido [4, 3-b] indol-2-yl]-[5-(trifluoromethyl)-1H-pyrazol-3-yl]methanone: Following GP3a, the title compound was obtained from [Int-2.40] (0.018 g, 0.076 mmol) and 5-(trifluoromethyl)-1H-pyrazole-3-carboxylic acid (0.015 g, 0.085 mmol), after purification by silica gel flash-column chromatography with Cyclohexane/EtOAc (0 to 50%) as the eluent, as a white solid (0.011 g, 39%). $^1$H-NMR (400 MHz, DMSO-d6) δ 14.40 (bs, 1H), 11.23 (bs, 1H), 7.20 (bs, 1H), 6.87 (bs, 1H), 6.58 (dd, J=12.8, 2.1 Hz, 1H), 4.17-5.33 (m, 3H), 3.77 (s, 3H), 3.11 (m, 1H), 2.61 (m, 1H), 1.24 (d, J=6.7 Hz, 3H). UPLC-MS: $t_R$=2.11 min (Method A); MS (ESI) m/z calcd for $C_{18}H_{17}F_4N_4O$ (M+H)+: 397.1, found: 397.4. Chiral analysis: $t_R$=9.60 min; e.e.=>99.5% rac-(6-Fluoro-1-methyl-8-methoxy-1, 3,4,5-tetrahydropyrido [4, 3-b] indol-2-yl]-(5 (trifluoromethyl)-1H-pyrazol-3-yl)methanone: Following GP3a, the title compound was obtained from [Int-2.41] (0.018 g, 0.076 mmol) and 5-(trifluoromethyl)-1H-pyrazole-3-carboxylic acid (0.015 g, 0.085 mmol), after purification by silica gel flash-column chromatography with Cyclohexane/EtOAc (0 to 50%) as the eluent, as a white solid as a mixture of rotamers (major/minor 0.72:0.28) (0.014 g, 46%). $^1$H-NMR (400 MHz, DMSO-d6) of major rotamer: δ 14.38 (bs, 1H), 11.24 (bs, 1H), 7.17 (bs, 1H), 6.86 (bs, 1H), 6.59 (bd, J=13.1 Hz, 1H), 5.68 (q, J=6.6 Hz, 1H), 4.17 (m, 1H), 3.78 (s, 3H), 3.60 (m, 1H), 3.14 (m, 1H), 2.77 (m, 1H), 1.52 (d, J=6.7 Hz, 3H). UPLC-MS: $t_R$=2.11 min (Method A); MS (ESI) m/z calcd for $C_{18}H_{17}F_4N_4O$ (M+H)+: 397.1, found: 397.4.

[(R)-8-Methoxy-6-fluoro-3-methyl-1,3, 4,5-tetrahydropyrido [4, 3-b] indol-2-yl]-[5-(trifluoromethyl)-1H-pyrazol-3-yl]methanone: Following GP3a, the title compound was obtained from [Int-2.42] (0.018 g, 0.076 mmol) and 5-(trifluoromethyl)-1H-pyrazole-3-carboxylic acid (0.015 g, 0.085 mmol), after purification by silica gel flash-column chromatography with Cyclohexane/EtOAc (0 to 50%) as the eluent, as a white solid (0.011 g, 39%). $^1$H-NMR (400 MHz, DMSO-d6) δ 14.40 (bs, 1H), 11.23 (bs, 1H), 7.20 (bs, 1H), 6.87 (bs, 1H), 6.58 (dd, J=12.8, 2.1 Hz, 1H), 4.17-5.33 (m, 3H), 3.77 (s, 3H), 3.11 (m, 1H), 2.61 (m, 1H), 1.24 (d, J=6.7 Hz, 3H). UPLC-MS: $t_R$=2.11 min (Method A); MS (ESI) m/z calcd for $C_{18}H_{17}F_4N_4O$ (M+H)+: 397.1, found: 397.4. Chiral analysis: $t_R$=14.04 min; e.e.=98.6%.

BIOLOGICAL DATA

Activity in terms of EC50 of the compounds of the invention is illustrated in Table 1.

TABLE 1

| # | Compound structure | Substance Name | Substance Formula | Activity |
|---|---|---|---|---|
| 001 | 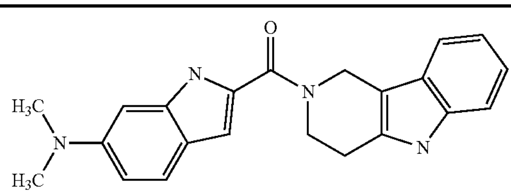 | (6-Dimethylamino-1H-indol-2-yl)-(1,3,4,5-tetrahydro-pyrido[4,3-b]indol-2-yl)-methanone | C22 H22 N4 O | +++ |
| 002 | 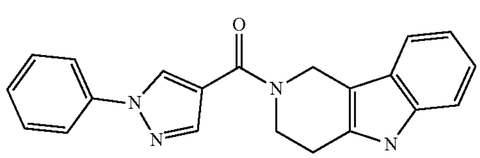 [SMILES: O=C(c1cnn(-c2ccccc2)c1)N1CCc2[nH]c3ccccc3c2C1] | (1-Phenyl-1H-pyrazol-4-yl) (1,3,4,5-tetrahydro-pyrido[4,3-b]indol-2-yl)-methanone | C21 H18 N4 O | + |
| 003 | 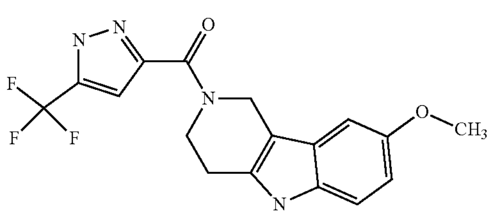 [SMILES: COc1ccc2[nH]c3c(c2c1)CN(C(=O)c1cc(C(F)(F)F)[nH]n1)CC3] | (8-Methoxy-1,3,4,5-tetrahydro-pyrido[4,3-b]indol-2-yl)-(5-trifluoromethyl-1H-pyrazol-3-yl)-methanone | C17 H15 F3 N4 O2 | +++ |

TABLE 1-continued

| # | Compound structure | Substance Name | Substance Formula | Activity |
|---|---|---|---|---|
| 004 | 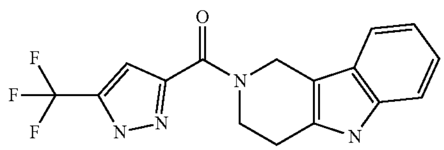 [SMILES: O=C(c1cc(C(F)(F)F)[nH]n1)N1CCc2[nH]c3ccccc3c2C1] | 1,3,4,5-tetrahydropyrido[4,3-b]indol-2-yl-[5-(trifluoromethyl)-1H-pyrazol-3-yl)methanone | C16 H13 F3 N4 O | +++ |
| 005 | 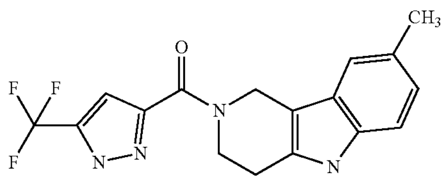 [SMILES: Cc1ccc2[nH]c3c(c2c1)CN(C(=O)c1cc(C(F)(F)F)[nH]n1)CC3] | (8-methyl-1,3,4,5-tetrahydropyrido[4,3-b]indol-2-yl)-[5-(trifluoromethyl)-1H-pyrazol-3-yl]methanone | C17 H15 F3 N4 O | +++ |
| 006 | 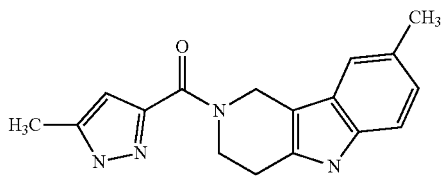 [SMILES: Cc1ccc2[nH]c3c(c2c1)CN(C(=O)c1cc(C)[nH]n1)CC3] | (5-methyl-1H-pyrazol-3-yl)-(8-methyl-1,3,4,5-tetrahydropyrido[4,3-b]indol-2-yl)methanone | C17 H18 N4 O | + |
| 007 | 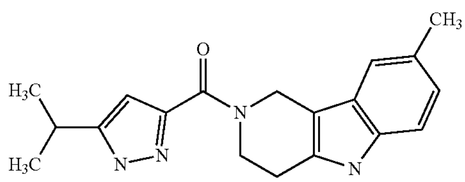 [SMILES: Cc1ccc2[nH]c3c(c2c1)CN(C(=O)c1cc(C(C)C)[nH]n1)CC3] | (5-isopropyl-1H-pyrazol-3-yl)-(8-methyl-1,3,4,5-tetrahydropyrido[4,3-b]indol-2-yl)methanone | C19 H22 N4 O | + |
| 008 | 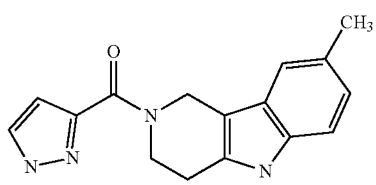 [SMILES: Cc1ccc2[nH]c3c(c2c1)CN(C(=O)c1cc[nH]n1)CC3] | (8-methyl-1,3,4,5-tetrahydropyrido[4,3-b]indol-2-yl)-(1H-pyrazol-3-yl)methanone | C16 H16 N4 O | + |
| 009 | 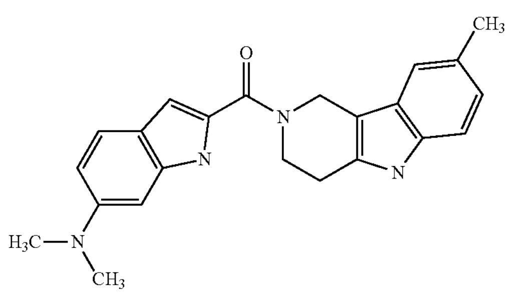 [SMILES: Cc1ccc2[nH]c3c(c2c1)CN(C(=O)c1cc2ccc(N(C)C)cc2[nH]1)CC3] | [6-(dimethylamino)-1H-indol-2-yl]-(8-methyl-1,3,4,5-tetrahydropyrido[4,3-b]indol-2-yl)methanone | C23 H24 N4 O | +++ |
| 010 | 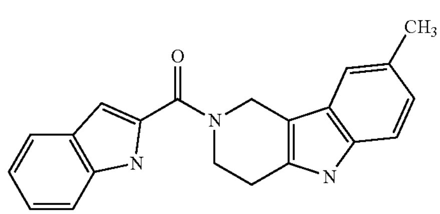 [SMILES: Cc1ccc2[nH]c3c(c2c1)CN(C(=O)c1cc2ccccc2[nH]1)CC3] | 1H-indol-2-yl-(8-methyl-1,3,4,5-tetrahydropyrido[4,3-b]indol-2-yl)methanone | C21 H19 N3 O | +++ |
| 011 | 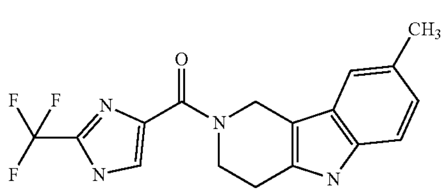 [SMILES: Cc1ccc2[nH]c3c(c2c1)CN(C(=O)c1c[nH]c(C(F)(F)F)n1)CC3] | (8-methyl-1,3,4,5-tetrahydropyrido[4,3-b]indol-2-yl)-[2-(trifluoromethyl)-1H-imidazol-4-yl)methanone | C17 H15 F3 N4 O | + |

TABLE 1-continued

| # | Compound structure | Substance Name | Substance Formula | Activity |
|---|---|---|---|---|
| 012 | 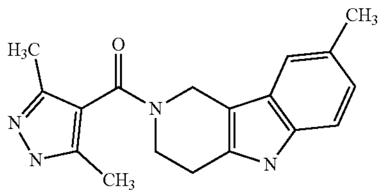 [SMILES: Cc1ccc2[nH]c3c(c2c1)CN(C(=O)c1c(C)n[nH]c1C)CC3] | (3,5-dimethyl-1H-pyrazol-4-yl)-(8-methyl-1,3,4,5-tetrahydropyrido[4,3-b]indol-2-yl)methanone | C18 H20 N4 O | + |
| 013 | 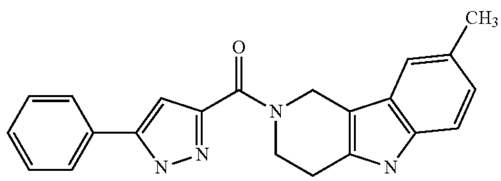 [SMILES: Cc1ccc2[nH]c3c(c2c1)CN(C(=O)c1cc(-c2ccccc2)[nH]n1)CC3] | (8-methyl-1,3,4,5-tetrahydropyrido[4,3-b]indol-2-yl)-(5-phenyl-1H-pyrazol-3-yl)methanone | C22 H20 N4 O | +++ |
| 014 | 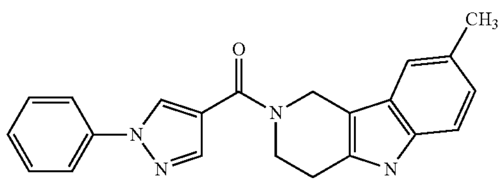 [SMILES: Cc1ccc2[nH]c3c(c2c1)CN(C(=O)c1cnn(-c2ccccc2)c1)CC3] | (8-methyl-1,3,4,5-tetrahydropyrido[4,3-b]indol-2-yl)-(1-phenylpyrazol-4-yl)methanone | C22 H20 N4 O | + |
| 015 | 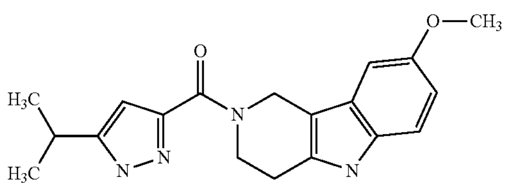 [SMILES: COc1ccc2[nH]c3c(c2c1)CN(C(=O)c1cc(C(C)C)[nH]n1)CC3] | (5-isopropyl-1H-pyrazol-3-yl)-(8-methoxy-1,3,4,5-tetrahydropyrido[4,3-b]indol-2-yl)methanone | C19 H22 N4 O2 | + |
| 016 | 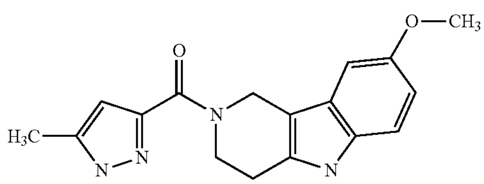 | (8-methyl-1,3,4,5-tetrahydropyrido[4,3-b]indol-2-yl)-(5-methyl-1H-pyrazol-3-yl)methanone | C17 H18 N4 O2 | + |
| 017 | 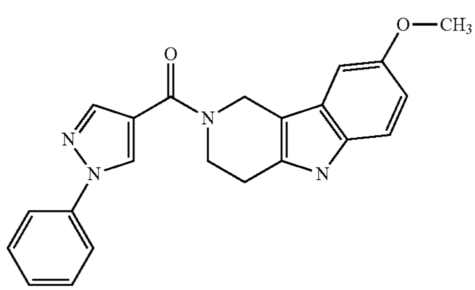 [SMILES: COc1ccc2[nH]c3c(c2c1)CN(C(=O)c1cnn(-c2ccccc2)c1)CC3] | (8-methyl-1,3,4,5-tetrahydropyrido[4,3-b]indol-2-yl)-(1-phenylpyrazol-4-yl)methanone | C22 H20 N4 O2 | + |
| 018 | 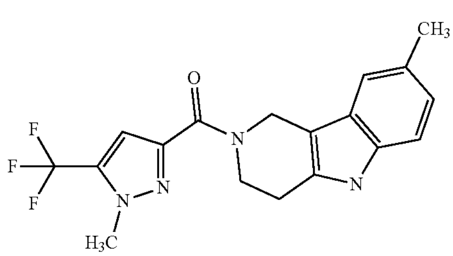 [SMILES: Cc1ccc2[nH]c3c(c2c1)CN(C(=O)c1cc(C(F)(F)F)n(C)n1)CC3] | (8-methyl-1,3,4,5-tetrahydropyrido[4,3-b]indol-2-yl)-[1-methyl-5-(trifluoromethyl)pyrazol-3-yl]methanone | C18 H17 F3 N4 O | + |

TABLE 1-continued

| # | Compound structure | Substance Name | Substance Formula | Activity |
|---|---|---|---|---|
| 019 | 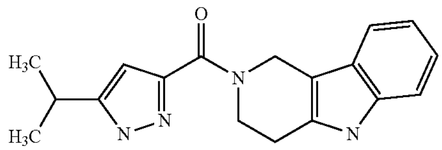 [SMILES: CC(C)c1cc(C(=O)N2CCc3[nH]c4ccccc4c3C2)n[nH]1] | (5-isopropyl-1H-pyrazol-3-yl)-(1,3,4,5-tetrahydropyrido[4,3-b]indol-2-yl)methanone | C18 H20 N4 O | + |
| 021 | 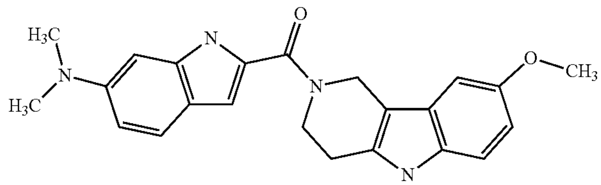 | [6-(dimethylamino)-1H-indol-2-yl]-(8-methoxy-1,3,4,5-tetrahydropyrido[4,3-b]indol-2-yl)methanone | C23 H24 N4 O2 | +++ |
| 022 | 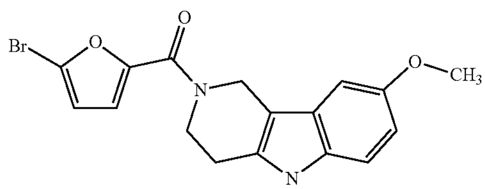 [SMILES: COc1ccc2[nH]c3c(c2c1)CN(C(=O)c1ccc(Br)o1)CC3] | 2-(5-bromo-2-furoyl)-8-methoxy-2,3,4,5-tetrahydro-1H-pyrido[4,3-b]indole | C17 H15 Br N2 O3 | + |
| 023 | 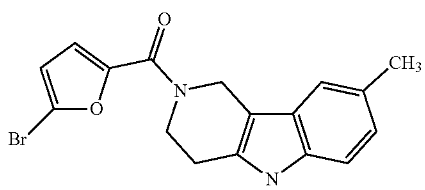 [SMILES: Cc1ccc2[nH]c3c(c2c1)CN(C(=O)c1ccc(Br)o1)CC3] | (5-bromo-2-furyl)-(8-methyl-1,3,4,5-tetrahydropyrido[4,3-b]indol-2-yl)methanone | C17 H15 Br N2 O2 | + |
| 024 | 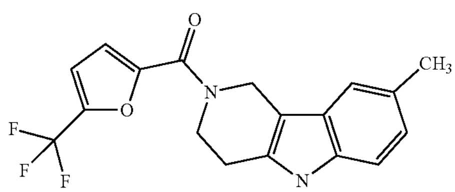 [SMILES: Cc1ccc2[nH]c3c(c2c1)CN(C(=O)c1ccc(C(F)(F)F)o1)CC3] | (8-methyl-1,3,4,5-tetrahydropyrido[4,3-b]indol-2-yl)-[5-(trifluoromethyl)-2-furyl]methanone | C18 H15 F3 N2 O2 | +++ |
| 025 | 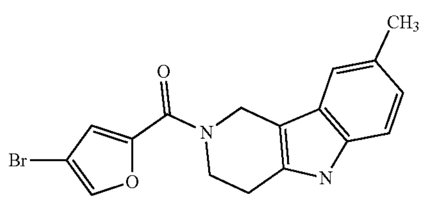 [SMILES: Cc1ccc2[nH]c3c(c2c1)CN(C(=O)c1cc(Br)co1)CC3] | (4-bromo-2-furyl)-(8-methyl-1,3,4,5-tetrahydropyrido[4,3-b]indol-2-yl)methanone | C17 H15 Br N2 O2 | + |
| 026 | 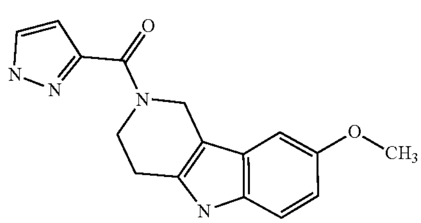 [SMILES: COc1ccc2[nH]c3c(c2c1)CN(C(=O)c1cc[nH]n1)CC3] | (8-methoxy-1,3,4,5-tetrahydropyrido[4,3-b]indol-2-yl)-(1H-pyrazol-3-yl)methanone | C16 H16 N4 O2 | + |
| 027 | 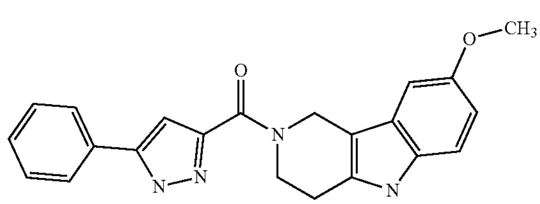 [SMILES: COc1ccc2[nH]c3c(c2c1)CN(C(=O)c1cc(-c2ccccc2)[nH]n1)CC3] | (8-methoxy-1,3,4,5-tetrahydropyrido[4,3-b]indol-2-yl)-(5-phenyl-1H-pyrazol-3-yl)methanone | C22 H20 N4 O2 | +++ |

TABLE 1-continued

| # | Compound structure | Substance Name | Substance Formula | Activity |
|---|---|---|---|---|
| 028 | 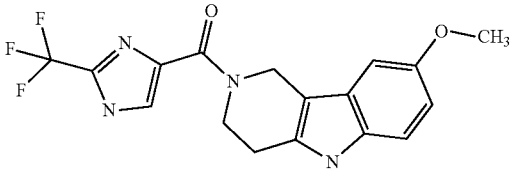 [SMILES: COc1ccc2[nH]c3c(c2c1)CN(C(=O)c1c[nH]c(C(F)(F)F)n1)CC3] | (8-methoxy-1,3,4,5-tetrahydropyrido[4,3-b]indol-2-yl)-[2-(trifluoromethyl)-1H-imidazol-4-yl]methanone | C17 H15 F3 N4 O2 | + |
| 029 | 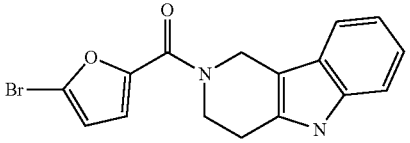 [SMILES: O=C(c1ccc(Br)o1)N1CCc2[nH]c3ccccc3c2C1] | (5-bromo-2-furyl)-(1,3,4,5-tetrahydropyrido[4,3-b]indol-2-yl)methanone | C16 H13 Br N2 O2 | ++ |
| 030 | 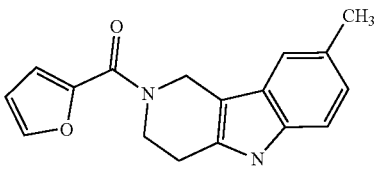 [SMILES: Cc1ccc2[nH]c3c(c2c1)CN(C(=O)c1ccco1)CC3] | 2-furyl-(8-methyl-1,3,4,5-tetrahydropyrido[4,3-b]indol-2-yl)methanone | C17 H16 N2 O2 | + |
| 031 | 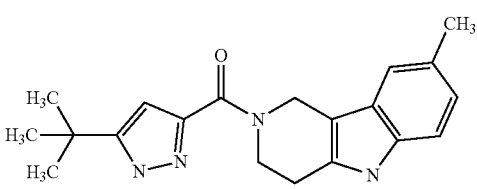 [SMILES: Cc1ccc2[nH]c3c(c2c1)CN(C(=O)c1cc(C(C)(C)C)[nH]n1)CC3] | (5-tert-butyl-1H-pyrazol-3-yl)-(8-methyl-1,3,4,5-tetrahydropyrido[4,3-b]indol-2-yl)methanone | C20 H24 N4 O | ++ |
| 032 | 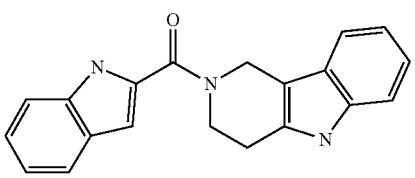 [SMILES: O=C(c1cc2ccccc2[nH]1)N1CCc2[nH]c3ccccc3c2C1] | 1H-indol-2-yl(1,3,4,5-tetrahydropyrido[4,3-b]indol-2-yl)methanone | C20 H17 N3 O | +++ |
| 033 | 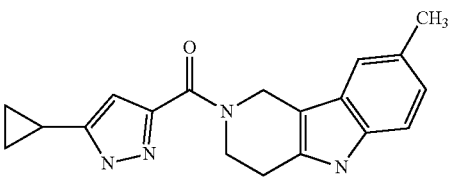 [SMILES: Cc1ccc2[nH]c3c(c2c1)CN(C(=O)c1cc(C2CC2)[nH]n1)CC3] | (5-cyclopropyl-1H-pyrazol-3-yl)-(8-methyl-1,3,4,5-tetrahydropyrido[4,3-b]indol-2-yl)methanone | C19 H20 N4 O | + |
| 034 | 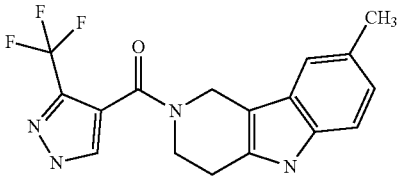 [SMILES: Cc1ccc2[nH]c3c(c2c1)CN(C(=O)c1c[nH]nc1C(F)(F)F)CC3] | (8-methyl-1,3,4,5-tetrahydropyrido[4,3-b]indol-2-yl)-[3-(trifluoromethyl)-1H-pyrazol-4-yl]methanone | C17 H15 F3 N4 O | + |
| 035 | 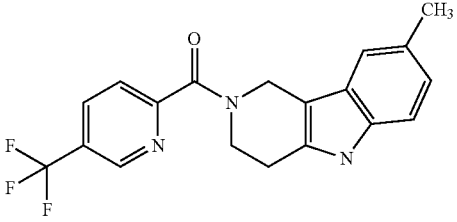 [SMILES: Cc1ccc2[nH]c3c(c2c1)CN(C(=O)c1ccc(C(F)(F)F)cn1)CC3] | (8-methyl-1,3,4,5-tetrahydropyrido[4,3-b]indol-2-yl)-[5-(trifluoromethyl)-2-pyridyl]methanone | C19 H16 F3 N3 O | + |

TABLE 1-continued

| # | Compound structure | Substance Name | Substance Formula | Activity |
|---|---|---|---|---|
| 036 | 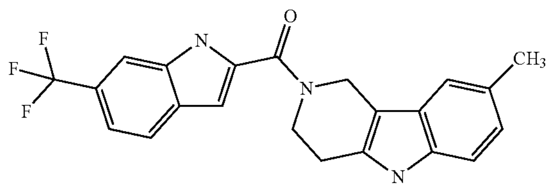 [SMILES: Cc1ccc2[nH]c3c(c2c1)CN(C(=O)c1cc2ccc(C(F)(F)F)cc2[nH]1)CC3] | (8-methyl-1,3,4,5-tetrahydropyrido[4,3-b]indol-2-yl)-[6-(trifluoromethyl)-1H-indol-2-yl]methanone | C22 H18 F3 N3 O | +++ |
| 037 | 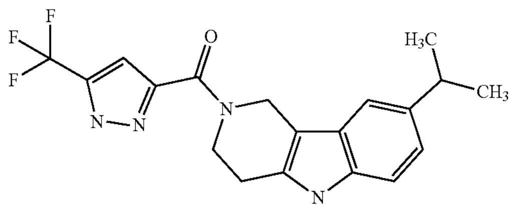 [SMILES: CC(C)c1ccc2[nH]c3c(c2c1)CN(C(=O)c1cc(C(F)(F)F)[nH]n1)CC3] | (8-isopropyl-1,3,4,5 tetrahydropyrido[4,3-b]indol-2-yl)-[5-(trifluoromethyl)-1H-pyrazol-3-yl]methanone | C19 H19 F3 N4 O | ++ |
| 038 | 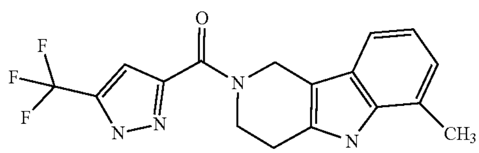 [SMILES: Cc1cccc2c3c([nH]c12)CCN(C(=O)c1cc(C(F)(F)F)[nH]n1)C3] | (6-methyl-1,3,4,5-tetrahydropyrido[4,3-b]indol-2-yl)-[5-(trifluoromethyl)-1H-pyrazol-3-yl]methanone | C17 H15 F3 N4 O | ++ |
| 039 | 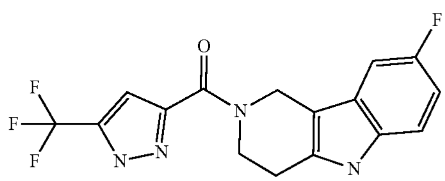 [SMILES: O=C(c1cc(C(F)(F)F)[nH]n1)N1CCc2[nH]c3ccc(F)cc3c2C1] | (8-fluoro-1,3,4,5-tetrahydropyrido[4,3-b]indol-2-yl)-[5-(trifluoromethyl)-1H-pyrazol-3-yl]methanone | C16 H12 F4 N4 O | +++ |
| 040 | 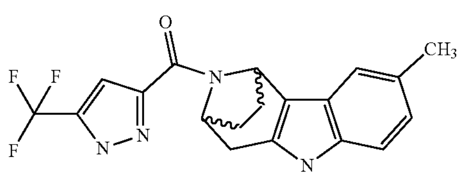 [SMILES: Cc1ccc2[nH]c3c(c2c1)C1CCC(C3)N1C(=O)c1cc(C(F)(F)F)[nH]n1] | (2-methyl-5,6,7,8,9,10-hexahydro-7,10-epiminocyclohepta[b]indol-11-yl)(5-(trifluoromethyl)-1H-pyrazol-3-yl)methanone | C19 H17 F3 N4 O | + |
| 041 | 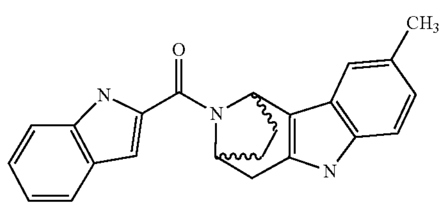 [SMILES: Cc1ccc2[nH]c3c(c2c1)C1CCC(C3)N1C(=O)c1cc2ccccc2[nH]1] | (1H-indol-2-yl)(2-methyl-5,6,7,8,9,10-hexahydro-7,10-epiminocyclohepta[b]indol-11-yl)methanone | C23 H21 N3 O | +++ |
| 042 | 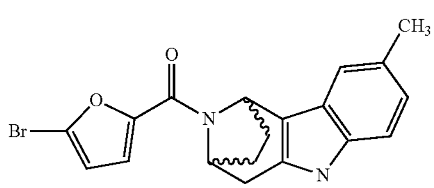 [SMILES: Cc1ccc2[nH]c3c(c2c1)C1CCC(C3)N1C(=O)c1ccc(Br)o1] | (5-bromofuran-2-yl)(2-methyl-5,6,7,8,9,10-hexahydro-7,10-epiminocyclohepta[b]indol-11-yl)methanone | C19 H17 Br N2 O2 | +++ |
| 043 | 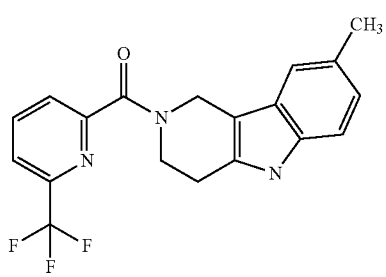 [SMILES: Cc1ccc2[nH]c3c(c2c1)CN(C(=O)c1cccc(C(F)(F)F)n1)CC3] | (8-methyl-1,3,4,5-tetrahydropyrido[4,3-b]indol-2-yl)-[6-(trifluoromethyl)-2-pyridyl]methanone | C19 H16 F3 N3 O | + |

TABLE 1-continued

| # | Compound structure | Substance Name | Substance Formula | Activity |
|---|---|---|---|---|
| 044 | 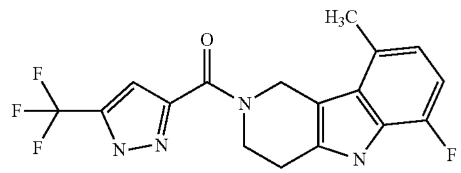 [SMILES: Cc1ccc(F)c2[nH]c3c(c12)CN(C(=O)c1cc(C(F)(F)F)[nH]n1)CC3] | (6-fluoro-9-methyl-1,3,4,5-tetrahydropyrido[4,3-b]indol-2-yl)-[5-(trifluoromethyl)-1H-pyrazol-3-yl]methanone | C17 H14 F4 N4 O | +++ |
| 045 | 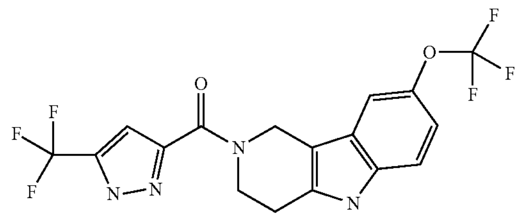 [SMILES: O=C(c1cc(C(F)(F)F)[nH]n1)N1CCc2[nH]c3ccc(OC(F)(F)F)cc3c2C1] | [8-(trifluoromethoxy)-1,3,4,5-tetrahydropyrido[4,3-b]indol-2-yl]-[5-(trifluoromethyl)-1H-pyrazol-3-yl]methanone | C17 H12 F6 N4 O2 | +++ |
| 046 | 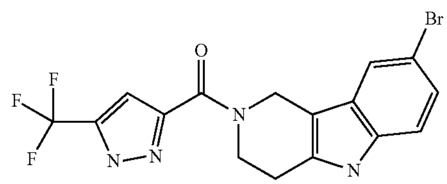 [SMILES: O=C(c1cc(C(F)(F)F)[nH]n1)N1CCc2[nH]c3ccc(Br)cc3c2C1] | (8-bromo-1,3,4,5-tetrahydropyrido[4,3-b]indol-2-yl)-[5-(trifluoromethyl)-1H-pyrazol-3-yl]methanone | C16 H12 Br F3 N4 O | +++ |
| 047 | 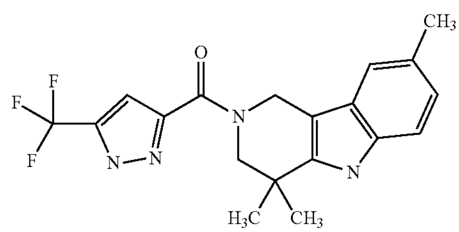 [SMILES: Cc1ccc2[nH]c3c(c2c1)CN(C(=O)c1cc(C(F)(F)F)[nH]n1)CC3(C)C] | [5-(trifluoromethyl)-1H-pyrazol-3-yl]-(4,4,8-trimethyl-3,5-dihydro-1H-pyrido[4,3-b]indol-2-yl)methanone | C19 H19 F3 N4 O | +++ |
| 048 | 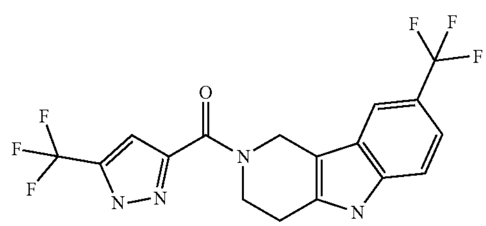 [SMILES: O=C(c1cc(C(F)(F)F)[nH]n1)N1CCc2[nH]c3ccc(C(F)(F)F)cc3c2C1] | [5-(trifluoromethyl)-1H-pyrazol-3-yl]-[8-(trifluoromethyl)-1,3,4,5-tetrahydropyrido[4,3-b]indol-2-yl]methanone | C17 H12 F6 N4 O | +++ |
| 049 | 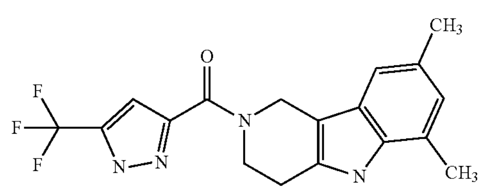 [SMILES: Cc1cc(C)c2[nH]c3c(c2c1)CN(C(=O)c1cc(C(F)(F)F)[nH]n1)CC3] | (6,8-dimethyl-1,3,4,5-tetrahydropyrido[4,3-b]indol-2-yl)-[5-(trifluoromethyl)-1H-pyrazol-3-yl]methanone | C18 H17 F3 N4 O | +++ |
| 050 | 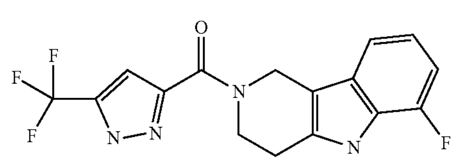 [SMILES: O=C(c1cc(C(F)(F)F)[nH]n1)N1CCc2[nH]c3c(F)cccc3c2C1] | (6-fluoro-1,3,4,5-tetrahydropyrido[4,3-b]indol-2-yl)-[5-(trifluoromethyl)-1H-pyrazol-3-yl]methanone | C16 H12 F4 N4 O | +++ |
| 051 | 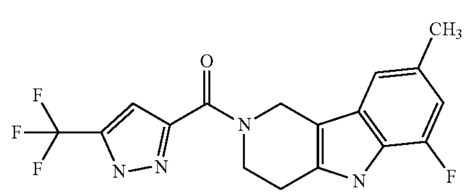 [SMILES: Cc1cc(F)c2[nH]c3c(c2c1)CN(C(=O)c1cc(C(F)(F)F)[nH]n1)CC3] | (6-fluoro-8-methyl-1,3,4,5-tetrahydropyrido[4,3-b]indol-2-yl)-[5-(trifluoromethyl)-1H-pyrazol-3-yl]methanone | C17 H14 F4 N4 O | +++ |

TABLE 1-continued

| # | Compound structure | Substance Name | Substance Formula | Activity |
|---|---|---|---|---|
| 052 | 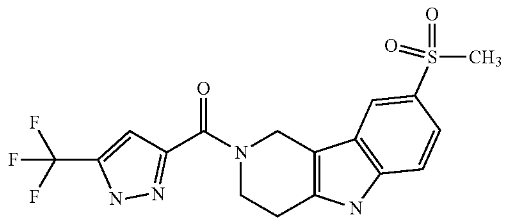 [SMILES: CS(=O)(=O)c1ccc2[nH]c3c(c2c1)CN(C(=O)c1cc(C(F)(F)F)[nH]n1)CC3] | (8-methylsulfonyl-1,3,4,5-tetrahydropyrido[4,3-b]indol-2-yl)-[5-(trifluoromethyl)-1H-pyrazol-3-yl]methanone | C17 H15 F3 N4 O3 S | + |
| 053 | 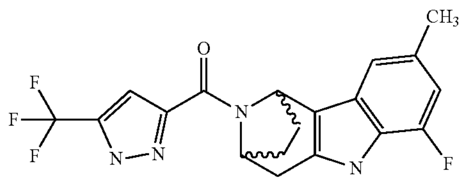 [SMILES: Cc1cc(F)c2[nH]c3c(c2c1)C1CCC(C3)N1C(=O)c1cc(C(F)(F)F)[nH]n1] | (4-fluoro-2-methyl-5,6,7,8,9,10-hexahydro-7,10-epiminocyclohepta[b]indol-11-yl)(5-(trifluoromethyl)-1H-pyrazol-3-yl)methanone | C19 H16 F4 N4 O | + |
| 054 | 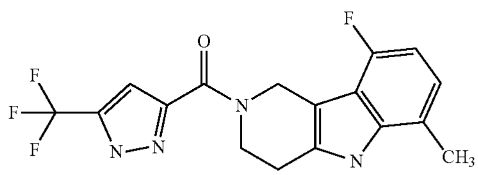 [SMILES: Cc1ccc(F)c2c3c([nH]c12)CCN(C(=O)c1cc(C(F)(F)F)[nH]n1)C3] | (9-fluoro-6-methyl-1,3,4,5-tetrahydropyrido[4,3-b]indol-2-yl)-[5-(trifluoromethyl)-1H-pyrazol-3-yl]methanone | C17 H14 F4 N4 O | +++ |
| 055 | 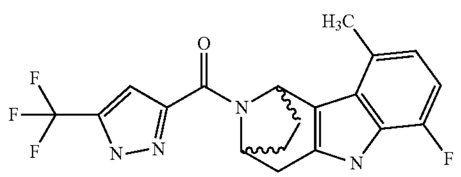 [SMILES: Cc1ccc(F)c2[nH]c3c(c12)C1CCC(C3)N1C(=O)c1cc(C(F)(F)F)[nH]n1] | (4-fluoro-1-methyl-5,6,7,8,9,10-hexahydro-7,10-epiminocyclohepta[b]indol-11-yl)(5-(trifluoromethyl)-1H-pyrazol-3-yl)methanone | C19 H16 F4 N4 O | ++ |
| 056 | 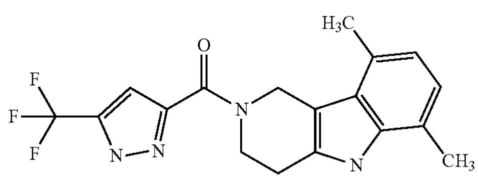 [SMILES: Cc1ccc(C)c2c3c([nH]c12)CCN(C(=O)c1cc(C(F)(F)F)[nH]n1)C3] | (6,9-dimethyl-1,3,4,5-tetrahydropyrido[4,3-b]indol-2-yl)-[5-(trifluoromethyl)-1H-pyrazol-3-yl]methanone | C18 H17 F3 N4 O | ++ |
| 057 | 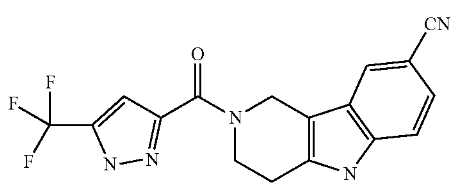 [SMILES: N#Cc1ccc2[nH]c3c(c2c1)CN(C(=O)c1cc(C(F)(F)F)[nH]n1)CC3] | 2-[5-(trifluoromethyl)-1H-pyrazole-3-carbonyl]-1,3,4,5-tetrahydropyrido[4,3-b]indole-8-carbonitrile | C17 H12 F3 N5 O | ++ |
| 058 | 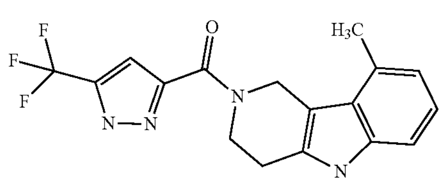 [SMILES: Cc1cccc2[nH]c3c(c12)CN(C(=O)c1cc(C(F)(F)F)[nH]n1)CC3] | (9-methyl-1,3,4,5-tetrahydropyrido[4,3-b]indol-2-yl)-[5-(trifluoromethyl)-1H-pyrazol-3-yl]methanone | C17 H15 F3 N4 O | +++ |
| 059 | 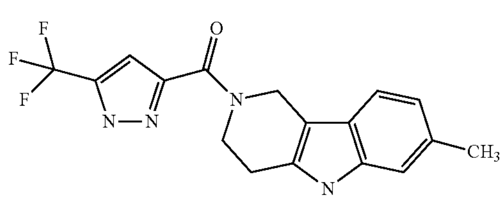 [SMILES: Cc1ccc2c3c([nH]c2c1)CCN(C(=O)c1cc(C(F)(F)F)[nH]n1)C3] | (7-methyl-1,3,4,5-tetrahydropyrido[4,3-b]indol-2-yl)-[5-(trifluoromethyl)-1H-pyrazol-3-yl]methanone | C17 H15 F3 N4 O | +++ |

TABLE 1-continued

| # | Compound structure | Substance Name | Substance Formula | Activity |
|---|---|---|---|---|
| 060 | 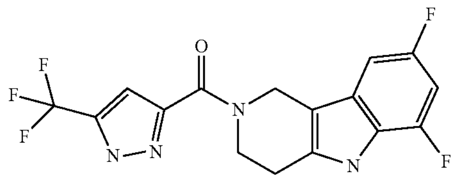 [SMILES: O=C(c1cc(C(F)(F)F)[nH]n1)N1CCc2[nH]c3c(F)cc(F)cc3c2C1] | (6,8-difluoro-1,3,4,5-tetrahydropyrido[4,3-b]indol-2-yl)-[5-(trifluoromethyl)-1H-pyrazol-3-yl]methanone | C16 H11 F5 N4 O | +++ |
| 061 | 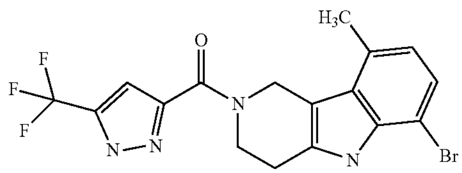 [SMILES: Cc1ccc(Br)c2[nH]c3c(c12)CN(C(=O)c1cc(C(F)(F)F)[nH]n1)CC3] | (6-bromo-9-methyl-1,3,4,5-tetrahydropyrido[4,3-b]indol-2-yl)-[5-(trifluoromethyl)-1H-pyrazol-3-yl]methanone | C17 H14 Br F3 N4 O | ++ |
| 063 | 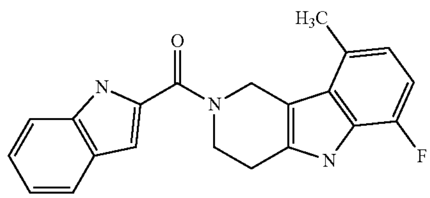 [SMILES: Cc1ccc(F)c2[nH]c3c(c12)CN(C(=O)c1cc2ccccc2[nH]1)CC3] | (6-fluoro-9-methyl-1,3,4,5-tetrahydropyrido[4,3-b]indol-2-yl)-(1H-indol-2-yl)methanone | C21 H18 F N3 O | +++ |
| 077 | 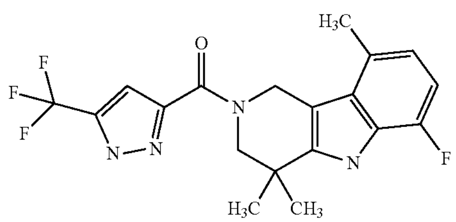 [SMILES: Cc1ccc(F)c2[nH]c3c(c12)CN(C(=O)c1cc(C(F)(F)F)[nH]n1)CC3(C)C] | (6-fluoro-4,4,9-trimethyl-3,5-dihydro-1H-pyrido[4,3-b]indol-2-yl)-[5-(trifluoromethyl)-1H-pyrazol-3-yl]methanone | C19 H18 F4 N4 O | +++ |
| 079 | 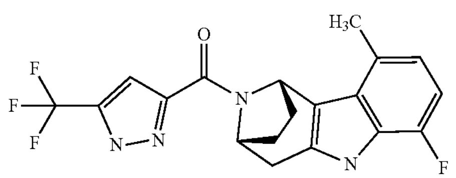 [SMILES: Cc1ccc(F)c2[nH]c3c(c12)[C@@H]1CC[C@H](C3)N1C(=O)c1cc(C(F)(F)F)[nH]n1] | (7R,10S)- or (7S,10R)-(4-fluoro-1-methyl 5,6,7,8,9,10-hexahydro-7,10 epiminocyclohepta[b]indol-11-yl) (5-(trifluoromethyl)-1H-pyrazol-3-yl)methanone | C19 H16 F4 N4 O | + |
| 080 | 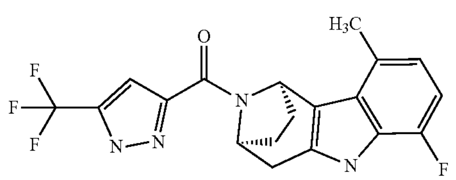 [SMILES: Cc1ccc(F)c2[nH]c3c(c12)[C@H]1CC[C@@H](C3)N1C(=O)c1cc(C(F)(F)F)[nH]n1] | (7S,10R)- or (7R,10S)-4-fluoro-1-methyl-5,6,7,8,9,10-hexahydro-7,10-epiminocyclohepta[b]indol-11-yl) (5-(trifluoromethyl)-1H-pyrazol-3-yl)methanone | C19 H16 F4 N4 O | +++ |
| 081 | 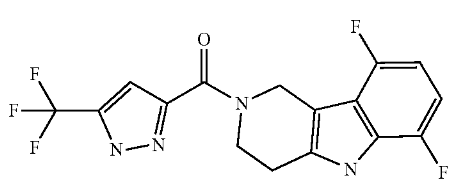 [SMILES: O=C(c1cc(C(F)(F)F)[nH]n1)N1CCc2[nH]c3c(F)ccc(F)c3c2C1] | (6,9-difluoro-1,3,4,5-tetrahydropyrido[4,3-b]indol-2-yl)-[5-(trifluoromethyl)-1H-pyrazol-3-yl]methanone | C16 H11 F5 N4 O | +++ |

TABLE 1-continued

| # | Compound structure | Substance Name | Substance Formula | Activity |
|---|---|---|---|---|
| 082 | 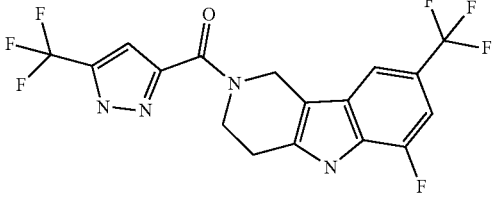 | (6-fluoro-8-(trifluoromethyl)-1,3,4,5-tetrahydropyrido[4,3-b]indol-2-yl]-[5-(trifluoromethyl)-1H-pyrazol-3-yl]methanone | C17 H11 F7 N4 O | +++ |
| 086 | 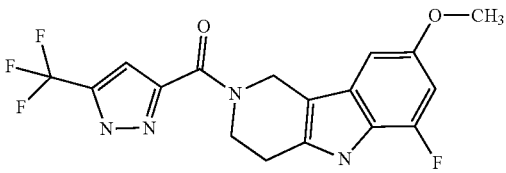 [SMILES: COc1cc(F)c2[nH]c3c(c2c1)CN(C(=O)c1cc(C(F)(F)F)[nH]n1)CC3] | (6-fluoro-8-methoxy-1,3,4,5-tetrahydropyrido[4,3-b]indol-2-yl]-[5-(trifluoromethyl)-1H-pyrazol-3-yl]methanone | C17 H14 F4 N4 O2 | +++ |
| 087 | 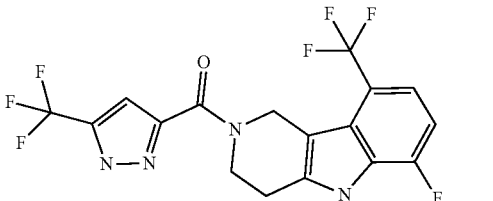 | [6-fluoro-9-(trifluoromethyl)-1,3,4,5-tetrahydropyrido[4,3-b]indol-2-yl]-[5-(trifluoromethyl)-1H-pyrazol-3-yl]methanone | C17 H11 F7 N4 O | +++ |
| 088 | 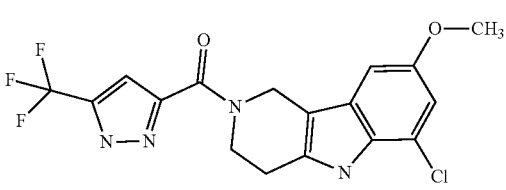 [SMILES: COc1cc(Cl)c2[nH]c3c(c2c1)CN(C(=O)c1cc(C(F)(F)F)[nH]n1)CC3] | (6-chloro-8-methoxy-1,3,4,5-tetrahydropyrido[4,3-b]indol-2-yl]-[5-(trifluoromethyl)-1H-pyrazol-3-yl]methanone | C17 H14 Cl F3 N4 O2 | +++ |
| 092 | 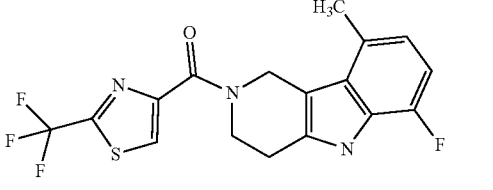 [SMILES: Cc1ccc(F)c2[nH]c3c(c12)CN(C(=O)c1csc(C(F)(F)F)n1)CC3] | (6-fluoro-9-methyl-1,3,4,5-tetrahydropyrido[4,3-b]indol-2-yl)-[2-(trifluoromethyl)thiazol-4-yl]methanone | C17 H13 F4 N3 O S | +++ |
| 093 | 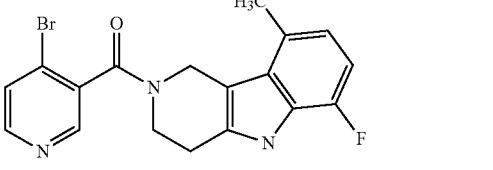 | (4-bromo-3-pyridyl)-(6-fluoro-9-methyl-1,3,4,5-tetrahydropyrido[4,3-b]indol-2-yl)methanone | C18 H15 Br F N3 O | + |
| 094 | 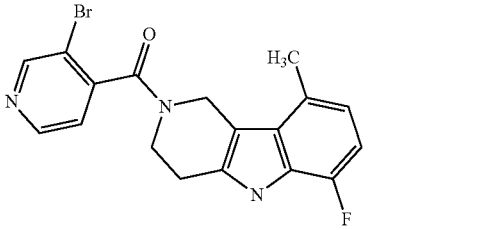 [SMILES: Cc1ccc(F)c2[nH]c3c(c12)CN(C(=O)c1ccncc1Br)CC3] | (3-bromo-4-pyridyl)-(6-fluoro-9-methyl-1,3,4,5-tetrahydropyrido[4,3-b]indol-2yl)methanone | C18 H15 Br F N3 O | + |

TABLE 1-continued

| # | Compound structure | Substance Name | Substance Formula | Activity |
|---|---|---|---|---|
| 095 | 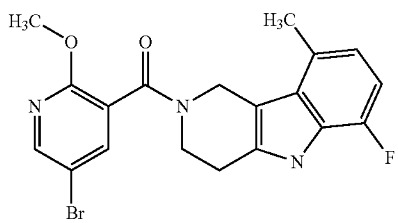 [SMILES: COc1ncc(Br)cc1C(=O)N1CCc2[nH]c3c(F)ccc(C)c3c2C1] | (5-bromo-2-methoxy-3-pyridyl)-(6-fluoro-9-methyl-1,3,4,5-tetrahydropyrido[4,3-b]indol-2-yl)methanone | C19 H17 Br F N3 O2 | + |
| 097 | 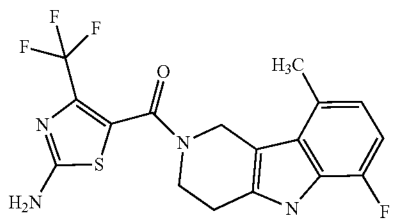 [SMILES: Cc1ccc(F)c2[nH]c3c(c12)CN(C(=O)c1sc(N)nc1C(F)(F)F)CC3] | [2-amino-4-(trifluoromethyl)thiazol-5-yl]-(6-fluoro-9-methyl-1,3,4,5-tetrahydropyrido[4,3-b]indol-2-yl)methanone | C17 H14 F4 N4 O S | + |
| 098 | 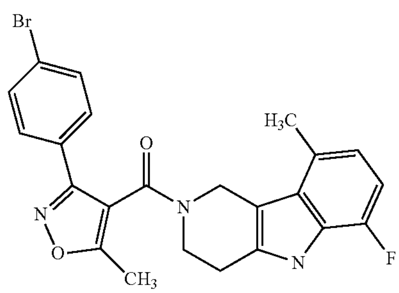 [SMILES: Cc1onc(-c2ccc(Br)cc2)c1C(=O)N1CCc2[nH]c3c(F)ccc(C)c3c2C1] | [3-(4-bromophenyl)-5-methyl-isoxazol-4-yl]-(6-fluoro-9-methyl-1,3,4,5-tetrahydropyrido[4,3-b]indol-2-yl)methanone | C23 H19 Br F N3 O2 | + |
| 104 | 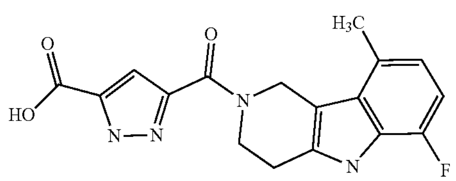 [SMILES: Cc1ccc(F)c2[nH]c3c(c12)CN(C(=O)c1cc(C(=O)O)[nH]n1)CC3] | 3-(6-fluoro-9-methyl 1,3,4,5-tetrahydropyrido[4,3-b]indole-2-carbonyl)-1H-pyrazole-5-carboxylic acid | C17 H15 F N4 O3 | + |
| 105 | 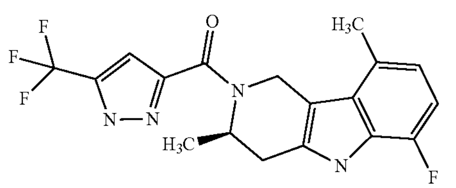 [SMILES: Cc1ccc(F)c2[nH]c3c(c12)CN(C(=O)c1cc(C(F)(F)F)[nH]n1)[C@H](C)C3] | rac-(6-fluoro-3,9-dimethyl-1,3,4,5-tetrahydropyrido[4,3-b]indol-2-yl)-[5-(trifluoromethyl)-1H-pyrazol-3-yl]methanone | C18 H16 F4 N4 O | +++ |
| 106 | 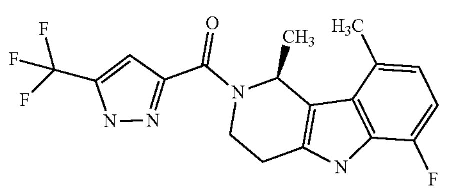 [SMILES: Cc1ccc(F)c2[nH]c3c(c12)[C@H](C)N(C(=O)c1cc(C(F)(F)F)[nH]n1)CC3] | rac-(6-fluoro-1,9-dimethyl-1,3,4,5-tetrahydropyrido[4,3-b]indol-2-yl)-[5-(trifluoromethyl)-1H-pyrazol-3-yl]methanone | C18 H16 F4 N4 O | +++ |
| 107 | 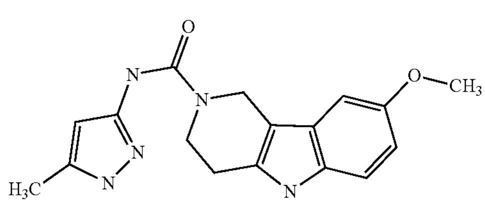 | 8-methoxy-N-(5-methyl-1H-pyrazol-3-yl)-1,3,4,5-tetrahydropyrido[4,3-b]indole-2-carboxamide | C17 H19 N5 O2 | + |

TABLE 1-continued

| # | Compound structure | Substance Name | Substance Formula | Activity |
|---|---|---|---|---|
| 108 | 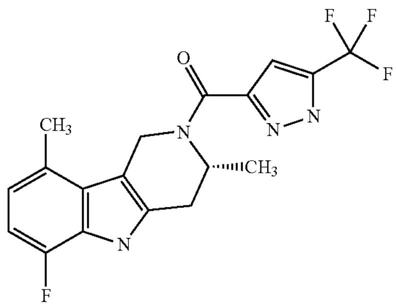 [SMILES: Cc1ccc(F)c2[nH]c3c(c12)CN(C(=O)c1cc(C(F)(F)F)[nH]n1)[C@H](C)C3] | (R)-(6-fluoro-3,9-dimethyl 1,3,4,5-tetrahydropyrido[4,3-b]indol-2-yl)-[5-(trifluoromethyl)-1H-pyrazol-3-yl]methanone | C18 H16 F4 N4 O | +++ |
| 109 | 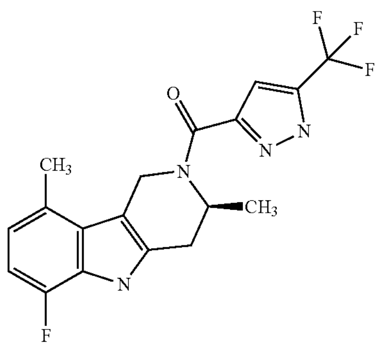 [SMILES: Cc1ccc(F)c2[nH]c3c(c12)CN(C(=O)c1cc(C(F)(F)F)[nH]n1)[C@@H](C)C3] | (R)-(6-fluoro-3,9-dimethyl 1,3,4,5-tetrahydropyrido[4,3-b]indol-2-yl)-[5-(trifluoromethyl)-1H-pyrazol-3-yl]methanone | C18 H16 F4 N4 O | +++ |
| 112 | 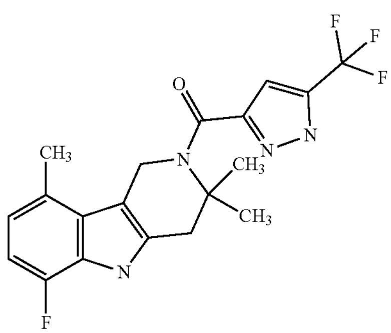 [SMILES: Cc1ccc(F)c2[nH]c3c(c12)CN(C(=O)c1cc(C(F)(F)F)[nH]n1)C(C)(C)C3] | (6-fluoro-3,3,9-trimethyl-4,5-dihydro-1H-pyrido[4,3-b]indol-2-yl)-[5-(trifluoromethyl)-1H-pyrazol-3-yl]methanone | C19 H18 F4 N4 O | ++ |
| 113 | 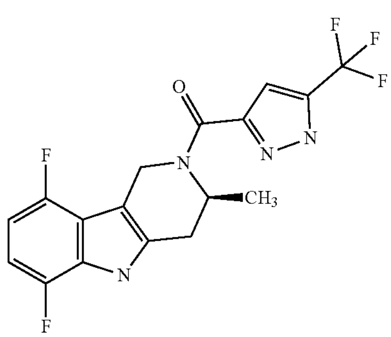 [SMILES: C[C@H]1Cc2[nH]c3c(F)ccc(F)c3c2CN1C(=O)c1cc(C(F)(F)F)[nH]n1] | [(S)-6,9-difluoro-3-methyl-1,3,4,5-tetrahydropyrido[4,3-b]indol-2-yl]-[5-(trifluoromethyl)-1H-pyrazol-3-yl]methanone | C17 H13 F5 N4 O | +++ |
| 114 | 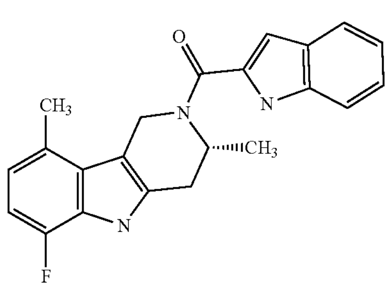 [SMILES: Cc1ccc(F)c2[nH]c3c(c12)CN(C(=O)c1cc2ccccc2[nH]1)[C@H](C)C3] | [(R)-6-fluoro-3,9-dimethyl 1,3,4,5-tetrahydropyrido[4,3-b]indol-2-yl]-(1H-indol-2-yl)methanone | C22 H20 F N3 O | ++ |

TABLE 1-continued

| # | Compound structure | Substance Name | Substance Formula | Activity |
|---|---|---|---|---|
| 115 | 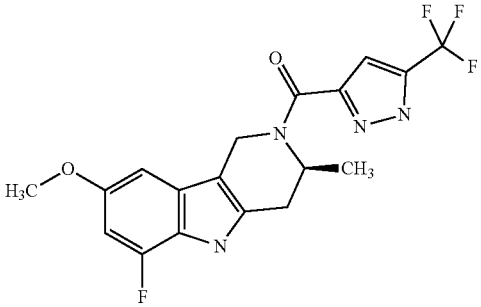 [SMILES: COc1cc(F)c2[nH]c3c(c2c1)CN(C(=O)c1cc(C(F)(F)F)[nH]n1)[C@@H](C)C3] | [(S)-8-methoxy-6-fluoro-3-methyl-1,3,4,5-tetrahydropyrido[4,3-b]indol-2-yl]-[5-(trifluoromethyl)-1H-pyrazol-3-yl]methanone | C18 H16 F4 N4 O2 | +++ |
| 116 | 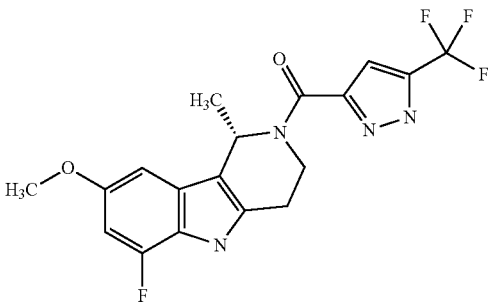 [SMILES: COc1cc(F)c2[nH]c3c(c2c1)[C@H](C)N(C(=O)c1cc(C(F)(F)F)[nH]n1)CC3] | rac-(6-fluoro-1-methyl-8-methoxy-1,3,4,5-tetrahydropyrido[4,3-b]indol-2-yl)-(5 (trifluoromethyl)-1H-pyrazol-3-yl)methanone | C18 H16 F4 N4 O2 | +++ |
| 117 | 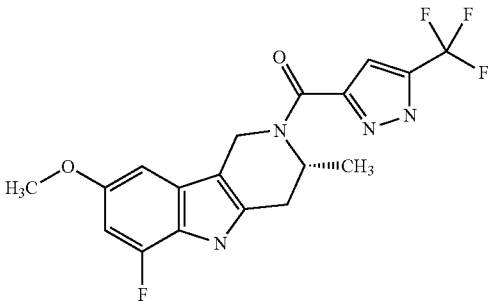 [SMILES: COc1cc(F)c2[nH]c3c(c2c1)CN(C(=O)c1cc(C(F)(F)F)[nH]n1)[C@H](C)C3] | [(R)-8-methoxy-6-fluoro-3-methoxy-1,3,4,5-tetrahydropyrido[4,3-b]indol-2-yl)-[5 (trifluoromethyl)-1H-pyrazol-3-yl]methanone | C18 H16 F4 N4 O2 | +++ |

The invention claimed is:

1. A compound of Formula (Ia):

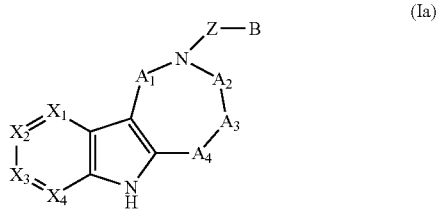

or pharmaceutically acceptable salts, hydrates, solvates, clathrates, polymorphs, or stereoisomers thereof wherein:

Z is selected from the group consisting of C=O, SO₂ or CONR$^i$;

R$^i$ is selected from the group consisting of hydrogen, $C_{1-6}$alkyl, $C_{3-6}$cycloalkyl, and heterocycloalkyl;

$X_1$, $X_2$, $X_3$ and $X_4$ are independently selected from the group consisting of CR$^{ii}$ and N, with the proviso that the number of nitrogen atoms in the ring is comprised from 0 to 2;

each R$^{ii}$ is independently selected from the group consisting of hydrogen, $C_{1-6}$alkyl, halo$C_{1-6}$alkyl, $C_{3-6}$cycloalkyl, heterocycloalkyl, aryl, heteroaryl, O-aryl, O-heteroaryl, COR$^{viii}$, COOR$^{viii}$, CONHR$^c$, CONR$^d$R$^e$, OH, O—$C_{1-6}$alkyl, O—$C_{3-6}$cycloalkyl, O-heterocycloalkyl, O-halo$C_{1-6}$alkyl, $C_{1-6}$alkyl-O—$C_{1-6}$alkyl, $C_{1-6}$alkyl-O—$C_{3-6}$cycloalkyl, $C_{1-6}$alkyl-O-heterocycloalkyl, CN, NO₂, NHR$^c$, NR$^d$R$^e$, N(R$^e$)COR$^c$, N(R$^e$)COOR$^c$, N(R$^x$)CONR$^{ix}$R$^x$, N(R$^x$)SO₂R$^{xi}$, SO₂R$^{xi}$, SO₂NHR$^c$, SO₂NR$^d$R$^e$, halogen, and hydroxy-$C_{1-6}$alkyl;

$A_1$ and $A_4$ are CR$^{iii}$R$^{iv}$, $A_2$ and $A_3$ are selected from a bond and CR$^{iii}$R$^{iv}$;

R$^{iii}$ and R$^{iv}$ are independently selected from the group consisting of hydrogen, $C_{1-6}$alkyl, $C_{3-6}$cycloalkyl, heterocycloalkyl, halo$C_{1-6}$alkyl, COR$^{viii}$, COOR$^{viii}$, CONHR$^{viii}$, CONR$^{ix}$R$^x$, OH, and O—$C_{1-6}$alkyl, $C_{1-6}$alkyl-O—$C_{1-6}$alkyl, CN, halogen, NR$^{ix}$R$^x$, and N(R$^{ix}$)COR$^{viii}$, or R$^{iii}$ and R$^{iv}$ form a $C_3$-$C_6$ cycloalkyl with the C to which they are linked;

or, when $A_3$ is a bond, two groups R$^{iv}$ on $A_1$ and $A_2$, or on $A_1$ and $A_4$ are linked together to form a ring and thus the moiety

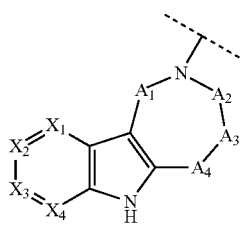

represents one of the structures selected from the group consisting of:

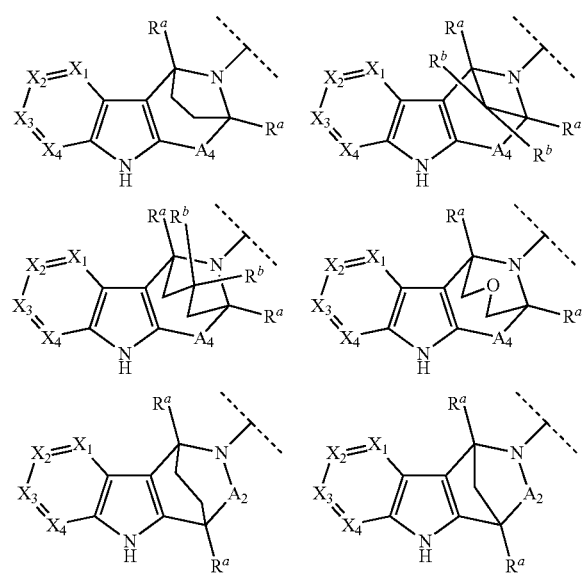

wherein $R^a$ and $R^b$ are independently selected from the group consisting of hydrogen, $C_{1-6}$alkyl, halogen, OH, O—$C_{1-6}$alkyl, and $C_{1-6}$alkyl-O—$C_{1-6}$alkyl, B is selected from the group consisting of:

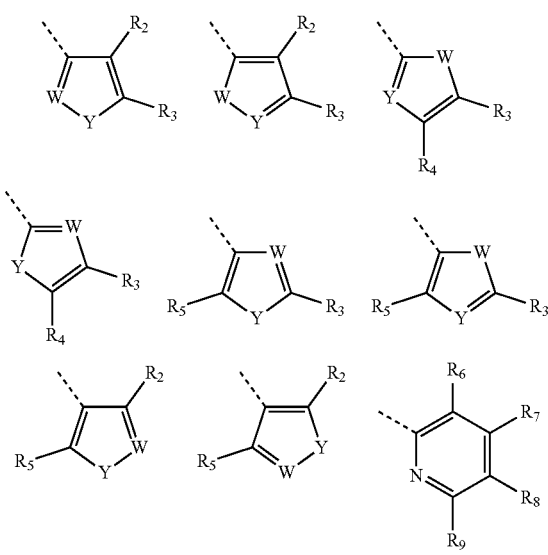

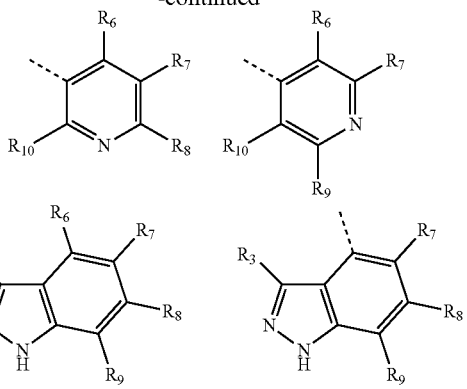

wherein
Y and W are independently selected from the group consisting of O, S, $CR^v$, $CR^vR^{vi}$, N, and $NR^{vii}$, wherein $R^v$ and $R^{vi}$ are selected form the group consisting of hydrogen, $C_{1-6}$alkyl, halo$C_{1-6}$alkyl, $C_{3-6}$cycloalkyl, heterocycloalkyl, aryl, heteroaryl, O—$C_{1-6}$alkyl, O—$C_{1-6}$alkylaryl, O—$C_{3-6}$cycloalkyl, O-heterocycloalkyl, O-halo$C_{1-6}$alkyl, $C_{1-6}$alkyl-O—$C_{1-6}$alkyl, $C_{1-6}$alkyl-O—$C_{3-6}$cycloalkyl, $C_{1-6}$alkyl-O-heterocycloalkyl, $C_{1-6}$alkyl-O-aryl, $C_{1-6}$alkyl-O-heteroaryl, hydroxy-$C_{1-6}$alkyl, $COR^{vii}$, $COOR^{viii}$, $CONHR^{viii}$, and $CONR^{ix}R^x$;

$R^{vii}$ is selected form the group consisting of hydrogen, $C_{1-6}$alkyl, halo$C_{1-6}$alkyl, $C_{3-6}$cycloalkyl, heterocycloalkyl, aryl, heteroaryl, $C_{2-6}$alkyl-O—$C_{1-6}$alkyl, $C_{2-6}$alkyl-O—$C_{3-6}$cycloalkyl, $C_{2-6}$alkyl-O-heterocycloalkyl, $C_{2-6}$alkyl-O-aryl, and $C_{2-6}$alkyl-O-heteroaryl;

$R_2$, $R_3$, $R_4$, $R_5$, $R_6$, $R_7$, $R_8$, $R_9$ and $R_{10}$ are independently selected from the group consisting of hydrogen, $C_{1-6}$alkyl, halo$C_{1-6}$alkyl, $C_{3-6}$cycloalkyl, heterocycloalkyl, aryl, heteroaryl, $COR^{viii}$, $COOR^{viii}$, $CONHR^{viii}$, $CONR^{ix}R^x$, OH, O—$C_{1-6}$alkyl, O—$C_{1-6}$alkylaryl, O—$C_{3-6}$cycloalkyl, O-heterocycloalkyl, O-heteroaryl, O-aryl, O-halo$C_{1-6}$alkyl, $C_{1-6}$alkyl-O—$C_{1-6}$alkyl, $C_{1-6}$alkyl-O—$C_{3-6}$cycloalkyl, $C_{1-6}$alkyl-O-heterocycloalkyl, $C_{1-6}$alkyl-O-aryl, $C_{1-6}$alkyl-O-heteroaryl, hydroxy-$C_{1-6}$alkyl, CN, $NO_2$, $NR^{ix}R^x$, $N(R^x)COR^{viii}$, $N(R^x)COOR^{viii}$, $N(R^x)CONR^{ix}R^x$, $N(R^x)SO_2R^{xi}$, $SO_2R^{xi}$, $SO_2NR^{ix}R^x$, and halogen;

$R^{viii}$ is selected from the group consisting of hydrogen, $C_{1-6}$alkyl, halo$C_{1-6}$alkyl, $C_{3-6}$cycloalkyl, heterocycloalkyl, aryl, heteroaryl, $C_{1-6}$alkyl-O—$C_{1-6}$alkyl, and $C_{1-6}$alkyl-O-heterocycloalkyl;

$R^{ix}$ is selected from the group consisting of hydrogen, $C_{1-6}$alkyl, halo$C_{1-6}$alkyl, $C_{3-6}$cycloalkyl, heterocycloalkyl, aryl, and heteroaryl;

$R^x$ is selected from the group consisting of hydrogen, $C_{1-6}$alkyl, halo$C_{1-6}$alkyl, $C_{3-6}$cycloalkyl, heterocycloalkyl, aryl, heteroaryl, $C_{1-6}$alkyl-O—$C_{2-6}$alkyl, and hydroxy-$C_{2-6}$alkyl;

$R^{xi}$ is selected from the group consisting of $C_{1-6}$alkyl, halo$C_{1-6}$alkyl, $C_{3-6}$cycloalkyl, heterocycloalkyl, aryl, and heteroaryl;

$R^c$ is selected from the group consisting of hydrogen, $C_{1-6}$alkyl, halo$C_{1-6}$alkyl, $C_{2-6}$alkyl-O—$C_{1-6}$alkyl, and $C_{2-6}$alkyl-O-heterocycloalkyl;

$R^d$ is selected from the group consisting of $C_{1-6}$alkyl, halo$C_{1-6}$alkyl, aryl, and heteroaryl;

R$^e$ is selected from the group consisting of C$_{1-6}$alkyl, haloC$_{1-6}$alkyl, aryl, heteroaryl, C$_{1-6}$alkyl-O—C$_{2-6}$alkyl, and hydroxy-C$_{2-6}$alkyl;

provided that at least one of R$^{iii}$ or R$^{iv}$ of at least one of A$_1$, A$_2$, A$_3$ or A$_4$ is not H and that, when Z is C=O, A$_1$ is not CH(C$_{1-6}$alkyl) when A$_4$ is CH$_2$ or A$_1$ is not CH$_2$ when A$_4$ is CH(C$_{1-6}$alkyl).

2. The compound of Formula (Ia) according to claim 1 wherein Z is C=O;
X$_1$, X$_2$, X$_3$ and X$_4$ are CR$^{ii}$;
each R$^{ii}$ is independently selected from the group consisting of hydrogen, C$_{1-6}$alkyl, haloC$_{1-6}$alkyl, C$_{3-6}$cycloalkyl, heterocycloalkyl, COR$^{viii}$, COOR$^{viii}$, CONHR$^c$, CONR$^d$R$^e$, OH, O—C$_{1-6}$alkyl, O—C$_{3-6}$cycloalkyl, O-heterocycloalkyl, O-haloC$_{1-6}$alkyl, C$_{1-6}$alkyl-O—C$_{1-6}$alkyl, C$_{1-6}$alkyl-O—C$_{3-6}$cycloalkyl, C$_{1-6}$alkyl-O-heterocycloalkyl, CN, NO$_2$, NHR$^c$, NR$^d$R$^e$, SO$_2$R$^{xi}$, SO$_2$NHR$^c$, SO$_2$NR$^d$R$^e$, halogen, and hydroxy-C$_{1-6}$alkyl;
R$^{iii}$ and R$^{iv}$ are independently selected from the group consisting of hydrogen, C$_{1-6}$alkyl, C$_{3-6}$cycloalkyl, heterocycloalkyl, haloC$_{1-6}$alkyl, COR$^{viii}$, COOR$^{viii}$, CONHR$^{viii}$, CONR$^{ix}$R$^x$, OH, O—C$_{1-6}$alkyl, C$_{1-6}$alkyl-O—C$_{1-6}$alkyl, CN, and halogen.

3. The compound of Formula (Ia) according to claim 1 wherein R$^{iii}$ and R$^{iv}$ are independently selected from the group consisting of hydrogen, C$_{1-6}$alkyl, haloC$_{1-6}$alkyl, OH, O—C$_{1-6}$alkyl, and halogen or, when A$_3$ is a bond, two groups R$^{iv}$ on A$_1$ and A$_2$, are linked together to form a ring and thus the moiety

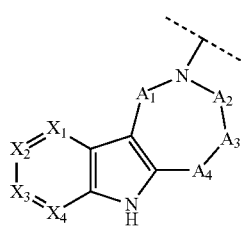

represents:

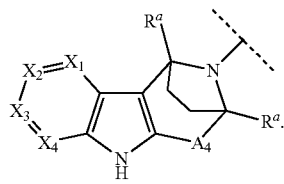

4. The compound of Formula (Ia) according to claim 1 wherein R$^{iii}$ and R$^{iv}$ are independently selected from the group consisting of hydrogen and methyl.

5. The compound of Formula (Ia) according to claim 1, selected from the group consisting of:

040 (2-methyl-5,6,7,8,9,10-hexahydro-7,10-epiminocyclohepta[b]indol-11-yl)(5-(trifluoromethyl)-1H-pyrazol-3-yl)methanone
041 (1H-indol-2-yl)(2-methyl-5,6,7,8,9,10-hexahydro-7,10-epiminocyclohepta[b]indol-11-yl)methanone
042 (5-bromofuran-2-yl)(2-methyl-5,6,7,8,9,10-hexahydro-7,10-epiminocyclohepta[b]indol-11-yl)methanone -continued 047 [5-(trifluoromethyl)-1H-pyrazol-3-yl]-(4,4,8-trimethyl-3,5-dihydro-1H-pyrido[4,3-b]indol-2-yl)methanone
053 (4-fluoro-2-methyl-5,6,7,8,9,10-hexahydro-7,10-epiminocyclohepta[b]indol-11-yl)(5-(trifluoromethyl)-1H-pyrazol-3-yl)methanone
055 (4-fluoro-1-methyl-5,6,7,8,9,10-hexahydro-7,10-epiminocyclohepta[b]indol-11-yl)(5-(trifluoromethyl)-1H-pyrazol-3-yl)methanone
077 (6-fluoro-4,4,9-trimethyl-3,5-dihydro-1H-pyrido[4,3-b]indol-2-yl)-[5-(trifluoromethyl)-1H-pyrazol-3-yl]methanone
079 (7R,10S)- or (7S,10R)-(4-fluoro-1-methyl-5,6,7,8,9,10-hexahydro-7,10-epiminocyclohepta [b]indol-11-yl)(5-(trifluoromethyl)-1H-pyrazol-3-yl)methanone
080 (7S,10R)- or (7R,10S)-4-fluoro-1-methyl-5,6,7,8,9,10-hexahydro-7,10-epiminocyclohepta [b]indol-11-yl)(5-(trifluoromethyl)-1H-pyrazol-3-yl)methanone
105 rac-(6-fluoro-3,9-dimethyl-1,3,4,5-tetrahydropyrido[4,3-b]indol-2-yl)-[5-(trifluoromethyl)-1H-pyrazol-3-yl]methanone
108 (R)-(6-fluoro-3,9-dimethyl-1,3,4,5-tetrahydropyrido[4,3-b]indol-2-yl)-[5-(trifluoromethyl)-1H-pyrazol-3-yl]methanone
109 (S)-(6-fluoro-3,9-dimethyl-1,3,4,5-tetrahydropyrido[4,3-b]indol-2-yl)-[5-(trifluoromethyl)-1H-pyrazol-3-yl]methanone
112 (6-fluoro-3,3,9-trimethyl-4,5-dihydro-1H-pyrido[4,3-b]indol-2-yl)-[5-(trifluoromethyl)-1H-pyrazol-3-yl]methanone
113 [(S)-6,9-difluoro-3-methyl-1,3,4,5-tetrahydropyrido[4,3-b]indol-2-yl]-[5-(trifluoromethyl)-1H-pyrazol-3-yl]methanone
114 [(R)-6-fluoro-3,9-dimethyl-1,3,4,5-tetrahydropyrido[4,3-b]indol-2-yl]-(1H-indol-2-yl)methanone
115 [(S)-8-methoxy-6-fluoro-3-methyl-1,3,4,5-tetrahydropyrido[4,3-b]indol-2-yl]-[5-(trifluoromethyl)-1H-pyrazol-3-yl]methanone
117 (R)-8-methoxy-6-fluoro-3-methyl-1,3,4,5-tetrahydropyrido[4,3-b]indol-2-yl]-[5-(trifluoromethyl)-1H-pyrazol-3-yl]methanone
121 (6-fluoro-3-isopropyl-8-methoxy-1,3,4,5-tetrahydropyrido[4,3-b]indol-2-yl)-(5-methyl-1H-pyrazol-3-yl)methanone
122 (6,9-difluoro-8-methoxy-spiro[4,5-dihydro-3H-pyrido[4,3-b]indole-1,1'-cyclopropane]-2-yl)-(5-methyl-1H-pyrazol-3-yl)methanone
123 (6,9-difluoro-1,3-dimethyl-1,3,4,5-tetrahydropyrido[4,3-b]indol-2-yl)-(5-methyl-1H-pyrazol-3-yl)methanone
124 (6,9-difluoro-8-methoxy-spiro[4,5-dihydro-1H-pyrido[4,3-b]indole-3,1'-cyclopropane]-2-yl)-(5-methyl-1H-pyrazol-3-yl)methanone
125 [6-(dimethylamino)-1H-indol-2-yl]-(8-methylspiro[3,5-dihydro-1H-pyrido[4,3-b]indole-4,1'-cyclopropane]-2-yl)methanone
126 (4-ethyl-6-fluoro-9-methyl-1,3,4,5-tetrahydropyrido[4,3-b]indol-2-yl)-(5-methyl-1H-pyrazol-3-yl)methanone
127 6-fluoro-9-methyl-2-(5-methyl-1H-pyrazole-3-carbonyl)-1,3,4,5-tetrahydropyrido[4,3-b]indole-3-carboxylic acid
128 [6-(dimethylamino)-1H-indol-2-yl]-[8-methyl-1-(trifluoromethyl)-1,3,4,5-tetrahydropyrido[4,3-b]indol-2-yl]methanone
129 (6-fluoro-8-methoxy-1,4-dimethyl-1,3,4,5-tetrahydropyrido[4,3-b]indol-2-yl)-(5-methyl-1H-pyrazol-3-yl)methanone
130 (6-fluoro-4-methoxy-9-methyl-1,3,4,5-tetrahydropyrido[4,3-b]indol-2-yl)-(5-methyl-1H-pyrazol-3-yl)methanone
131 6-fluoro-4,9-dimethyl-2-(5-methyl-1H-pyrazole-3-carbonyl)-3,5-dihydro-1H-pyrido[4,3-b]indole-4-carboxylic acid
132 (4,4-difluoro-8-methoxy-3,5-dihydro-1H-pyrido[4,3-b]indol-2-yl)-(5-methyl-1H-pyrazol-3-yl)methanone
133 (3,6-dimethyl-4,8,10-triazatricyclo[7.4.0.02,7]trideca-1(9),2(7),10,12-tetraen-4-yl)-(5-methyl-1H-pyrazol-3-yl)methanone
134 (6,6-dimethyl-4,8,12-triazatricyclo[7.4.0.02,7]trideca-1(9),2(7),10,12-tetraen-4-yl)-(5-methyl-1H-pyrazol-3-yl)methanone and
135 2-(5-bromofuran-2-carbonyl)-8-methoxy-1,3,4,5-tetrahydropyrido[4,3-b]indole-4-carboxylic acid.

6. A pharmaceutical composition comprising a compound of Formula (Ia) according to claim 1 and a pharmaceutically acceptable carrier, stabilizer, diluent, or excipient thereof.

7. A compound of Formula (Ia) according claim 1 for the use as a medicament.

8. A compound of Formula (Ib)

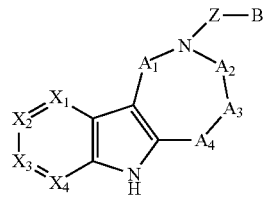
(Ib)

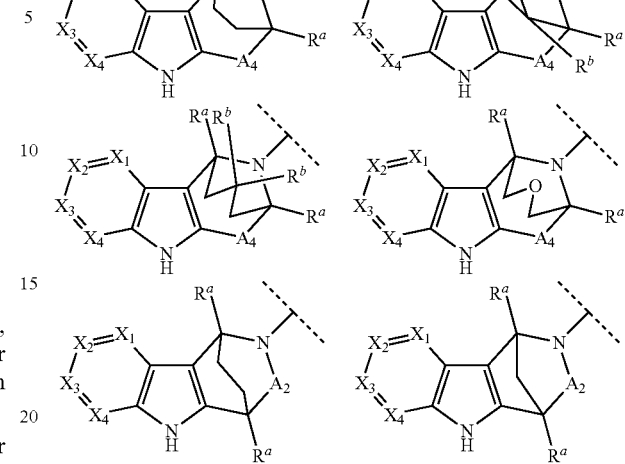

or pharmaceutically acceptable salts, hydrates, solvates, clathrates, polymorphs, or stereoisomers thereof, for the use to potentiate CFTR protein or ABC protein activities wherein:

Z is selected from the group consisting of C=O, SO$_2$ or CONR$^i$;

R$^i$ is selected from the group consisting of hydrogen, C$_{1-6}$alkyl, C$_{3-6}$cycloalkyl, and heterocycloalkyl;

X$_1$, X$_2$, X$_3$ and X$_4$ are independently selected from the group consisting of CR$^{ii}$ and N, with the proviso that the number of nitrogen atoms in the ring is comprised from 0 to 2;

each R$^{ii}$ is independently selected from the group consisting of hydrogen, C$_{1-6}$alkyl, haloC$_{1-6}$alkyl, C$_{3-6}$cycloalkyl, heterocycloalkyl, aryl, heteroaryl, O-aryl, O-heteroaryl, COR$^{viii}$, COOR$^{viii}$, CONHR$^{viii}$, CONR$^{ix}$R$^x$, OH, O—C$_{1-6}$alkyl, O—C$_{3-6}$cycloalkyl, O-heterocycloalkyl, O-haloC$_{1-6}$alkyl, C$_{1-6}$alkyl-O—C$_{1-6}$alkyl, C$_{1-6}$alkyl-O—C$_{3-6}$cycloalkyl, C$_{1-6}$alkyl-O-heterocycloalkyl, CN, NO$_2$, NR$^{ix}$R$^x$, N(R$^x$)COR$^{viii}$, N(R$^x$)COOR$^{viii}$, N(R$^x$)CONR$^{ix}$R$^x$, N(R$^x$)SO$_2$R$^{xi}$, SO$_2$R$^{xi}$, SO$_2$NR$^{ix}$R$^x$, halogen, and hydroxy-C$_{1-6}$alkyl;

A$_1$ and A$_4$ are CR$^{iii}$R$^{iv}$,

A$_2$ and A$_3$ are selected from a bond and CR$^{iii}$R$^{iv}$;

R$^{iii}$ and R$^{iv}$ are independently selected from the group consisting of hydrogen, C$_{1-6}$alkyl, C$_{3-6}$cycloalkyl, heterocycloalkyl, haloC$_{1-6}$alkyl, COR$^{viii}$, COOR$^{viii}$, CONHR$^{viii}$, CONR$^{ix}$R$^x$, OH, and O—C$_{1-6}$alkyl, C$_{1-6}$alkyl-O—C$_{1-6}$alkyl, CN, halogen, NR$^{ix}$R$^x$, and N(R$^{ix}$)COR$^{viii}$, or R$^{iii}$ and R$^{iv}$ form a C$_3$-C$_6$ cycloalkyl with the C to which they are linked;

or when A$_3$ is a bond, two groups R$^{iv}$ on A$_1$ and A$_2$, or on A$_1$ and A$_4$ are linked together to form a ring and thus the moiety

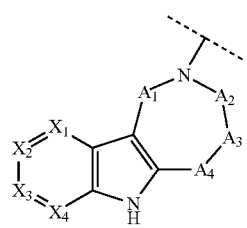

represents one of the structures selected from the group consisting of:

wherein R$^a$ and R$^b$ are independently selected from the group consisting of hydrogen, C$_{1-6}$alkyl, B halogen, OH, O—C$_{1-6}$alkyl, and C$_{1-6}$alkyl-O—C$_{1-6}$alkyl;

B is selected from the group consisting of:

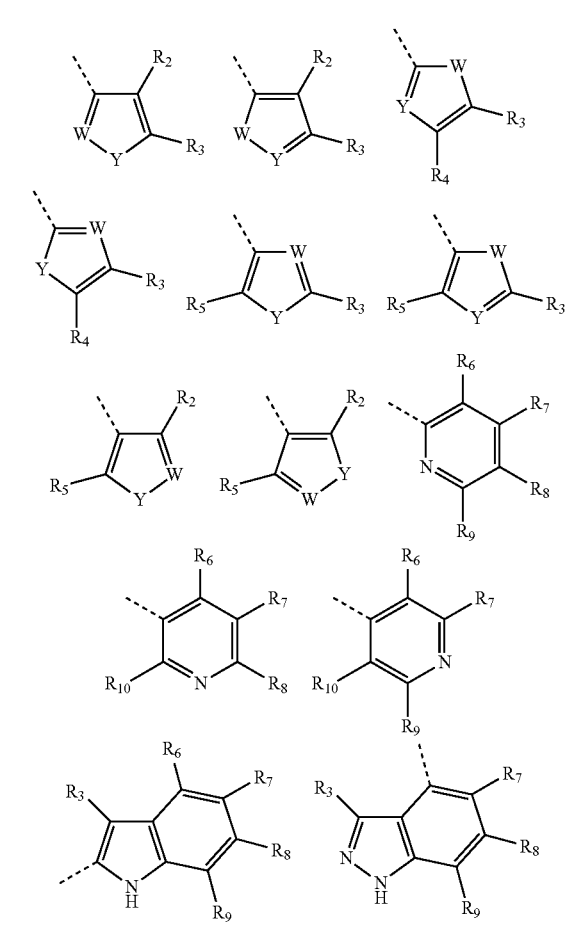

wherein

Y and W are independently selected from the group consisting of O, S, CR$^v$, CR$^v$R$^{vi}$, N, and NR$^{vii}$, wherein R$^v$ and R$^{vi}$ are selected form the group consisting of hydrogen, C$_{1-6}$alkyl, haloC$_{1-6}$alkyl, C$_{3-6}$cycloalkyl, heterocycloalkyl, aryl, heteroaryl, O—C$_{1-6}$alkyl, O—C$_{1-6}$alkylaryl, O—C$_{3-6}$cycloalkyl, O-heterocycloalkyl, O-haloC$_{1-6}$alkyl, C$_{1-6}$alkyl-O—C$_{1-6}$alkyl, C$_{1-6}$alkyl-O—C$_{3-6}$cycloalkyl, C$_{1-6}$alkyl-O-heterocycloalkyl, C$_{1-6}$alkyl-O-aryl, C$_{1-6}$alkyl-O-heteroaryl, hydroxy-C$_{1-6}$alkyl, COR$^{viii}$, COOR$^{viii}$, CONHR$^{viii}$, and CONR$^{ix}$R$^x$;

R$^{vii}$ is selected form the group consisting of hydrogen, C$_{1-6}$alkyl, haloC$_{1-6}$alkyl, C$_{3-6}$cycloalkyl, heterocycloalkyl, aryl, heteroaryl, C$_{2-6}$alkyl-O—C$_{1-6}$alkyl, C$_{2-6}$alkyl-O—C$_{3-6}$cycloalkyl, C$_{2-6}$alkyl-O-heterocycloalkyl, C$_{2-6}$alkyl-O-aryl, and C$_{2-6}$alkyl-O-heteroaryl;

R$_2$, R$_3$, R$_4$, R$_5$, R$_6$, R$_7$, R$_8$, R$_9$ and R$_{10}$ are independently selected from the group consisting of hydrogen, C$_{1-6}$alkyl, haloC$_{1-6}$alkyl, C$_{3-6}$cycloalkyl, heterocycloalkyl, aryl, heteroaryl, COR$^{viii}$, COOR$^{viii}$, CONHR$^{viii}$, CONR$^{ix}$R$^x$, OH, O—C$_{1-6}$alkyl, O—C$_{1-6}$alkylaryl, O—C$_{3-6}$cycloalkyl, O-heterocycloalkyl, O-heteroaryl, O-aryl, O-haloC$_{1-6}$alkyl, C$_{1-6}$alkyl-O—C$_{1-6}$alkyl, C$_{1-6}$alkyl-O—C$_{3-6}$cycloalkyl, C$_{1-6}$alkyl-O-heterocycloalkyl, C$_{1-6}$alkyl-O-aryl, C$_{1-6}$alkyl-O-heteroaryl, hydroxy-C$_{1-6}$alkyl, CN, NO$_2$, NR$^{ix}$R$^x$, N(R$^x$)COR$^{viii}$, N(R$^x$)COOR$^{viii}$, N(R$^x$)CONR$^{ix}$R$^x$, N(R$^x$)SO$_2$R$^{xi}$, SO$_2$R$^{xi}$, SO$_2$NR$^{ix}$R$^x$, and halogen;

R$^{viii}$ is selected from the group consisting of hydrogen, C$_{1-6}$alkyl, haloC$_{1-6}$alkyl, C$_{3-6}$cycloalkyl, heterocycloalkyl, aryl, heteroaryl, C$_{1-6}$alkyl-O—C$_{1-6}$alkyl, and C$_{1-6}$alkyl-O-heterocycloalkyl;

R$^{ix}$ is selected from the group consisting of hydrogen, C$_{1-6}$alkyl, haloC$_{1-6}$alkyl, C$_{3-6}$cycloalkyl, heterocycloalkyl, aryl, and heteroaryl;

R$^x$ is selected from the group consisting of hydrogen, C$_{1-6}$alkyl, haloC$_{1-6}$alkyl, C$_{3-6}$cycloalkyl, heterocycloalkyl, aryl, heteroaryl, C$_{1-6}$alkyl-O—C$_{2-6}$alkyl, and hydroxy-C$_{2-6}$alkyl;

R$^{xi}$ is selected from the group consisting of C$_{1-6}$alkyl, haloC$_{1-6}$alkyl, C$_{3-6}$cycloalkyl, heterocycloalkyl, aryl, and heteroaryl;

provided that at least one of R$^{iii}$ or R$^{iv}$ of at least one of A$_1$, A$_2$, A$_3$ or A$_4$ is not H.

9. The compound of Formula (Tb) according to claim 8, for the use in the treatment of a disease selected from the group consisting of cystic fibrosis, chronic obstructive pulmonary disease, chronic constipation, and dry eye syndrome.

10. The compound of Formula (Tb) according to claim 8, for the use in the treatment of cystic fibrosis.

11. The compound of Formula (Tb) according to claim 8, selected from the group consisting of:

040 (2-methyl-5,6,7,8,9,10-hexahydro-7,10-epiminocyclohepta[b]indol-11-yl)(5-(trifluoromethyl)-1H-pyrazol-3-yl)methanone
041 (1H-indol-2-yl)(2-methyl-5,6,7,8,9,10-hexahydro-7,10-epiminocyclohepta[b]indol-11-yl)methanone
042 (5-bromofuran-2-yl)(2-methyl-5,6,7,8,9,10-hexahydro-7,10-epiminocyclohepta[b]indol-11-yl)methanone
047 [5-(trifluoromethyl)-1H-pyrazol-3-yl]-(4,4,8-trimethyl-3,5-dihydro-1H-pyrido[4,3-b]indol-2-yl)methanone
053 (4-fluoro-2-methyl-5,6,7,8,9,10-hexahydro-7,10-epiminocyclohepta[b]indol-11-yl)(5-(trifluoromethyl)-1H-pyrazol-3-yl)methanone
055 (4-fluoro-1-methyl-5,6,7,8,9,10-hexahydro-7,10-epiminocyclohepta[b]indol-11-yl)(5-(trifluoromethyl)-1H-pyrazol-3-yl)methanone
077 (6-fluoro-4,4,9-trimethyl-3,5-dihydro-1H-pyrido[4,3-b]indol-2-yl)-[5-(trifluoromethyl)-1H-pyrazol-3-yl]methanone
079 (7R,10S)- or (7S,10R)-(4-fluoro-1-methyl-5,6,7,8,9,10-hexahydro-7,10-epiminocyclohepta [b]indol-11-yl)(5-(trifluoromethyl)-1H-pyrazol-3-yl)methanone
080 (7S,10R)- or (7R,10S)-4-fluoro-1-methyl-5,6,7,8,9,10-hexahydro-7,10-epiminocyclohepta [b]indol-11-yl)(5-(trifluoromethyl)-1H-pyrazol-3-yl)methanone
105 rac-(6-fluoro-3,9-dimethyl-1,3,4,5-tetrahydropyrido[4,3-b]indol-2-yl)-[5-(trifluoromethyl)-1H-pyrazol-3-yl]methanone
106 rac-(6-fluoro-1,9-dimethyl-1,3,4,5-tetrahydropyrido[4,3-b]indol-2-yl)-[5-(trifluoromethyl)-1H-pyrazol-3-yl]methanone
108 (R)-(6-fluoro-3,9-dimethyl-1,3,4,5-tetrahydropyrido[4,3-b]indol-2-yl)-[5-(trifluoromethyl)-1H-pyrazol-3-yl]methanone
109 (S)-(6-fluoro-3,9-dimethyl-1,3,4,5-tetrahydropyrido[4,3-b]indol-2-yl)-[5-(trifluoromethyl)-1H-pyrazol-3-yl]methanone
112 (6-fluoro-3,3,9-trimethyl-4,5-dihydro-1H-pyrido[4,3-b]indol-2-yl)-[5-(trifluoromethyl)-1H-pyrazol-3-yl]methanone
113 [(S)-6,9-difluoro-3-methyl-1,3,4,5-tetrahydropyrido[4,3-b]indol-2-yl]-[5-(trifluoromethyl)-1H-pyrazol-3-yl]methanone
114 [(R)-6-fluoro-3,9-dimethyl-1,3,4,5-tetrahydropyrido[4,3-b]indol-2-yl]-(1H-indol-2-yl)methanone
115 [(S)-8-methoxy-6-fluoro-3-methyl-1,3,4,5-b]indol-2-yl]-[5-(trifluoromethyl)-1H-pyrazol-3-yl]methanone
116 rac-(6-fluoro-1-methyl-8-methoxy-1,3,4,5-tetrahydropyrido[4,3-b]indol-2-yl)-(5 (trifluoromethyl)-1H-pyrazol-3-yl)methanone
117 [(R)-8-methoxy-6-fluoro-3-methyl-1,3,4,5-tetrahydropyrido[4,3-b]indol-2-yl]-[5-(trifluoromethyl)-1H-pyrazol-3-yl]methanone
121 (6-fluoro-3-isopropyl-8-methoxy-1,3,4,5-tetrahydropyrido[4,3-b]indol-2-yl)-(5-methyl-1H-pyrazol-3-yl)methanone
122 (6,9-difluoro-8-methoxy-spiro[4,5-dihydro-3H-pyrido[4,3-b]indole-1,1'-cyclopropane]-2-yl)-(5-methyl-1H-pyrazol-3-yl)methanone
123 (6,9-difluoro-1,3-dimethyl-1,3,4,5-tetrahydropyrido[4,3-b]indol-2-yl)-(5-methyl-1H-pyrazol-3-yl)methanone
124 (6,9-difluoro-8-methoxy-spiro[4,5-dihydro-1H-pyrido[4,3-b]indole-3,1'-cyclopropane]-2-yl)-(5-methyl-1H-pyrazol-3-yl)methanone
125 [6-(dimethylamino)-1H-indol-2-yl]-(8-methylspiro[3,5-dihydro-1H-pyrido[4,3-b]indole-4,1'-cyclopropane]-2-yl)methanone
126 (4-ethyl-6-fluoro-9-methyl-1,3,4,5-tetrahydropyrido[4,3-b]indol-2-yl)-(5-methyl-1H-pyrazol-3-yl)methanone
127 6-fluoro-9-methyl-2-(5-methyl-1H-pyrazole-3-carbonyl)-1,3,4,5-tetrahydropyrido[4,3-b]indole-3-carboxylic acid
128 [6-(dimethylamino)-1H-indol-2-yl]-[8-methyl-1-(trifluoromethyl)-1,3,4,5-tetrahydropyrido[4,3-b]indol-2-yl]methanone
129 (6-fluoro-8-methoxy-1,4-dimethyl-1,3,4,5-tetrahydropyrido[4,3-b]indol-2-yl)-(5-methyl-1H-pyrazol-3-yl)methanone
130 (6-fluoro-4-methoxy-9-methyl-1,3,4,5-tetrahydropyrido[4,3-b]indol-2-yl)-(5-methyl-1H-pyrazol-3-yl)methanone
131 6-fluoro-4,9-dimethyl-2-(5-methyl-1H-pyrazole-3-carbonyl)-3,5-dihydro-1H-pyrido[4,3-b]indole-4-carboxylic acid
132 (4,4-difluoro-8-methoxy-3,5-dihydro-1H-pyrido[4,3-b]indol-2-yl)-(5-methyl-1H-pyrazol-3-yl)methanone
133 (3,6-dimethyl-4,8,10-triazatricyclo[7.4.0.02,7]trideca-1(9),2(7),10,12-tetraen-4-yl)-(5-methyl-1H-pyrazol-3-yl)methanone
134 (6,6-dimethyl-4,8,12-triazatricyclo[7.4.0.02,7]trideca-1(9),2(7),10,12-tetraen-4-yl)-(5-methyl-1H-pyrazol-3-yl)methanone and
135 2-(5-bromofuran-2-carbonyl)-8-methoxy-1,3,4,5-tetrahydropyrido[4,3-b]indole-4-carboxylic acid.

* * * * *